(12) United States Patent
Tomsovic et al.

(10) Patent No.: US 8,845,837 B2
(45) Date of Patent: *Sep. 30, 2014

(54) METHOD OF MANUFACTURING TAMPONS

(71) Applicant: Kimberly-Clark Worldwide, Inc., Neenah, WI (US)

(72) Inventors: Charles Robert Tomsovic, Omro, WI (US); Nick Wolter, Greenville, WI (US); Wayne Beyer, Appleton, WI (US); Ronald A. Hilt, Oshkosh, WI (US); Joshua Fiedorowicz, Appleton, WI (US); Brian Alberts, Harrison, WI (US); Martin Gottvald, Brno (CZ); Steve Gehling, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/664,605

(22) Filed: Oct. 31, 2012

(65) Prior Publication Data

US 2014/0115845 A1    May 1, 2014

(51) Int. Cl.
*A61F 13/15* (2006.01)
*A61F 13/20* (2006.01)

(52) U.S. Cl.
CPC .......... *A61F 13/2071* (2013.01); *A61F 13/2068* (2013.01); *Y10S 604/904* (2013.01)
USPC ...... 156/196; 156/269; 156/265; 604/385.17; 604/904

(58) Field of Classification Search
CPC ............ A61F 13/2085; A61F 13/2071; A61F 13/2068; A61F 13/2054

USPC ...................... 156/196, 265, 269; 604/385.17
See application file for complete search history.

(56) References Cited

U.S. PATENT DOCUMENTS

| | | | |
|---|---|---|---|
| 2,112,021 A | 3/1938 | Harris | |
| 2,123,750 A | 7/1938 | Schulz | |
| 2,330,257 A | 9/1943 | Bailey | |
| 2,464,310 A | 3/1949 | Harwood | |
| 3,037,506 A | 6/1962 | Penska | |
| 3,340,874 A | 9/1967 | Burgeni | |
| 3,815,601 A | 6/1974 | Schaefer | |
| 4,212,301 A | 7/1980 | Johnson | |
| 4,359,357 A | 11/1982 | Friese | |
| 4,642,108 A | 2/1987 | Sustmann | |
| 4,816,100 A * | 3/1989 | Friese ........................... 156/191 |

(Continued)

OTHER PUBLICATIONS

Kamath, M.G., et al, Thermal Bonding of Nonwoven Fabrics, http://www.engr.utk.edu/mse/Textiles/Thermal%20Bonding.htm, Jun. 4, 2014, 12 pages.

*Primary Examiner* — Michael Orlando
*Assistant Examiner* — Marta Dulko
(74) *Attorney, Agent, or Firm* — Armstrong Teasdale LLP

(57) ABSTRACT

A method of manufacturing a tampon includes transporting a web of material in a machine direction. The web of material has a base web and an absorbent web. The absorbent web has a free end and a bonded end wherein the bonded end is bonded to the base web. At least the free end of the absorbent web of the web to is controlled to inhibit movement of the absorbent web relative to the base web. The web of material is cut into discrete web segments while controlling at least the free end of the absorbent web. The discrete web segments is bonded to a substrate.

8 Claims, 54 Drawing Sheets

(56) References Cited

U.S. PATENT DOCUMENTS

| | | | |
|---|---|---|---|
| 5,047,024 A * | 9/1991 | Glassman | 604/380 |
| 5,112,348 A | 5/1992 | Glassman | |
| 5,185,010 A * | 2/1993 | Brown, Jr. | 604/379 |
| 5,370,633 A | 12/1994 | Villalta | |
| 5,584,827 A | 12/1996 | Korteweg et al. | |
| 6,039,716 A | 3/2000 | Jessup et al. | |
| 6,142,984 A | 11/2000 | Brown et al. | |
| 6,177,608 B1 * | 1/2001 | Weinstrauch | 604/380 |
| 6,203,654 B1 | 3/2001 | McFall et al. | |
| 6,258,075 B1 | 7/2001 | Taylor et al. | |
| 6,310,269 B1 | 10/2001 | Friese et al. | |
| 6,315,763 B1 | 11/2001 | Albright et al. | |
| 6,415,484 B1 * | 7/2002 | Moser | 28/118 |
| 6,635,799 B1 | 10/2003 | Osborn, III et al. | |
| 6,740,070 B2 | 5/2004 | Agyapong et al. | |
| 6,743,212 B1 | 6/2004 | Cole et al. | |
| 6,758,839 B2 * | 7/2004 | Lochte et al. | 604/385.18 |
| 6,773,423 B2 | 8/2004 | Osborn et al. | |
| 6,837,882 B2 | 1/2005 | Agyapong et al. | |
| 6,840,927 B2 | 1/2005 | Hasse et al. | |
| 6,953,456 B2 * | 10/2005 | Fuchs et al. | 604/385.17 |
| 7,192,421 B2 | 3/2007 | Hasse et al. | |
| 7,387,622 B1 | 6/2008 | Pauley et al. | |
| 7,553,532 B2 | 6/2009 | Turner et al. | |
| 7,677,189 B2 | 3/2010 | Kondo et al. | |
| 7,967,803 B2 * | 6/2011 | Van Ingelgem et al. | 604/385.17 |
| 7,977,532 B2 * | 7/2011 | Hasse et al. | 604/381 |
| 8,026,409 B2 * | 9/2011 | Andersch | 604/383 |
| 2002/0120243 A1 | 8/2002 | Kraemer et al. | |
| 2003/0097112 A1 | 5/2003 | Gilbert et al. | |
| 2003/0149416 A1 | 8/2003 | Cole et al. | |
| 2003/0208180 A1 | 11/2003 | Fuchs et al. | |
| 2004/0019317 A1 | 1/2004 | Takagi et al. | |
| 2005/0087292 A1 | 4/2005 | McFall et al. | |
| 2005/0096620 A1 * | 5/2005 | Awolin et al. | 604/385.18 |
| 2005/0256484 A1 * | 11/2005 | Chase et al. | 604/385.18 |
| 2007/0073257 A1 | 3/2007 | Buck et al. | |
| 2007/0260211 A1 * | 11/2007 | Schmidt-Forst | 604/385.17 |
| 2008/0097366 A1 | 4/2008 | Mathews | |
| 2008/0132868 A1 | 6/2008 | Jorgensen et al. | |
| 2008/0262463 A1 | 10/2008 | Noel et al. | |
| 2008/0287902 A1 | 11/2008 | Edgett et al. | |
| 2010/0114054 A1 | 5/2010 | Mueller et al. | |
| 2011/0160526 A1 | 6/2011 | Zunker et al. | 600/29 |
| 2013/0165891 A1 * | 6/2013 | McDaniel et al. | 604/385.17 |
| 2014/0115845 A1 * | 5/2014 | Tomsovic et al. | 28/118 |

* cited by examiner

METHOD OF MANUFACTURING TAMPONS

BACKGROUND

Currently, there are two basic types of tampons used for feminine hygiene. The first type is a digitally insertable tampon which is designed to be inserted directly by the user's fingers. The second type is an applicator style tampon which is designed to be inserted with the aid of an applicator. Both types are usually made by folding or rolling rectangular strips of absorbent material into a blank and then compressing the blank into a cylindrically-shaped pledget. The pledget may or may not have a cover. In both types, a withdrawal string can be attached to the pledget. The combination of a pledget and a withdrawal string is considered a useable tampon product. The tampon can then be wrapped and packaged for sale. In the applicator style tampon, the tampons can be assembled into an applicator prior to being wrapped and packaged.

Tampons work by acquiring vaginal fluids, including menses, at the interface between the tampon and vaginal wall. To ensure this contact, current tampons alter the vagina immediately upon insertion. This alteration contributes to early premature, "by-pass" leakage. After the tampon absorbs the vaginal fluids, including menses, most tampons begin to expand uniformly and globally, further contributing to this leakage. At the same time, the tampon begins to become more flexible and conformable to allow for a better global/macro fit to the vagina. This predetermined and uniform tampon response that drives this global/macro expansion is governed by the tampon construction and materials.

Even when fluid is acquired locally and the deformational forces on the tampon by the vaginal environment are applied locally, with current tampons the construction or materials of the tampons inhibits or constrains their capacity to expand or adapt to give a local/micro fit. These constructions and materials force the entire tampon to respond to these local fluid acquisition and deformational forces through material connectivity or material stiffness.

When attempts are made to allow for more local adaptation in tampon constructions, the constructions do not acquire the fluids well because of inadequate contact area because they cannot match the local contours of the vaginal wall or are not conformable enough to adapt to the women's individual local contours (e.g. folds and convolutions) found on the vaginal wall. In addition, these attempts create integrity issues with the tampons that lead to portions of the tampon remaining within the vagina after tampon removal. This inadequate contact is especially true during the wiping action of the vagina by the tampon when the tampon is inserted and removed.

Current tampon construction processes construct these inadequate tampons that have this predetermined and uniform tampon response. They create these constraints, inadequate contact area, and integrity issues in order to drive this predetermined and uniform tampon response and, therefore, limit the tampon from effectively responding locally. New construction processes are needed to construct tampons that overcome the inadequacy of current tampons.

There remains a need for a tampon that responds locally to meet the individual protection needs of women and processes to make such tampons. There remains a need for a tampon that prevents leakage of body fluid after being inserted into a woman's vagina. There remains a need for a tampon that provides efficient utilization of the entire tampon structure during use. There remains a need for a tampon that provides a customized fit to the anatomy of a woman's vaginal cavity. There remains a need for a tampon that can deform and come into contact with the folds and convolutions of the walls of the vaginal cavity and acquire any contacted fluid.

One potential solution to these needs is to provide a tampon having a plurality of relatively small, discrete contact elements that are adapted to contact the folds and convolutions of the walls of the vaginal cavity and thereby reduce the potential for leakage of body fluid (e.g., menses) past the tampon. Although incorporating the plurality of discrete contact elements into a tampon will potentially reduce tampon leakage, the process to incorporate them into a usable tampon presents many significant challenges.

One of these challenges is meeting the Food and Drug Administration (FDA) guidelines for a Class 2 medical device. These guidelines are in place to prevent defective tampons from causing adverse reaction with a consumer which includes, for example, increased risk of Toxic Shock Syndrome (TSS) and vaginal infections. Three of these FDA guidelines relate to absorbency, fiber shedding (residual fiber retention) and tampon integrity. The presence of these discrete contact elements on the tampon can impact the tampon performance in respect to each and every one of these guidelines. To minimize the potential of the discrete contact elements negatively impacting tampon performance, steps have to be taken during manufacturing to prevent tampon process damage. Tampon process damage can potentially alter the performance of the tampon from it design requirements and includes, for example, lost contact elements, incorrectly formed or otherwise damaged contact elements, and weakened contact elements.

As used herein, tampon process damage is any alteration to the tampon that is caused by the process to create a damaged tampon. This damage can include missed or inappropriate placed contact elements and surface process damage. When this damage causes the tampon to be outside the FDA guidelines, the tampon is a said to be a defective tampon. Surface process damage is any alteration to a surface that is caused by the process to create a damaged surface. Each surface of the tampon is designed to have certain design characteristics. When any of these design characteristics vary significantly from target values, the surface is said to be a damage surface. These design characteristics includes surface size, shape, configuration, and absorbency and mechanical characteristics or properties.

Examples include missing and malformed surface and deteriorated absorbency or mechanical properties. A malformed surface includes improperly sized, shaped, cut, bent, and folded surface and especially malformations that alter the surface contact area with the vaginal surfaces. A deteriorated absorbency or mechanical property includes reduced wettability, permeability, and mechanical strength and especially deteriorations that alter the surfaces ability to conform to vaginal surfaces and acquire, intake, and distribute vaginal fluids.

The process used to manufacture the discrete contact elements of the tampon must be able to make the contact elements consistently and reproducibly at high speeds and ensures that only tampons without significant process and/or surface damage are sold to consumers. Thus, there remains a need for a tampon processes capable of consistently and reproducibly manufacturing tampons with discrete contact elements at high speeds and without significant process and/or surface damage.

BRIEF DESCRIPTION

In one aspect, a method of manufacturing a tampon generally comprises transporting a web of material in a machine direction. The web of material comprises a base web and an absorbent web. The absorbent web has a free end and a bonded end wherein the bonded end is bonded to the base web. At least the free end of the absorbent web of the web is controlled to inhibit movement of the absorbent web relative to the base web. The web of material is cut into discrete web segments while controlling at least the free end of the absorbent web and the discrete web segments are bonded to a substrate.

In another aspect, a method of manufacturing a tampon generally comprises transporting a first web of material in a machine direction and transporting a second web of material in the machine direction. The second web of material comprises a base web and an absorbent web. The absorbent web has a free end and a bonded end wherein the bonded end is bonded to the base web. At least the free end of the absorbent web of the second web is controlled to inhibit movement of the absorbent web relative to the base web. The second web of material is cut into discrete web segments while controlling at least the free end of the absorbent web. The discrete web segments are bonded to the first web of material at predetermined intervals.

In yet another aspect, a method of manufacturing a tampon generally comprises transporting a web of material in a machine direction. The web of material comprises a base web and an absorbent web. The absorbent web has a free end and a bonded end wherein the bonded end is bonded to the base web. The free end includes a plurality of slits. At least the free end of the absorbent web of the web is controlled to inhibit movement of the absorbent web relative to the base web. The web of material is cut in the cross machine direction to form discrete web segments while controlling at least the free end of the absorbent web. The discrete web segments are bonded to a substrate.

DETAILED DESCRIPTION OF THE DRAWINGS

The tampon of the current disclosure can be inserted above the introital region of a woman's vagina, can intercept the fluid flow of menses, blood, and other body fluids, and can prevent the fluid from exiting the vagina. While the pledgets and tampons of the current disclosure are described for use as a menstrual device, it will be readily apparent that the pledgets and tampons can also be used as any other suitable vaginal insert, such as a pessary. Likewise, while the pledgets and tampons of the current disclosure are generally described as being "absorbent," it will be readily apparent that the pledgets and tampons may be coated or otherwise treated to be partially or completely non-absorbent.

In an embodiment, the pledget and tampon of the current disclosure can have a contact element. In an embodiment, the contact element can allow the pledget and the tampon to respond locally to the changes in the vaginal environment and can effectively acquire fluid locally to accommodate the uniqueness of a woman's vaginal environment and her period.

Figure 1:
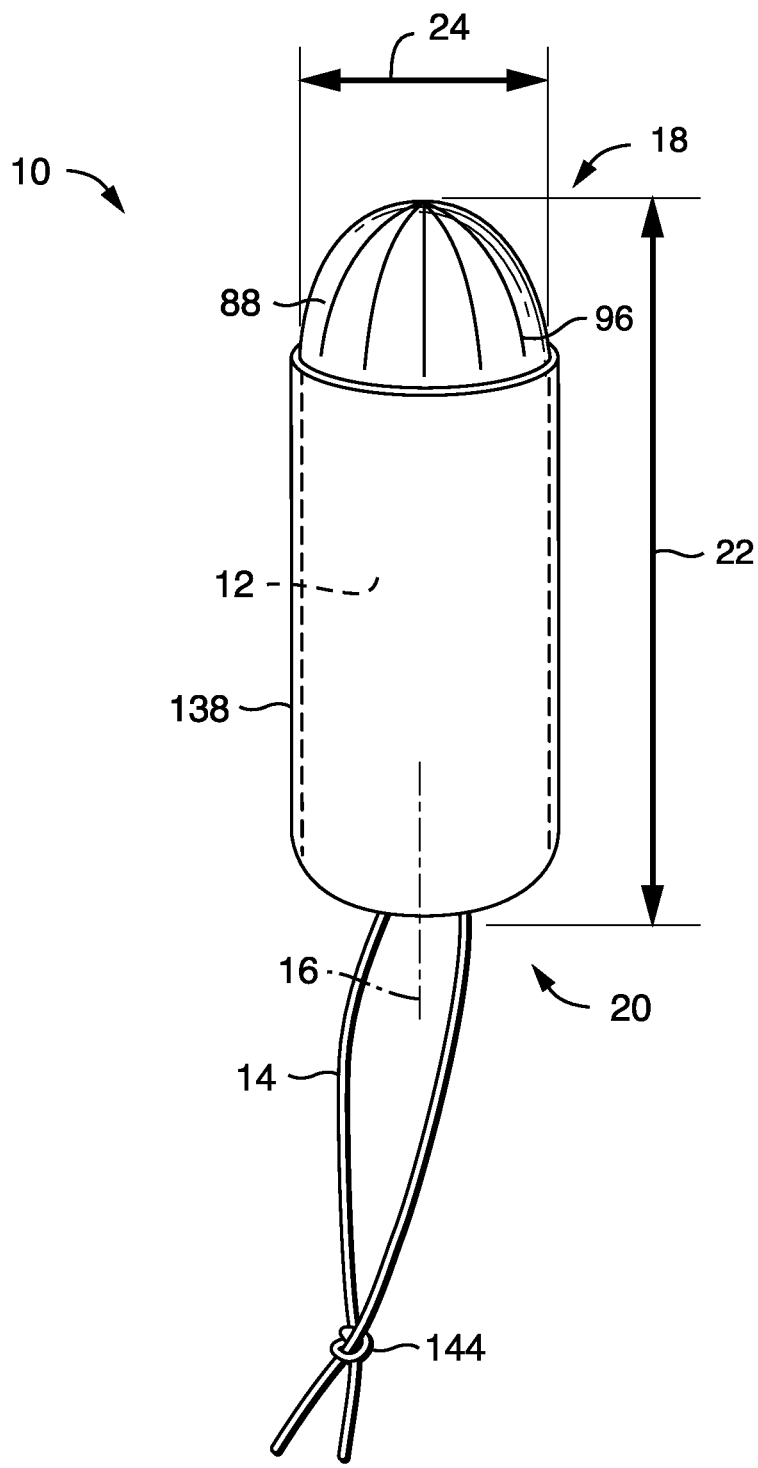
FIG. 1 is a perspective view of an embodiment of a tampon in a compressed configuration.

A non-limiting embodiment of a tampon 10 of the current disclosure is illustrated in FIG. 1. The tampon 10 can be inserted into a woman's vaginal cavity to prevent menses from exiting the vaginal opening by contacting and absorbing the flow of menses. The term "menses," as used herein, includes blood, tissue debris, and other bodily fluids emitted from the vaginal opening. The tampon 10 can have a compressed, generally cylindrical shaped pledget 12 and a withdrawal aid 14. In some embodiments, the generally cylindrical shape of the pledget 12 can have a cross-section that can be at least one of an oval, circle, square, rectangle, or any other cross-sectional shape known in the art. The term "cross-section" refers herein to the plane which extends laterally through the tampon 10, and which is orthogonal to the longitudinal axis 16 of the pledget 12, and consequently, of the tampon 10. The tampon 10 can have an insertion end 18 and a withdrawal end 20. The tampon 10 can have a length 22 wherein the length 22 is the measurement of the tampon 10 along the longitudinal axis 16 originating at one end (insertion or withdrawal) of the tampon 10 and ending at the opposite end (insertion or withdrawal) of the tampon 10. In some embodiments, the tampon 10 can have a length 22 from about 30 mm to about 80 mm. The tampon 10 can have a width 24, which unless otherwise stated herein, can correspond to the greatest cross-sectional dimension along the longitudinal axis 16 of the tampon 10. In some embodiments, the tampon 10 can have a compressed width 24 prior to usage from about 2, 5, 8, 10, 12, or 14 mm to about 20 or 30 mm. The tampon 10 may be straight or non-linear in shape, such as curved along the longitudinal axis 16.

As noted above, the tampon 10 can have a pledget 12. The pledget 12 can be formed from a blank 28, such as a softwind, wherein the blank 28 can be formed from a fleece 30. The fleece 30 can have an absorbent structure 34 which can be a single layer of a fibrous material or can be multiple layers of fibrous material. In an embodiment, an absorbent structure 34 can be formed of at least two layers of fibrous materials. The absorbent structure 34 can be manufactured via processes such as, for example, a multi-bank laydown, bonding pre-formed layers together, or a combination thereof. Such processes can produce a nonwoven ribbon 32 having an absorbent structure 34 of a single layer or multiple layers of fibrous materials. In an embodiment, the nonwoven ribbon 32 can be separated into individual units of fleece 30, wherein each unit of fleece 30 can have the absorbent structure 34.

In an embodiment in which the absorbent structure 34 is multi-layered, the absorbent structure 34 can have at least 2, 3, 4, 5, 6, or 7 layers of fibrous material. In an embodiment in which the absorbent structure 34 is multi-layered, a layer can be identical to another layer, can be different from another layer, or can be identical to at least one other layer and can be different from at least one other layer. In an embodiment in which an absorbent structure 34 is multi-layered and at least one layer is different from another layer, the layers can be different from each other by at least 1, 2, 3, 4 or 5 aspects. Non-limiting examples of aspects of differences can include density, thickness, type of fibrous material in a layer, amount of fibrous material in a layer, hydrophilic/hydrophobic characteristics, and strength/integrity characteristics (which can include reinforcing fibrous materials).

In an embodiment in which the absorbent structure 34 is multi-layered, the absorbent structure 34 can be manufactured by bonding at least two pre-formed layers together. In such an embodiment, the pre-formed layers can be brought into contact with each other and bonded together by any suitable method. In such an embodiment, the bonded layers can then be bonded to at least one additional layer. The at least one additional layer can be pre-formed or can be a laid down fibrous material.

In an embodiment in which the absorbent structure 34 is multi-layered, the absorbent structure 34 can be manufactured via a process such as a multi-bank fibrous material laydown. In such a process, fibrous material in a first bank can be laid down to form a first layer and fibrous material in a second bank can be laid down onto the first layer and formed into a second layer. The second layer can then, if desired, be bonded to the first layer. In an embodiment, fibrous material in at least one additional bank can be laid down onto the prior layers and formed into at least one additional layer if so desired. The additional layer(s) can be bonded to the prior formed and bonded layers. In an embodiment, a pre-formed layer can be bonded to the formed and bonded layers.

Figure 2:
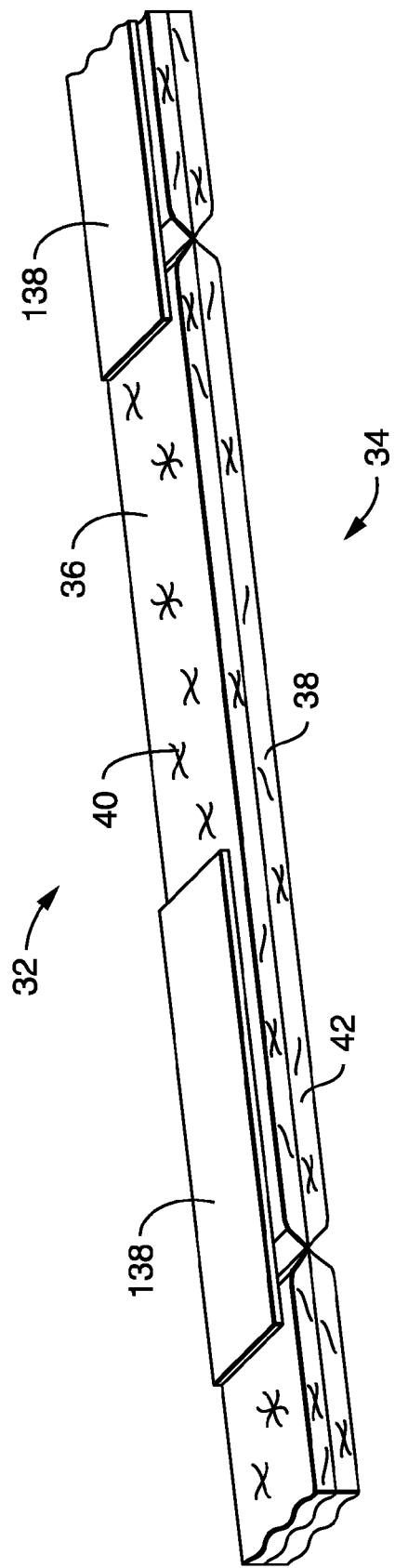
FIG. 2 is a perspective view of an embodiment of a nonwoven ribbon.

FIG. 2 provides a non-limiting illustration of a nonwoven ribbon 32 which can have a multi-layer absorbent structure 34 of at least two layers, such as layers 36 and 38. The nonwoven ribbon 32 can be manufactured via either a multi-bank fibrous material laydown method, via bonding of pre-formed layers, or via a combination of the described methods. It is to be understood that while the description and figures herein generally illustrate a nonwoven ribbon 32, an absorbent structure 34 and/or a fleece 30 having two layers, such as layers 36 and 38, a nonwoven ribbon 32, an absorbent structure 34 and/or a fleece 30 can have more than two layers and the description herein is applicable to a nonwoven ribbon 32, an absorbent structure 34 and/or a fleece 30 having more than two layers.

In an embodiment, the nonwoven ribbon 32 can have more than two layers. In an embodiment, a layer(s), such as layer(s) 36 and/or 38, can be hydrophobic or hydrophilic. In an embodiment, a layer(s), such as layer(s) 36 and/or 38, can be treated with a surfactant or other material to make the layer(s) hydrophilic or to make the layer(s) more hydrophilic. As will be described herein, in a nonwoven ribbon 32 having more than one layer, the layers, such as layers 36 and 38, can be in communication with each other. In an embodiment, the layers, such as layers 36 and 38, can be in communication with each other and can be bonded to each other. The terms "bonded" or "bonding" refer herein to the joining, adhering, connecting, attaching or the like of two elements. Two elements will be considered bonded together when they are joined, adhered, connected, or attached directly to one another or indirectly to one another, such as when each is directly joined, adhered, connected or attached to intermediate elements. The bonding can occur by any method deemed suitable including, but not limited to, adhesives, heat bonding, vibration energy, mechanical bonding, chemical bonding, vacuum bonding, ultrasonic bonds, thermal bonds, pressure bonds, mechanical entanglement, hydroentanglement, microwave bonds, or any other conventional technique. The bonding can be continuous or it can be intermittent.

Each layer, such as layers 36 and 38, can be constructed from fibrous materials, such as fibrous materials 40 and 42, respectively. In an embodiment, the fibrous materials can include absorbent fibers. The fibrous materials can include, but are not limited to, natural and synthetic fibers such as, but not limited to, polyester, acetate, nylon, cellulosic fibers such as wood pulp, cotton, rayon, viscose, LYOCELL® such as from Lenzing Company of Austria, or mixtures of these or other cellulosic fibers. Natural fibers can include, but are not limited to, wool, cotton, flax, hemp and wood pulp. Wood pulps can include, but are not limited to, standard softwood fluffing grade such as CR-1654 (US Alliance Pulp Mills, Coosa, Ala.). Pulp may be modified in order to enhance the inherent characteristics of the fibers and their processability. Crimping can be imparted to the fibers by any means deemed suitable by one of ordinary skill. Curl may be imparted to the fibers by suitable methods such as, for example, chemical treatment or mechanical twisting. Curl can be imparted before crosslinking or stiffening. Pulps may be stiffened by the use of crosslinking agents such as formaldehyde or its derivatives, glutaraldehyde, epichlorohydrin, methylated compounds such as urea or urea derivatives, dialdehydes such as maleic anhydride, non-methylated urea derivatives, citric acid or other polycarboxylic acids. Pulp may also be stiffened by the use of heat or caustic treatments such as mercerization. Examples of these types of fibers include NHB416, which is a chemically cross-linked southern softwood pulp fiber which enhances wet modulus, available from Weyerhaeuser Corporation of Tacoma, Wash. Other non-limiting examples of useful pulps are debonded pulp (NF405) and non-debonded pulp (NB416) also from Weyerhaeuser. HPZ3 from Buckeye Technologies, Inc. of Memphis, Tenn., is an example of a fiber that has a chemical treatment that sets in a curl and twist, in addition to imparting added dry and wet stiffness and resilience to the fiber. Another suitable pulp is Buckeye HP2 pulp and still another is IP Supersoft from International Paper Corporation. The fibrous materials can include any suitable blend of fibers. For example, the fibrous materials can be formed from cellulose fibers such as cotton and rayon. The fibrous materials can be 100 wt % cotton, 100 wt % rayon, or a blend of cotton and rayon. In some embodiments, the cellulose fibers may be modified for super-absorbency. In an embodiment, a layer, such as layer 36 or 38, can have substantially the same fibrous material composition as another layer, such as layer 36 or 38. In an embodiment, a layer, such as layer 36 or 38, can have a fibrous material composition different from another layer, such as layer 36 or 38.

In an embodiment, the fibrous materials can have a staple length of from about 5, 10, 15 or 20 mm to about 30, 40 or 50 mm. In an embodiment, the fibrous materials can have a fiber size of from about 15 microns to about 28 microns. In an embodiment, the fibrous materials can have a denier of from about 1 or 2 to about 6. Denier is a unit of fineness of yarn based on a standard of 50 milligrams (mg) for 450 meters of yarn. The fibrous materials can have a circular, bi-lobal or tri-lobal cross-sectional configuration or any other configuration known to those skilled in the art. A bi-lobal configuration can have a cross-sectional profile which can look like a dog bone while a tri-lobal configuration can have a cross-sectional profile which can look like a "Y." In an embodiment, the fibrous materials can be bleached. In an embodiment, the fibrous materials can have a color.

In an embodiment, a layer(s), such as layer(s) 36 and/or 38, can contain fibrous materials such as binder fibers. In an embodiment, the binder fibers can have a fiber component which can bond or fuse to other fibers in the layer. Binder fibers can be natural fibers or synthetic fibers. Synthetic fibers can include, but are not limited to, those made from polyolefins, polyamides, polyesters, rayon, acrylics, viscose, superabsorbents, LYOCELL® regenerated cellulose and any other suitable synthetic fiber known to those skilled in the art. Non-limiting examples of polyolefins can include, but are not limited to, polyethylene such as Dow Chemical's ASPUN® 6811A linear low density polyethylene, 2553 LLDPE and 25355 and 12350 high density polyethylene. The polyethylenes can have melt flow rates, respectively, of about 26, 40, 25, and 12. Non-limiting examples of fiber forming polypropylenes can include, but are not limited to, Exxon Chemical Company's ESCORENE® PD 3445 polypropylene and Montell Chemical Company's PF304. Another example of a fiber can be a bi-component polyethylene sheath and polyester core known as T255 made by Trevira of Germany. Other non-limiting examples of meltable bicomponent fibers can include, but are not limited to, fibers available from Unitika of Japan, such as, for example, Unitika MELTY 4080, and 6080 fibers, having either polyester sheaths or cores and polyethylene sheaths or cores. Another example can include, but is not limited to, fibers available from Fibervisions under the designation ETC Bounce fiber line, such as PET/PE fibers of about 2.2 decitex and about 40 mm staple fiber length. Non-limiting examples of rayon fibers include 1.5 denier Merge 18453 fibers from Accordis Cellulose Fibers Inc. of Axis, Ala. The fibrous materials can be treated by conventional compositions and/or processes to enable or enhance wettability.

In an embodiment, a layer(s), such as layer(s) 36 and/or 38, can contain fibrous materials such as cellulosic fibers, such as cotton and rayon. In an embodiment, a layer(s), such as layer (s) 36 and/or 38, can be 100% cotton, 100% rayon, or a blend of cotton and rayon fibers. In an embodiment, a blend of cotton and rayon fibers can be a blend of about 15% cotton and about 85% rayon; about 70% cotton and about 30% rayon; about 60% cotton and about 40% rayon; about 25% cotton and about 75% rayon; or a blend of about 6% cotton and about 94% rayon. The blend of cotton and rayon can be any blend as deemed suitable. In an embodiment, additional fibers such as polyester or other synthetic fibers can be added to the blend of cotton and rayon to add resilient features or bondability to a layer(s), such as layer(s) 36 and/or 38.

In an embodiment, a layer(s), such as layer(s) 36 and/or 38, can have a blend of viscose and binder fibers. In an embodiment, a blend of viscose and binder fibers can be a blend of from about 70% viscose to about 95% viscose with the remainder from about 30% to about 5% binder fiber. In an embodiment, a blend of viscose and binder fibers can be a blend of from about 85-90% viscose and the remainder from about 15-10% binder fiber. The blend of viscose and binder fibers can be any blend as deemed suitable.

Various methods known to those skilled in the art can be used to prepare each layer, such as layers 36 and 38. Such methods can include, but are not limited to, airlaying, carding, wetlaying, needlepunching, mechanical entanglement, hydroentangling, and any other known method deemed suitable by one of ordinary skill. In an embodiment, a bonded carded web can be made from staple fibers. In such an embodiment, the fibers can be longer than about 20, 30 or 35 mm. The fibers can be purchased in bales which can be placed in a picker to separate the fibers. The fibers can then be sent through a combing or carding unit, which can further break apart and align the staple fibers in the machine direction to form a generally machine direction-oriented fibrous nonwoven web. Once the web is formed, it can then be bonded by one or more of several known bonding methods, such as through air bonding or pattern bonding. In an embodiment, a dry laid web can be made from staple fibers. In such an embodiment, the fibers can be about 20 mm or longer. In dry laying, fibers or tufts of fibers of a first type (e.g., absorbent fibers and/or binder fibers) can be fed to a first rotating vacuum drum and fibers or tufts of fibers of a second type (e.g., absorbent fibers and/or binder fibers) can be fed to a second rotating vacuum drum. The fibers can then be laid down by suction to form mats of fibers. The mats of fibers can be doffed from the vacuum drums and combed via rotating lickerins. The lickerins can have peripheral teeth which can comb the fibers from the mat. The combed fibers can be doffed from the lickerins via centrifugal force and placed into a fiber mixing and expansion chamber. The mixed fibers can be placed on a vacuum screen to form a random fiber web comprising the first and second fiber types. The flow and velocity of each independent fiber stream can be controlled to provide the desired quantity of each fiber type. It is to be understood that a layer, such as layer 36 or 38, can be prepared using the same method as another layer, such as layer 36 or 38, or using a method different than another layer, 36 or 38.

In an embodiment, at least one of the layers, such as layers 36 and/or 38, can be prepared using an airlaying process. In such an embodiment, the airlaid fibers can contain a first fiber and a second fiber, wherein the first fiber can be a binder fiber and the second fiber can be an absorbent fiber.

In an embodiment in which binder fibers are present, the binder fibers can be activated to create a three-dimensional fiber matrix. In such an embodiment, the activation can be completed by any suitable heating step including, but not limited to, convection heating, through air heating, superheated steam, microwave heating, radiant heating, radio frequency heating, and the like, and combinations thereof. In some embodiments, the activation can be accomplished by heating the layer(s), such as layer(s) 36 and/or 38, containing the binder fibers at a temperature of from about 240° F. to about 428° F. (about 115° C. to about 220° C.) to activate the binder fibers. It is to be understood that the bonding temperature selected should be selected based upon the fibrous materials which are being bonded together. Without being bound by theory, it is believed that during activation, the binder fibers can soften and become tacky and, therefore, bind to adjacent fibers creating a three-dimensional fiber matrix. It is believed that the three-dimensional fiber matrix can stabilize the layer(s), such as layer(s) 36 and/or 38, and can create a liquid stable network. It is to be understood that an additional component or finish can be added to the fibers to facilitate bonding of fibrous materials which are not necessarily compatible.

In an embodiment, the activation can be followed by a cooling step which can utilize any suitable means for reducing the temperature of the layer(s), such as layer(s) 36 and/or 38. In an embodiment, the layer(s), such as layer(s) 36 and/or 38, can be cooled by allowing the layer(s), such as layer(s) 36 and/or 38, to return to ambient temperature over a period of time. In an embodiment, the layer(s), such as layer(s) 36 and/or 38, can be cooled by chill rolls, cooling chambers, blowing conditioned air, or the like, and combinations thereof. In an embodiment, the cooling step can occur prior to compression of the layer(s), such as layer(s) 36 and/or 38, to establish a wet-stable three-dimensional structure.

In some embodiments, a layer(s), such as layer(s) 36 and/or 38, can be further manipulated such as, for example, being folded, corrugated, or otherwise processed.

The nonwoven ribbon 32 can be separated into individual units of fleece 30. The separation of the nonwoven ribbon 32 into individual units of fleece 30 can occur by any suitable method such as stretching, perforating, cutting such as with the use of a die cutter or a knife cutter, and the like. The individual units of fleece 30 can then be rolled, stacked, folded, or otherwise manipulated into blanks 28. The blanks 28 can then be formed into pledgets 12 in any manner deemed suitable. As a non-limiting example, the blanks 28 can undergo compression to form the pledgets 12.

In various embodiments, the fleece 30 and the resultant pledget 12 can have any suitable combination and ratio of fibrous material. In an embodiment, the fleece 30 and the resultant pledget 12 can have from about 70 to about 95 wt % absorbent fibers and from about 5 to about 30 wt % binder fibers. In an embodiment, the fleece 30 and the resultant pledget 12 can have from about 80 to about 90 wt % absorbent fibers and from about 10 to about 20 wt % binder fibers. In an embodiment, the fleece 30 and the resultant pledget 12 can have about 85 wt % absorbent fibers and about 15 wt % binder fibers. In an embodiment, the fleece 30 and the resultant pledget 12 can have from about 80 to about 90 wt % trilobal viscose rayon fibers and from about 10 to about 20 wt % bicomponent binder fibers. In an embodiment, the fleece 30 and the resultant pledget 12 can have about 85 wt % trilobal viscose rayon fibers and about 15 wt % bicomponent binder fibers. In an embodiment, the fleece 30 and the resultant pledget 12 can have greater than about 50, 55, 60, 65, 70, 80, 90, 95, 97, or 99 wt % absorbent fibers.

The fleece 30 can be any size and thickness that can ultimately be compressed into a pledget 12 having a vaginally insertable shape. In an embodiment, the size of the fleece 30 can range from about 40 mm to about 100, 200, 250 or 300 mm in width and from about 30 mm to about 80 mm in length. As described herein, the width of the fleece 30 can be measured as the distance between longitudinal edges of the fleece 30 and the length of the fleece 30 can be measured as the distance between transverse edges of the fleece 30. As described herein, the transverse edges of the fleece 30 can be located at the insertion and withdrawal ends, 18 and 20, respectively, of a resultant tampon 10. In an embodiment, the overall basis weight of the fleece 30 can range from about 15, 20, 25, 50, 75, 90, 100, 110, 120, 135 or 150 gsm to about 1,000, 1,100, 1,200, 1,300, 1,400, or 1,500 gsm.

Figure 3:
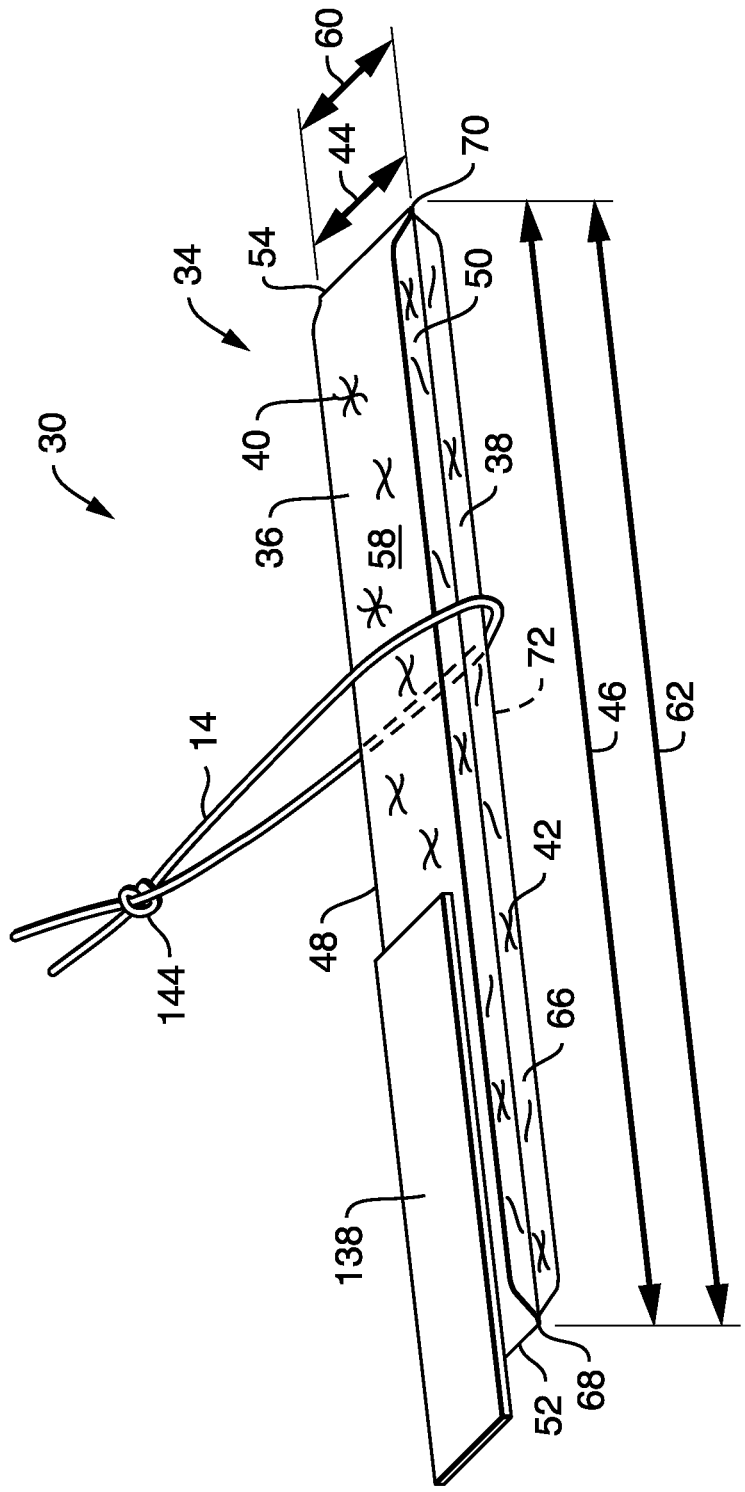
FIG. 3 is a perspective view of an embodiment of a fleece.

Referring to FIG. 3, a non-limiting example of a fleece 30 is illustrated in which the fleece 30 can have a multi-layer absorbent structure 34 of two layers, 36 and 38. In the non-limiting example illustrated, the first layer 36 can have a first length 44 and a first width 46. The first length 44 can extend from a first transverse edge 48 to a second transverse edge 50 of the first layer 36. The first width 46 can extend from a first longitudinal edge 52 to a second longitudinal edge 54 of the first layer 36. The first layer 36 can have a first surface 56 (illustrated in FIG. 4) and a second surface 58. Similarly, the second layer 38 can have a second length 60 and a second width 62. The second length 60 can extend from a first transverse edge 64 (illustrated in FIG. 4) to a second transverse edge 66 of the second layer 38. The second width 62 can extend from a first longitudinal edge 68 to a second longitudinal edge 70 of the second layer 38. The second layer 38 can have a first surface 72 and a second surface 74 (illustrated in FIG. 4). In a resultant tampon 10, the transverse edges of each layer, 36 and 38, can be located at the insertion end 18, the withdrawal end 20 or, as described herein, a location between the insertion end 18 and the withdrawal end 20. As a non-limiting example with regards to the fleece 30 illustrated in FIG. 3, transverse edges 50 and 66 can be located at the insertion end 18 of a resultant tampon 10 and transverse edges 48 and 64 can be located at the withdrawal end 20 of a resultant tampon 10.

The absorbent structure 34 can be constructed such that one of the surfaces, 56 or 58, of the first layer 36 can be at least partially in a face to face relationship with one of the surfaces, 72 or 74, of the second layer 38. In an embodiment, at least about 25% of one of the surfaces, 72 or 74, of the second layer 38 can be in a face to face relationship with one of the surfaces, 56 or 58, of the first layer 36. In an embodiment, at least about 25, 30, 35, 40, 45, 50, 55, 60, 65, 70, 75, 80, 85, 90, 95 or 100% of one of the surfaces, 72 or 74, of the second layer 38 can be in a face to face relationship with one of the surfaces, 56 or 58, of the first layer 36. In an embodiment, less than 100% of one of the surfaces, 72 or 74, of the second layer 38 can be in a face to face relationship with one of the surfaces, 56 or 58, of the first layer 36. In an embodiment, from about 25, 30, 35, 40, 45, or 50% to about 55, 60, 65, 70, 75, 80, 85, 90, 95 or 100% of one of the surfaces, 72 or 74, of the second layer 38 can be in a face to face relationship with one of the surfaces, 56 or 58, of the first layer 36.

In the exemplary illustration of FIG. 3, the first and second layers, 36 and 38, are illustrated as being substantially coextensive with each other. In such an embodiment, the first length 44 of the first layer 36 can be substantially the same as the second length 60 of the second layer 38. The first width 46 of the first layer 36 can be substantially the same as the second width 62 of the second layer 38. In the exemplary illustration of FIG. 3, about 100% of the first surface 56 of the first layer 36 can be in a face to face relationship with the second surface 74 of the second layer 38. As described herein, a withdrawal aid 14 and a cover 138 can be associated with the fleece 30.

In an embodiment, the fleece 30 can have a multi-layer absorbent structure 34 in which one of the layers, 36 or 38, can have a length and/or width different from the other layer, 36 or 38. Referring to FIGS. 4-8, non-limiting examples of embodiments of absorbent structures 34 are illustrated in which one layer, 36 or 38, can have a length and/or width different from the other layer, 36 or 38.

Figure 4:
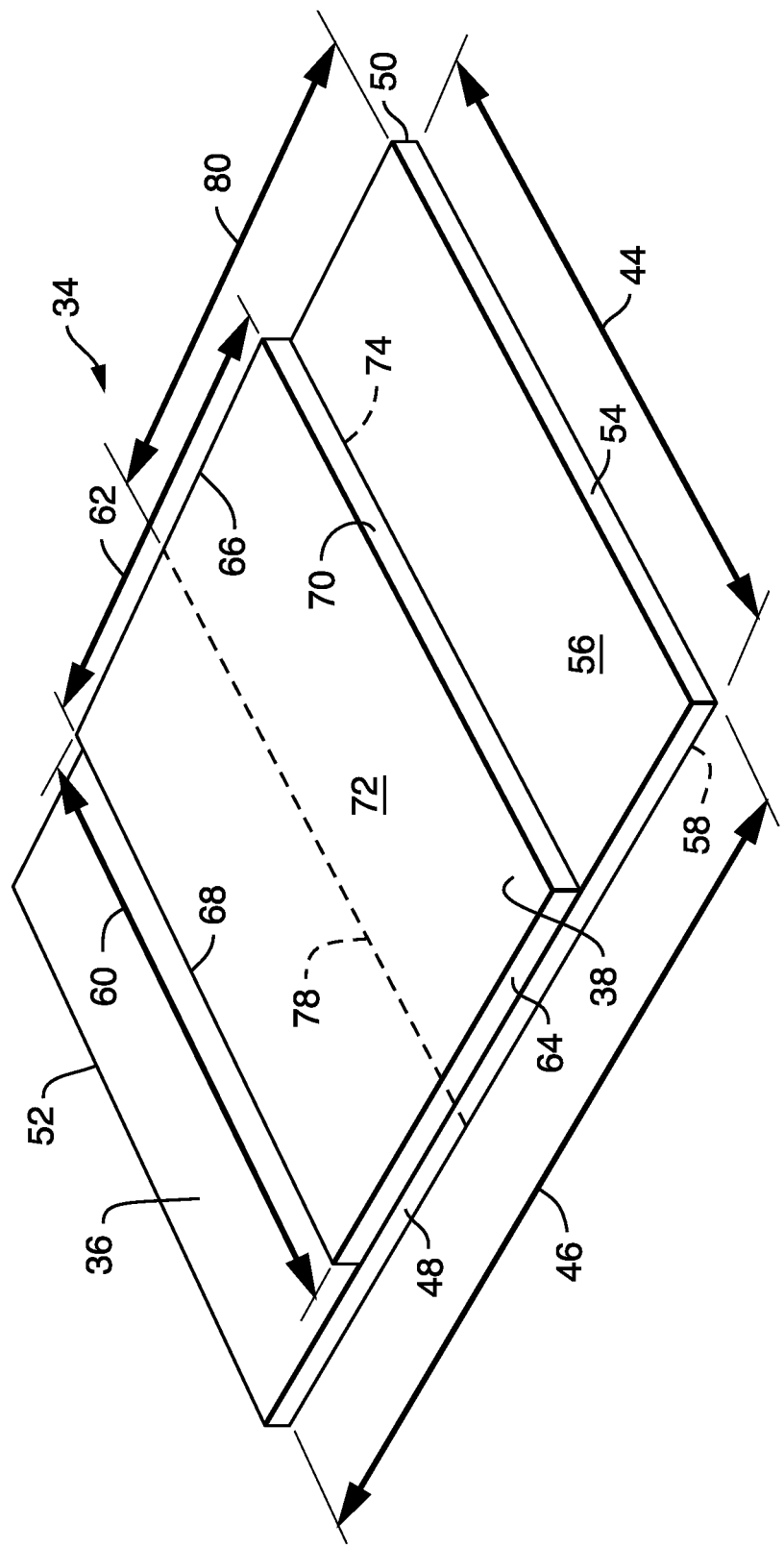
FIG. 4 is a perspective view of an embodiment of an absorbent structure.

FIG. 4 provides an illustration of a non-limiting example of an embodiment of a multi-layer absorbent structure 34 in which the first layer 36 can have a first width 46 greater than the second width 62 of the second layer 38. As illustrated in FIG. 4, the first length 44 of the first layer 36 can be substantially similar to the second length 60 of the second layer 38. In the non-limiting example illustrated in FIG. 4, the second layer 38 can be bonded to the central region of the first width 46 of the first layer 36. The central region of the first width 46 can be the area adjacent a center line 78 of the first width 46 of the first layer 36 of the absorbent structure 34. It is to be understood that the central region of the first width 46 does not need to be the exact center of the first layer 36, but can be located generally around the center line 78 of the first width 46. In an embodiment, the central region of the first width 46 of the first layer 36 can be a position along the first width 46 which is a distance 80 that is about 0.35 to about 0.65 times the first width 46, as measured from either longitudinal edge, 52 or 54, of the first layer 36. It is to be understood that the second layer 38 does not have to be bonded to the first layer 36 in the central region of the first width 46, but rather could be bonded to the first layer 36 in an area adjacent to one of the longitudinal edges, 52 or 54, or at any other position along the first width 46 of the first layer 36 as deemed suitable.

Figure 5:
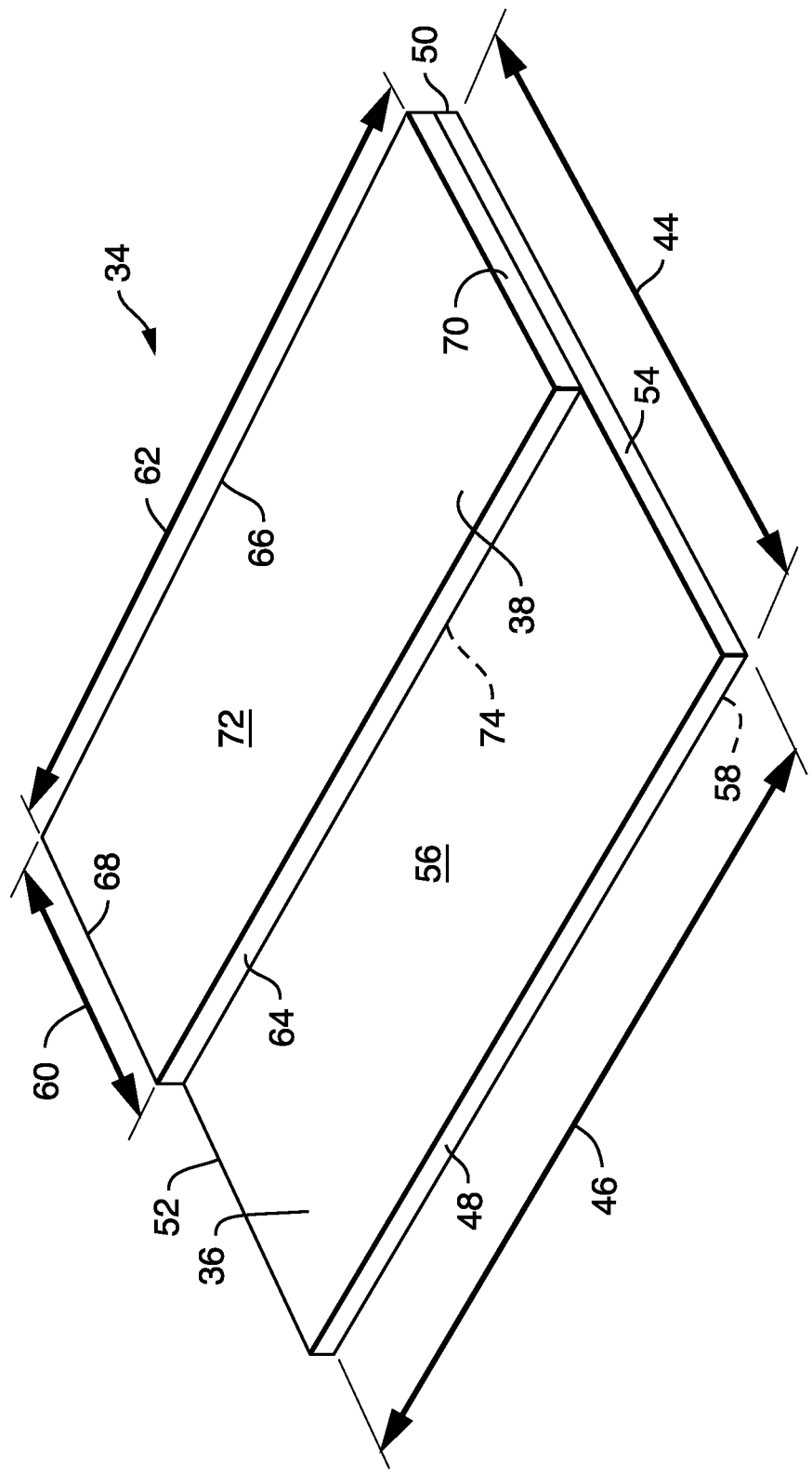
FIG. 5 is a perspective view of an embodiment of an absorbent structure.

FIG. 5 provides an illustration of a non-limiting example of an embodiment of a multi-layer absorbent structure 34 in which the first layer 36 can have a first length 44 greater than the second length 60 of the second layer 38. As illustrated in FIG. 5, the first width 46 of the first layer 36 can be substantially similar to the second width 62 of the second layer 38. In the non-limiting example illustrated in FIG. 5, the second layer 38 can be bonded adjacent to one of the transverse edges, 48 or 50, such as transverse edge 50, of the first layer 36. It is to be understood that the second layer 38 can be bonded to the first layer 36 at any position along the first length 44 of the first layer 36 as deemed suitable.

Figure 6:
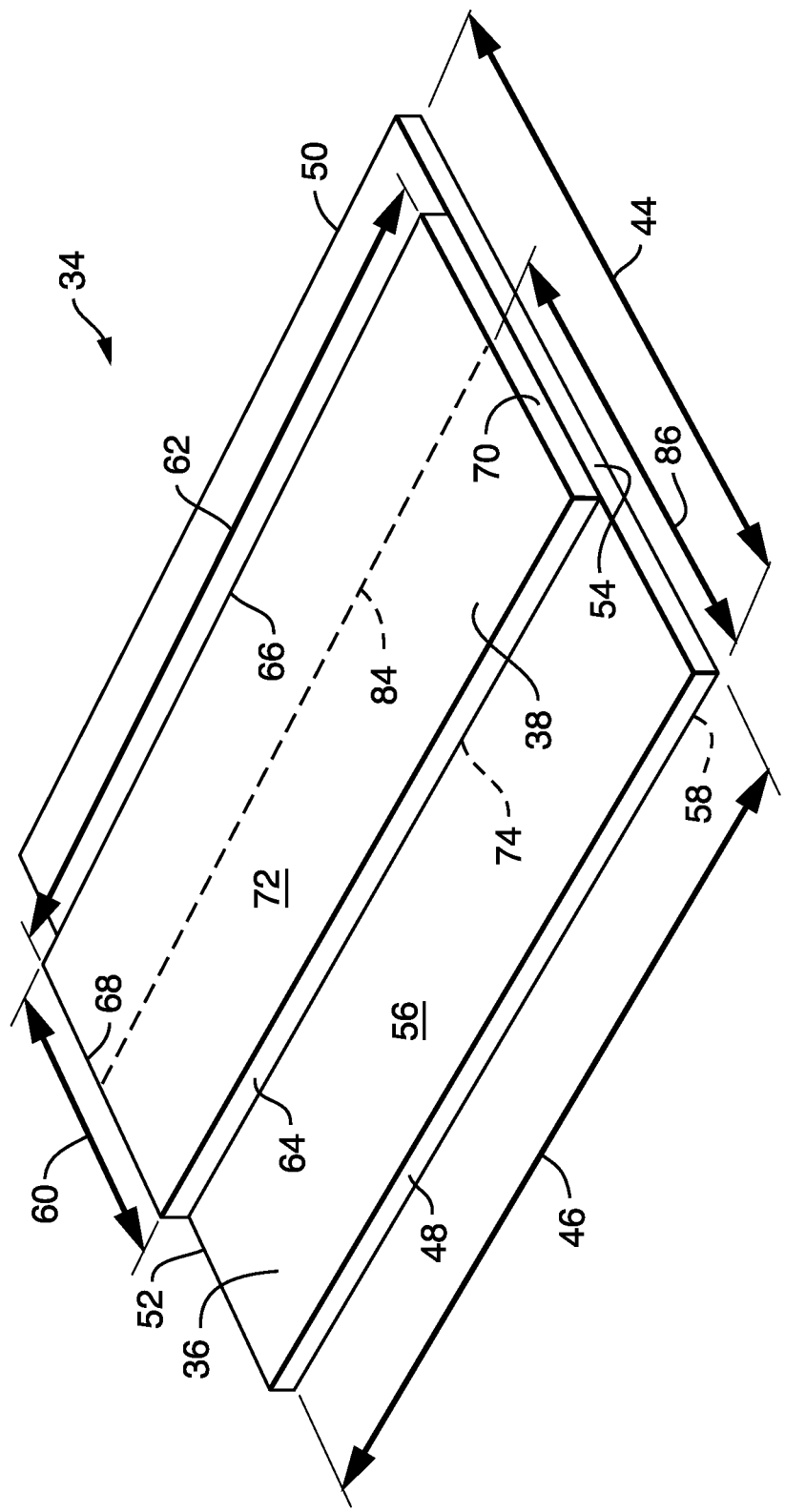
FIG. 6 is a perspective view of an embodiment of an absorbent structure.

FIG. 6 provides an illustration of a non-limiting example of an embodiment of an absorbent structure 34 in which the first layer 36 can have a first length 44 greater than the second length 60 of the second layer 38. As illustrated in FIG. 6, the first width 46 of the first layer 36 can be substantially similar to the second width 62 of the second layer 38. In the non-limiting example illustrated in FIG. 6, the second layer 38 can be bonded in the central region of the first length 44 of the first layer 36. The central region of the first length 44 can be the area adjacent a center line 84 of the first length 44 of the first layer 36 of the absorbent structure 34. It is to be understood that the central region of the first length 44 does not need to be the exact center of the first layer 36, but can be located generally around the center line 84 of the first length 44. In an embodiment, the central region of the first layer 36 can be a position along the first length 44 which can be a distance 86 that can be about 0.35 to about 0.65 times the first length 44, as measured from either transverse edge, 48 or 50, of the first layer 36. In an embodiment, the second layer 38 does not have to be bonded to the first layer 36 in the central region of the first length 44, but rather could be bonded to the first layer 36 in an area adjacent to one of the transverse edges, 48 or 50, or at any other position along the first length 44 of the first layer 36 as deemed suitable.

Figure 7:
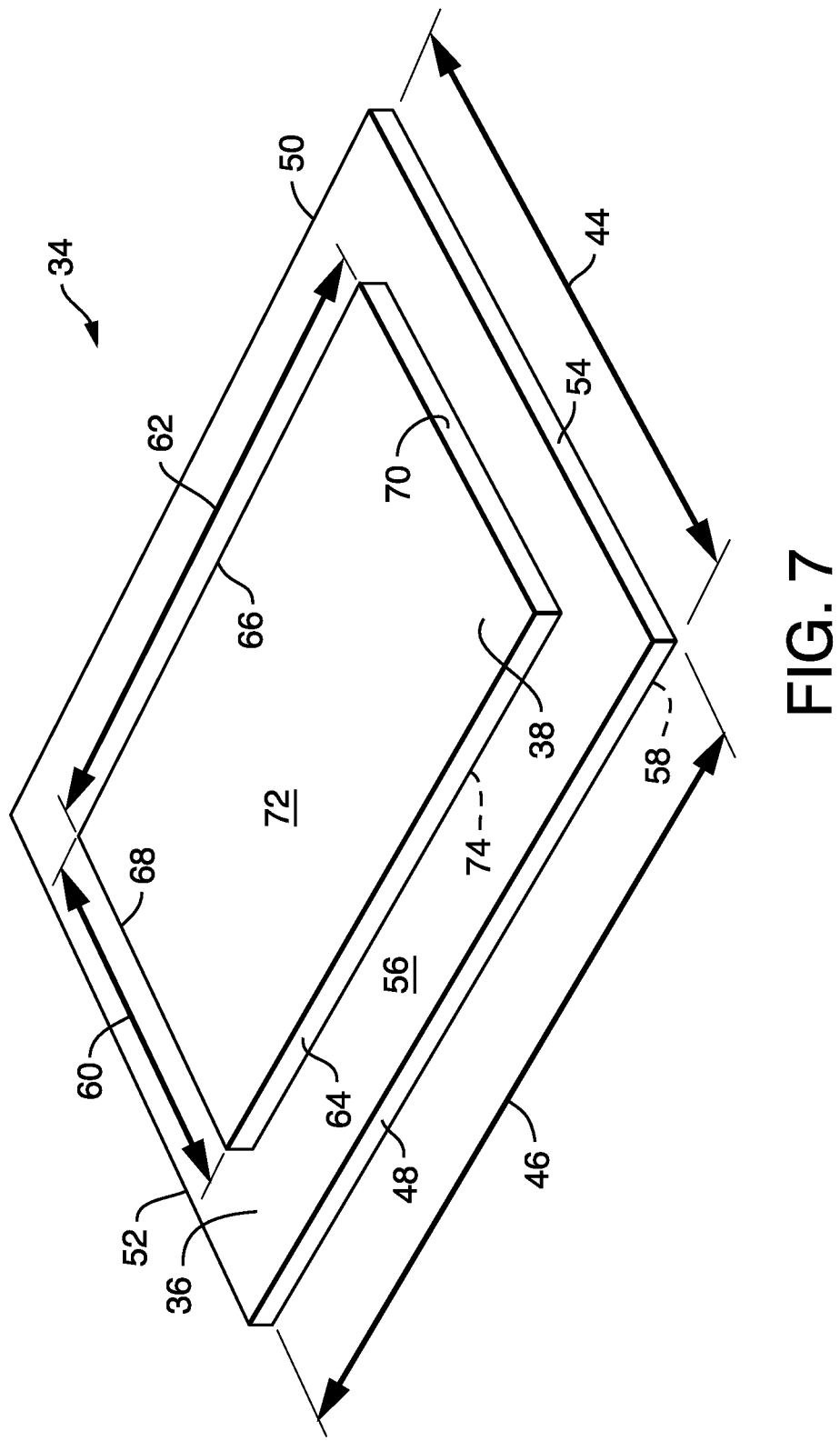
FIG. 7 is a perspective view of an embodiment of an absorbent structure.

FIG. 7 provides an illustration of a non-limiting example of an embodiment of an absorbent structure 34 in which the first layer 36 is illustrated as having a first length 44 and a first width 46 that are each greater than the second length 60 and the second width 62 of the second layer 38.

Figure 8:
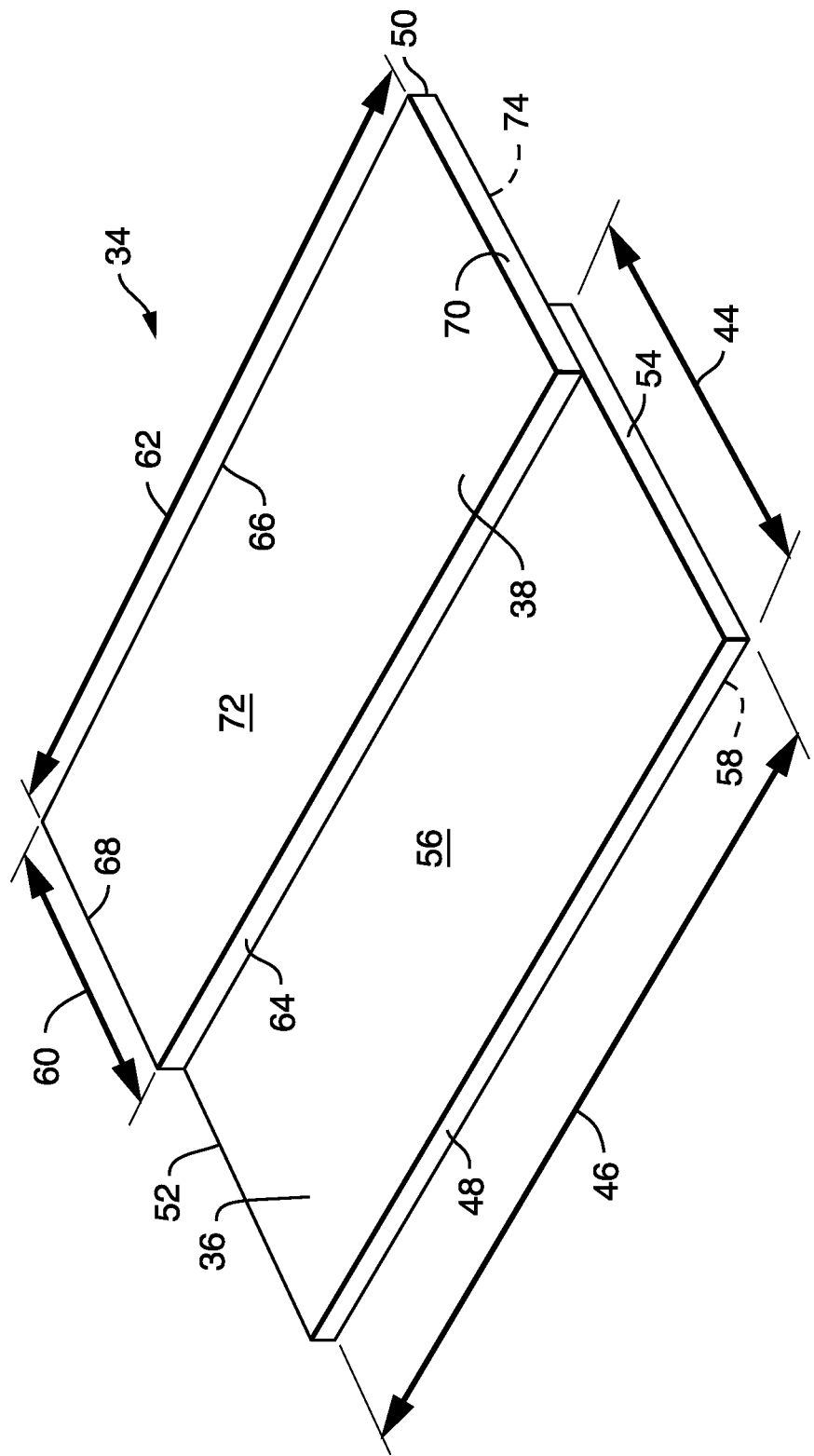
FIG. 8 is a perspective view of an embodiment of an absorbent structure.

FIG. 8 provides an illustration of a non-limiting example of an absorbent structure 34 in which less than 100% of surface 74 of second layer 38 can be in a face to face relationship with surface 56 of first layer 36. First width 46 can be substantially similar to second width 62, however it should be realized that first width 46 can be greater than or less than second width 62. First length 44 can be greater than, less than, or substantially similar to second length 60.

In an embodiment in which a layer, such as layer 36 or 38, has a length and/or width smaller than a length and/or width of another layer, such as layer 36 or 38, the layer with the smaller dimension can be bonded to the layer with the larger dimension in any location as deemed suitable.

Figure 9:
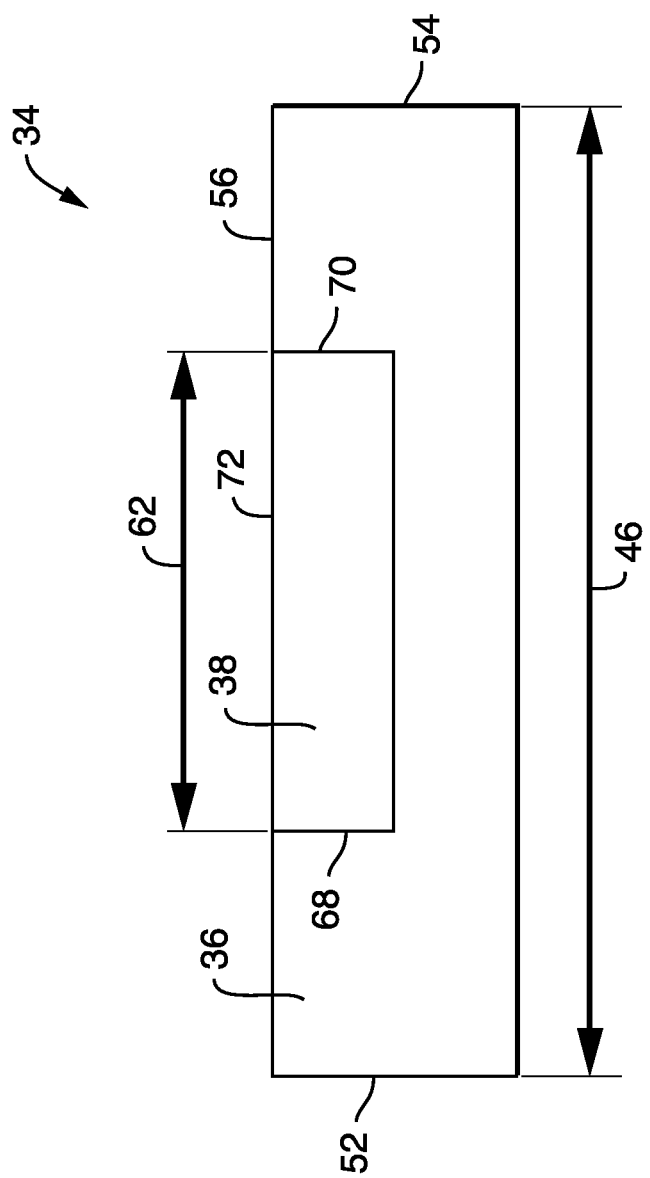
FIG. 9 is a side view of an embodiment of an absorbent structure.

FIGS. 4-8 provide non-limiting illustrations in which the second layer 38 can be positioned on top of the first layer 36. In an embodiment, the first layer 36 can be positioned on top of the second layer 38. In an embodiment, at least a portion of a layer, such as layer 36 or 38, can be inset into another layer, such as layer 36 or 38. In an embodiment, all of a layer, such as layer 36 or 38, can be inset into another layer, such as layer 36 or 38. FIG. 9 provides a non-limiting example of an embodiment of an absorbent structure 34 in which at least a portion of the second layer 38 can be at least partially inset into the first layer 36.

As described herein, each layer, such as layers 36 and 38, can have transverse edges, such as transverse edges 48 and 50 of layer 36 and transverse edges 64 and 66 of layer 38. In an embodiment, each transverse edge(s), 48, 50, 64 and/or 66, can be linear, non-linear, arcuate, and any combination thereof as deemed suitable. Such an edge can be produced in any manner as deemed suitable, such as, but not limited to, knife cutting, die cutting, or any other method known to one skilled in the art. As described herein, a transverse edge can be located at the insertion end 18, the withdrawal end 20 or a location between the insertion and withdrawal ends, 18 and 20, of a resultant tampon 10.

In an embodiment, at least one layer, such as layer(s) 36 and/or 38, of the absorbent structure 34 can have at least one contact element 88. Without being bound by theory, it is believed that when the tampon 10 is in use the contact element 88 can at least partially expand outwardly from the tampon 10 when contacted by bodily fluids. It is believed that such expansion of the contact element 88 can reduce or prevent leakage of bodily fluids from the woman's vagina.

In an embodiment, a tampon 10 can have at least one contact element 88 located at the insertion end 18 of the tampon 10. In an embodiment, a tampon 10 can have at least one contact element 88 located at the withdrawal end 20 of the tampon. In an embodiment, a tampon 10 can have at least one contact element 88 located at both the insertion end 18 and the withdrawal end 20 of the tampon 10. In an embodiment, a tampon 10 can have at least one contact element 88 at a location of the tampon 10 between the insertion end 18 and the withdrawal end 20. In an embodiment, a tampon 10 can have at least one contact element 88 at a location of the tampon 10 between the insertion end 18 and the withdrawal end 20 and at least one contact element 88 located at least one of the insertion end 18 and/or the withdrawal end 20 of the tampon 10.

Figure 10:
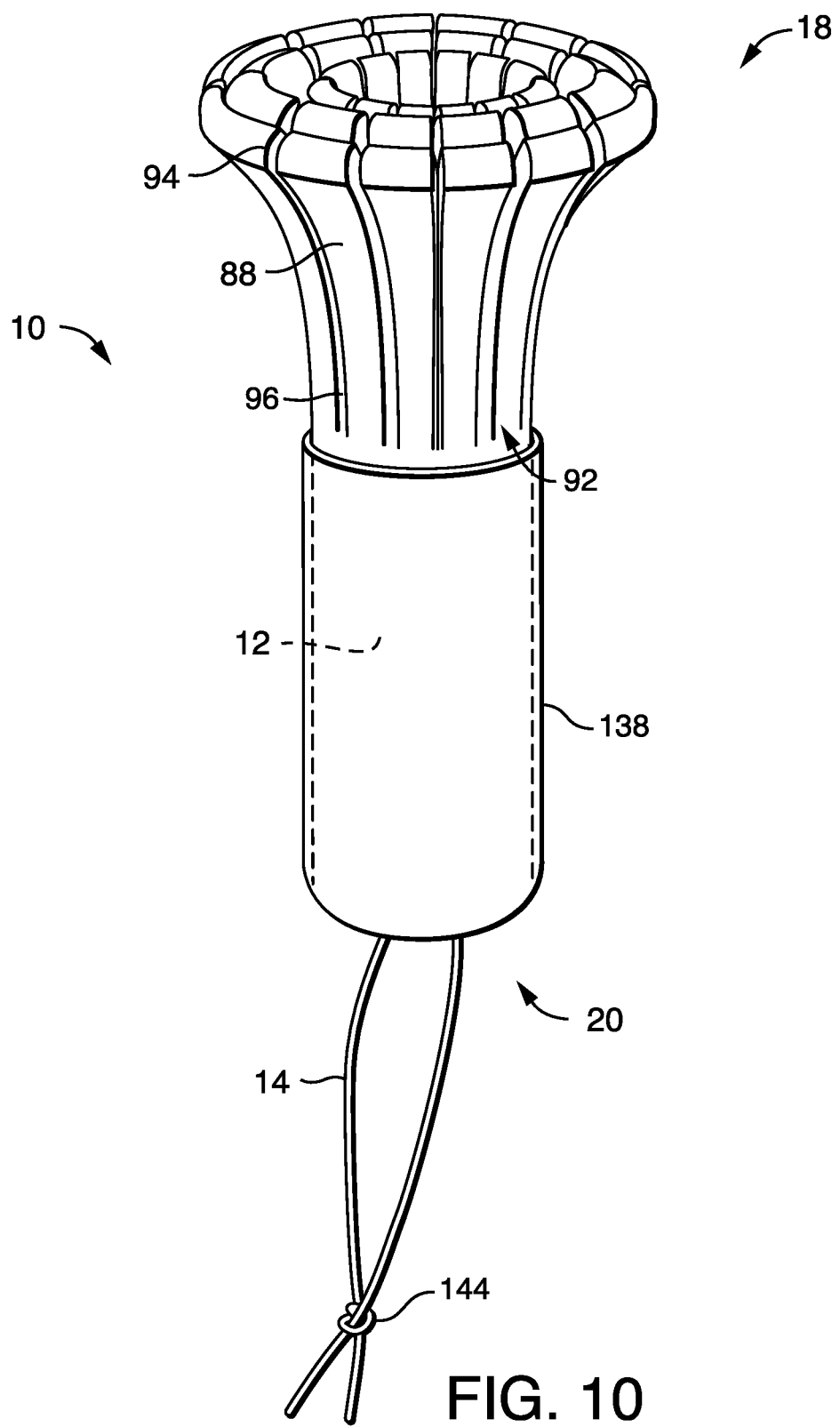
FIG. 10 is a perspective view of an embodiment of a tampon in an activated configuration.

In an embodiment, a contact element 88 can at least partially expand outwardly from the tampon 10 when contacted by body fluids. Without being bound by theory, it is believed that, while the entire tampon 10 may expand from a compressed configuration into a less compressed configuration when contacted by body fluids, when a contact element 88 is contacted by body fluids and at least partially expands away from the tampon 10 as a result of such contact, the expansion of a contact element 88 away from the tampon 10 can result in an expanded contact element 88 region having a cross-sectional diameter that is greater than a cross-sectional diameter of the remaining expanded tampon 10. FIG. 1 provides a non-limiting illustration of a compressed tampon 10 of the current disclosure. As illustrated in FIG. 1, the tampon 10 can have at least one contact element 88 located at the insertion end 18 of the tampon 10. FIG. 10 provides a non-limiting example of an activated tampon 10, i.e., an expanded tampon 10, wherein the contact elements 88 can expand away from the tampon 10 and the region of the contact elements 88 can have a greater cross-sectional diameter than the remainder of the tampon 10. As a contact element 88 expands outwardly from the tampon 10, the contact element 88 can deform and follow the folds and convolutions of the walls of the vaginal cavity in order to respond locally to the changes in the vaginal environment.

A contact element 88 can have a base 92. In an embodiment, a base 92 of at least one contact element 88 can be located at the insertion end 18 of a tampon 10. In an embodiment, a base 92 of at least one contact element 88 can be located at the withdrawal end 20 of a tampon 10. In an embodiment, a base 92 of at least one contact element 88 can be located at the insertion end 18 of a tampon 10 and a base 92 of at least one contact element 88 can be located at the withdrawal end 20 of a tampon 10. In an embodiment, a base 92 of at least one contact element 88 can be at a location between the insertion end 18 and the withdrawal end 20 of a tampon 10. In an embodiment, a base 92 of at least one contact element 88 can be at a location between the insertion end 18 and the withdrawal end 20 of a tampon 10 and a base 92 of a contact element 88 can be located at least one of the insertion end 18 and/or the withdrawal end 20 of a tampon 10.

In an embodiment, a contact element 88 can be at least partially bounded by a free edge 94 and at least partially bounded by a base 92. In an embodiment, a portion of a free edge 94 of a contact element 88 can at least partially align with the insertion end 18 of a tampon 10. In an embodiment, a portion of a free edge 94 of a contact element 88 can at least partially align with the withdrawal end 20 of a tampon 10. In an embodiment, substantially all of the contact element 88 can be located between the insertion end 18 and the withdrawal end 20 of a tampon 10. In an embodiment, a portion of a free edge 94 of a contact element 88 can be at least partially aligned with the insertion end 18 of a tampon 10 and a portion of a free edge 94 of a contact element 88 can be at least partially aligned with the withdrawal end 20 of a tampon 10. In an embodiment, substantially all of a contact element 88 can be located between the insertion end 18 and the withdrawal end 20 and a portion of a free edge 94 of a contact element 88 can be at least partially aligned with at least one of the insertion end 18 and/or the withdrawal end 20 of a tampon 10.

In an embodiment, at least one contact element 88 can be oriented towards the insertion end 18 of the tampon 10. In an embodiment, at least one contact element 88 can be oriented towards the withdrawal end 20 of the tampon 10. In an embodiment, at least one contact element 88 can be oriented towards the insertion end 18 of the tampon 10 and at least one contact element 88 can be oriented towards the withdrawal end 20 of the tampon 10.

In an embodiment, each layer, such as layer 36 and 38, can have at least one contact element 88 located at the insertion end 18, the withdrawal end 20, or at a location between the insertion end 18 and the withdrawal end 20 of a tampon 10. In such an embodiment, a contact element 88 of a layer, such as layer 36, can be, but does not have to be, located in the same location (i.e., insertion end 18, withdrawal end 20, or a location between the insertion end 18 and the withdrawal end 20) as a contact element 88 of another layer, such as layer 38. In an embodiment, each layer, such as layer 36 and 38, can have at least one contact element 88 located at the insertion end 18 of a tampon 10. In an embodiment, each layer, such as layer 36 and 38, can have at least one contact element 88 located at the withdrawal end 20 of a tampon 10. In an embodiment, one of the layers, such as layer 36 or 38, can have at least one contact element 88 located at the insertion end 18 of a tampon 10 and another layer, such as layer 36 or 38, can have at least one contact element 88 located at the withdrawal end 20 of the tampon 10. In an embodiment, each of the layers, such as layers 36 and 38, can each have at least one contact element 88 located at each of the insertion end 18 and the withdrawal end 20 of a tampon 10. In an embodiment, one of the layers, such as layer 36 or 38, can have a contact element 88 located at least one of the insertion end 18 and/or the withdrawal end 20 and another layer, such as layer 36 or 38, can have a contact element 88 located at a location between the insertion end 18 and the withdrawal end 20 of a tampon 10.

In an embodiment in which each of the layers, such as layers 36 and 38, have at least one contact element 88, the at least one contact element 88 of each layer, such as layers 36 and 38, can be in any overlapping relationship to each other as desired. In an embodiment, a contact element 88 of layer 36 can substantially overlap a contact element 88 of layer 38. In an embodiment, a contact element 88 of layer 36 can partially overlap a contact element 88 of layer 38. In an embodiment, a contact element 88 of layer 36 can have minimal or no overlap with a contact element 88 of layer 38.

In an embodiment, at least one of the layer(s), such as layer(s) 36 and/or 38, can have at least one contact element 88. In an embodiment, at least one of the layer(s), such as layer(s) 36 and/or 38, can have at least 1, 2, 3, 4, 5, 6, 7, 8, 9, or 10 contact elements 88. In an embodiment, at least one of the layer(s), such as layer(s) 36 and/or 38, can have from 1, 2, 3, 4, 5, 6, 7, 8, 9, or 10 to 11, 12, 13, 14, 15, 16, 17, 18, 19, or 20 contact elements 88. In an embodiment, each of the layers, such as layers 36 and 38, can each have at least one contact element 88. In an embodiment, each of the layers, such as layers 36 and 38, can have at least 1, 2, 3, 4, 5, 6, 7, 8, 9, or 10 contact elements 88. In an embodiment, each of the layers, such as layers 36 and 38, can have from 1, 2, 3, 4, 5, 6, 7, 8, 9, or 10 to 11, 12, 13, 14, 15, 16, 17, 18, 19, or 20 contact elements 88.

In an embodiment, at least one layer(s), such as layer(s) 36 and/or 38, can have at least one contact element 88 at least partially separated from another contact element 88. In an embodiment, the partial separation of one contact element 88 from another contact element 88 can occur via an amplitude of an arc, a slit, or combination thereof.

FIGS. 11-24 illustrate various non-limiting examples of embodiments of an absorbent structure 34 in which at least one layer, such as layer 36 and/or 38, can have at least one contact element 88. It is to be understood that the configurations of absorbent structures 34 and contact elements 88 described and illustrated herein are non-limiting and additional configurations are contemplated by this disclosure.

Figure 11:
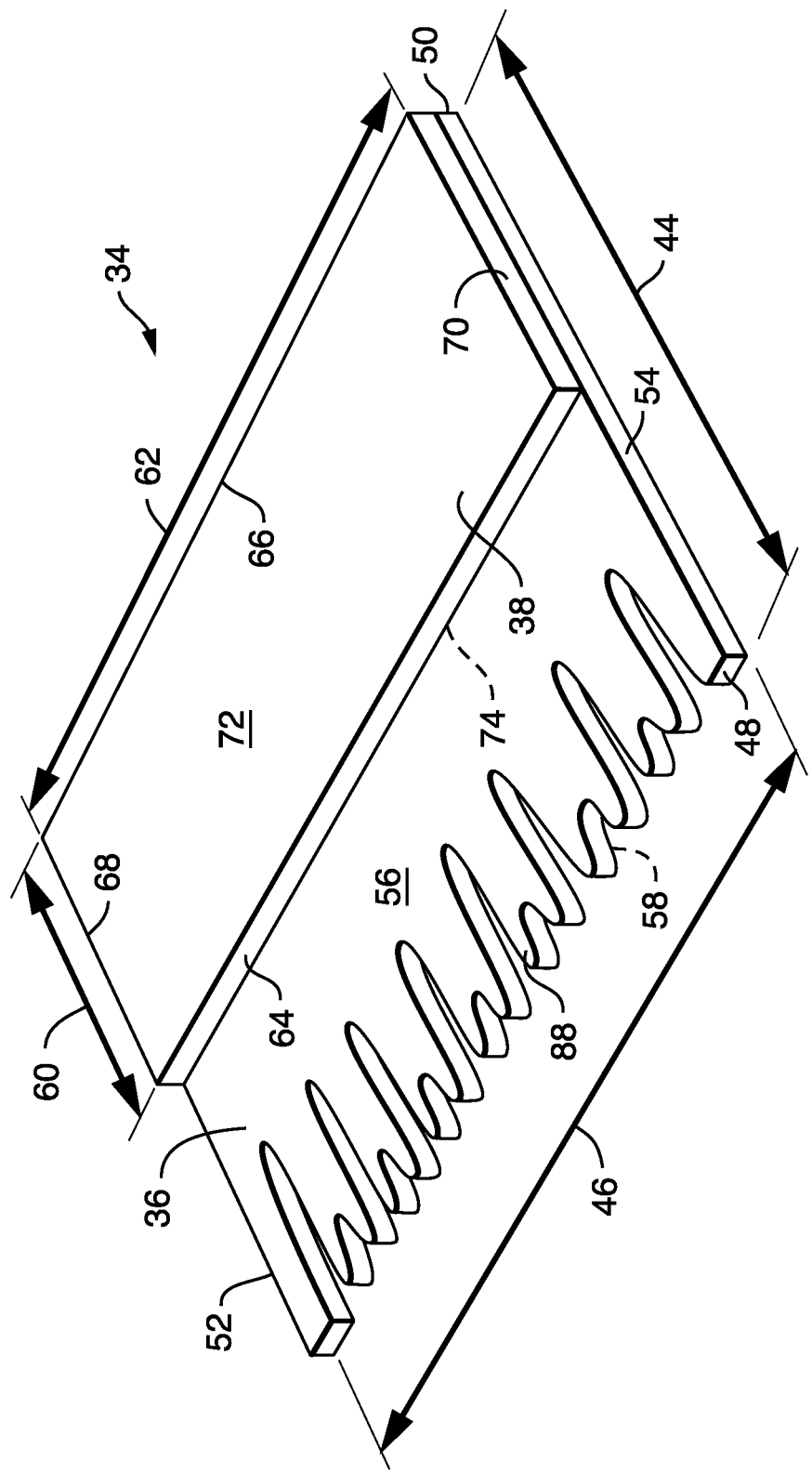
FIG. 11 is a perspective view of an embodiment of an absorbent structure with at least one contact element.

In an embodiment, a layer(s), such as layer 36 and/or 38, of an absorbent structure 34 can have a transverse edge which can have an undulating arcuate pattern. In such an embodiment, the undulating arcuate pattern can produce at least one contact element 88. The amplitude of each arc can be any amplitude as deemed suitable. In such an embodiment, a contact element 88 can be at least partially separated from another contact element 88 by the amplitude of the arc. FIG. 11 illustrates a non-limiting example of an absorbent structure 34 which can have two layers, 36 and 38. As illustrated in FIG. 11, layer 36 can have a first width 46 which can be substantially the same as the second width 62 of layer 38. As illustrated in FIG. 11, layer 36 can have a first length 44 which can be longer than a second length 60 of layer 38. Layer 36 can have two transverse edges, 48 and 50, in which transverse edge 48 can have an undulating arcuate pattern. Such an undulating arcuate pattern can produce contact elements 88 which can be at least partially separated from each other by the amplitude of an arc between each contact element 88. In an embodiment, a transverse edge having an arcuate pattern can be located at the insertion end 18 of a resultant tampon 10. In an embodiment, a transverse edge having an arcuate pattern can be located at the withdrawal end 20 of a resultant tampon 10. In an embodiment, a transverse edge having an arcuate pattern can be located at a location between the insertion end 18 and the withdrawal end 20 of a resultant tampon 10. In an embodiment, transverse edges having an arcuate pattern can be located at both the insertion end 18 and the withdrawal end 20 of a resultant tampon 10. In an embodiment, a layer(s), 36 and/or 38, can have a transverse edge having an arcuate pattern at a location between the insertion end 18 and the withdrawal end 20 and a layer(s), 36 and/or 38, can have a transverse edge having an arcuate pattern at least one of the insertion end 18 and/or the withdrawal end 20 of the tampon 10.

In an embodiment, the free edge 94 of a contact element 88 can be generated via a slit 96. A slit 96 can extend through a layer(s), such as layer(s) 36 and/or 38, from a first surface and through to a second surface of the layer(s), such as layer(s) 36 and/or 38. For example, a slit 96 can be incorporated into layer 36, extending from a first surface 56 of layer 36 through to a second surface 58 of layer 36 to form a free edge 94 of a contact element 88. In an embodiment, a layer(s), such as layer(s) 36 and/or 38, can have at least one slit 96. In an embodiment, a layer(s), such as layer(s) 36 and/or 38, can have at least 1, 2, 3, 4, 5, 6, 7, 8, 9, or 10 slits 96. In an embodiment, a layer(s), such as layer(s) 36 and/or 38, can have from about 1, 2, 3, 4, 5, 6, 7, 8, 9, or 10 to about 11, 12, 13, 14, 15, 16, 17, 18, 19, or 20 slits 96. In an embodiment, a layer(s), such as layer(s) 36 and/or 38, can have the appropriate number of slits 96 to provide the desired number of contact elements 88.

In an embodiment, a slit 96 can be linear, arcuate, any other shape, or combination thereof. In an embodiment, a slit 96 can have any length 98 as desired. The length 98 can be measured as the distance between the terminal ends of the slit 96. In an embodiment in which the slit 96 contains an arc, the arc length can be determined by any manner deemed suitable by one of ordinary skill in order to determine the length 98 of the slit 96. In an embodiment, the length 98 of a slit 96 can range from about 1, 2, 3, 4, 5, 6, 7, 8, 9, 10, 11, 12, 13, 14 or 15 mm to about 16, 17, 18, 19, 20, 21, 22, 23, 24, 25, 26, 27, 28, 29 or 30 mm. In an embodiment, the length 98 of a slit 96 can be greater than about 1, 2, 3, 4, 5, 6, 7, 8, 9, 10, 11, 12, 13, 14 or 15 mm. In an embodiment, the length 98 of a slit 96 can be less than about 30, 29, 28, 27, 26, 25, 24, 23, 22, 21, 20, 19, 18, 17, 16, or 15 mm.

In an embodiment in which a layer, such as layer 36 or 38, has more than one slit 96, each slit 96 can have the same length 98. In an embodiment in which a layer, such as layer 36 or 38, has more than one slit 96, a slit 96 can have a length 98 that differs from the length 98 of at least one other slit 96. In an embodiment, at least about 20, 25, 40, 45, 50, 55, 70, 75, 80 or 85% of the slits 96 in a layer, such as layer 36 or 38, can have substantially the same length 98. In an embodiment, about 25, 50, or 75% of the slits in a layer, such as layer 36 or 38, can have substantially the same length, such as a first slit length, and about 25, 50, or 75% of the slits in the same layer, such as layer 36 or 38, can have substantially the same length, such as a second slit length, and the second slit length can be different from the first slit length. In an embodiment in which the slits 96 incorporated into a layer, such as layer 36 or 38, have varying slit lengths, the slits 96 can be incorporated into the layer, such as layer 36 or 38, in any pattern of slit lengths as desired.

In an embodiment, an absorbent structure 34 can have two layers, such as layers 36 and 38, in which each layer, such as layers 36 and 38, can have more than one slit 96. In an embodiment, each slit 96 in the absorbent structure 34 can have the same length 98. In an embodiment, the absorbent structure 34 can have a slit 96 that can have a length 98 that differs from the length 98 of at least one other slit 96 located within the absorbent structure 34. In an embodiment, at least about 20, 25, 40, 45, 50, 55, 70, 75, 80 or 85% of the slits 96 in the absorbent structure 34 can have substantially the same length 98. In an embodiment, about 25, 50, or 75% of the slits 96 in the absorbent structure 34 can have substantially the same length, such as a first slit length, and about 25, 50, or 75% of the slits 96 in the absorbent structure 34 can have substantially the same length, such as a second slit length, and the second slit length can be different from the first slit length. In an embodiment in which the slits 96 incorporated into the absorbent structure 34 have varying slit lengths, the slits 96 can be incorporated into the absorbent structure 34 in any pattern of slit lengths as desired.

In an embodiment, a slit 96 can be incorporated into at least one layer(s), such as layer(s) 36 and/or 38, when the layer(s), such as layer(s) 36 and/or 38, is in a flat, unfolded configuration or when the layer(s), such as layer(s) 36 and/or 38, has a folded configuration. In an embodiment, a slit 96 can be a continuous or intermittent cut. In an embodiment, a slit 96 can be a line of weakness.

In an embodiment, a slit 96 can be incorporated into a layer(s), such as layer(s) 36 and/or 38, in any location of the layer(s), such as layer(s) 36 and/or 38, as deemed suitable. For example, a slit 96 can be incorporated into a layer(s), such as layer(s) 36 and/or 38, between the transverse edges of the layer(s), such as layer(s) 36 and/or 38, in association with a transverse edge of the layer(s), such as layer(s) 36 and/or 38, and combinations thereof.

In an embodiment, a slit 96 can be incorporated into at least one layer(s), such as layer(s) 36 and/or 38, and can be located in any desired location between the transverse edges of the layer(s), such as layer(s) 36 and/or 38. In such an embodiment, the slit 96 need not be associated with transverse edges of the layer(s), such as layer(s) 36 and/or 38. In such an embodiment, the slit 96 can be linear, arcuate, any other shape as desired, or combination thereof and can have any length 98 as desired. In such an embodiment, more than one slit 96 can be incorporated into the at least one layer(s), such as layer(s) 36 and/or 38, and each slit 96 can be separated from any other slit 96 by any distance as deemed suitable. In such an embodiment, the slit 96 can create a contact element 88 that can be at least partially bounded by a free edge 94 and at least partially bounded by a base 92.

Figure 12:
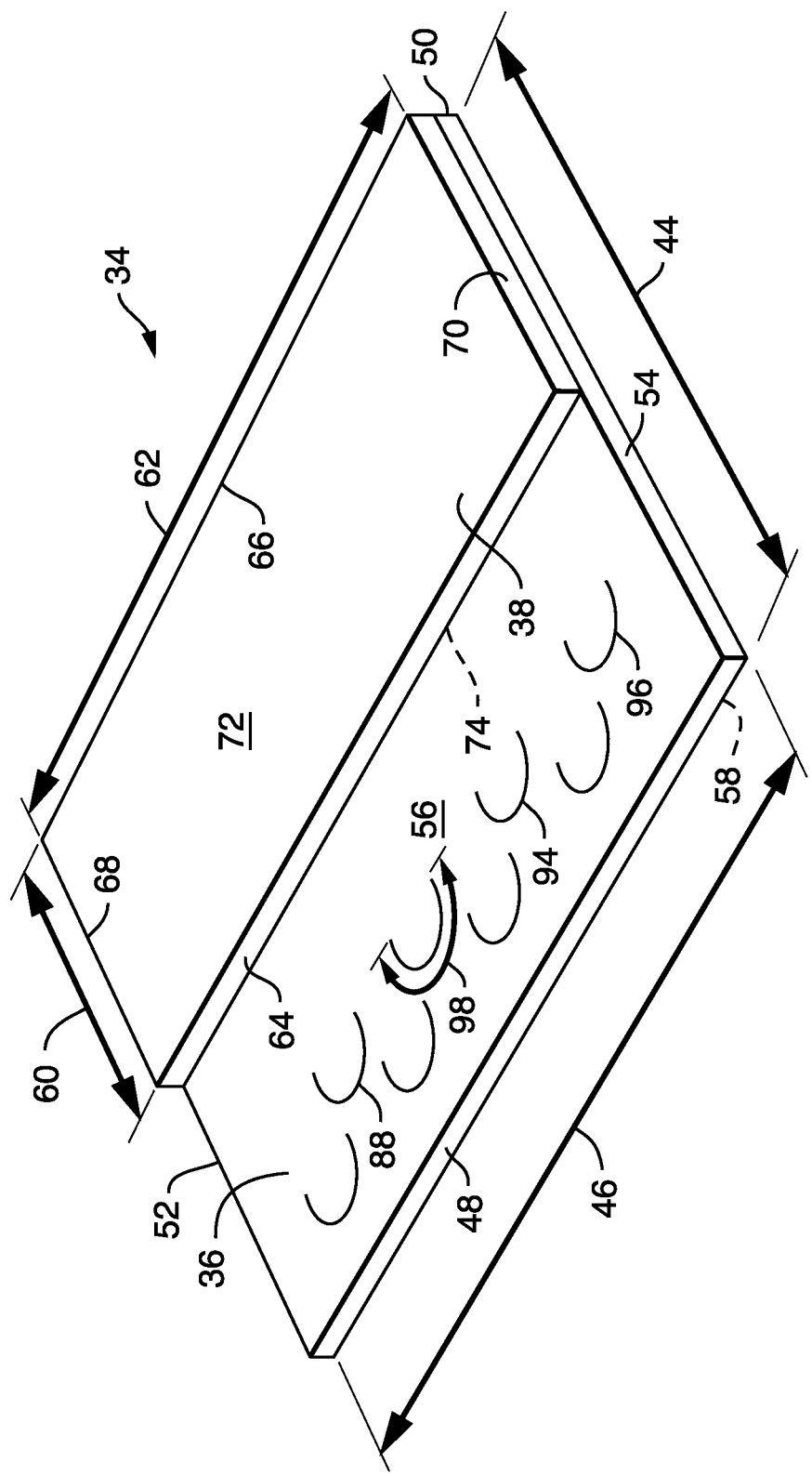
FIG. 12 is a perspective view of an embodiment of an absorbent structure with at least one contact element.

FIG. 12 provides a non-limiting example of an absorbent structure 34 which can have two layers, 36 and 38. The first layer 36 of the absorbent structure 34 can have a first length 44 which can be greater than the second length 60 of the second layer 38. The first width 46 of the first layer 36 can be substantially similar to the second width 62 of the second layer 38. The first layer 36 can have two transverse edges, 48 and 50, and the second layer 38 can have two transverse edges, 64 and 66. In the non-limiting example, transverse edge 66 of the second layer 38 can be substantially aligned with transverse edge 50 of the first layer 36. In the non-limiting illustration of FIG. 12, first layer 36 can have at least one slit 96 located between transverse edges 48 and 50 of layer 36. The slits 96 can extend from a first surface 56 of the first layer 36 through to a second surface 58 of the first layer 36. The slits 96 can be in any configuration as desired, such as, for example, an arcuate configuration. It should be realized that the slits 96 can have any length 98 as desired and can be spaced apart from each other any distance as desired. As described herein, transverse edge 48 can be located at the insertion end 18 or the withdrawal end 20 of a resultant tampon 10. In an embodiment, the contact elements 88 of the absorbent structure 34 illustrated in FIG. 12 can be located at the insertion end 18 or the withdrawal end 20 of a resultant tampon 10. In the non-limiting embodiment illustrated in FIG. 12, the contact elements 88 can be oriented towards the insertion end 18 or the withdrawal end 20 of a resultant tampon 10. In an embodiment, a slit 96 can also be incorporated into second layer 38.

In an embodiment, a slit 96 can be associated with a transverse edge of a layer, such as, for example, transverse edge 48 of layer 36, and can extend from the transverse edge 48 in a direction towards the interior region of the layer, such as, for example, the interior region of layer 36. In such an embodiment, the slit 96 can extend from the transverse edge 48 of layer 36 in a direction towards the opposite transverse edge, edge 50, of layer 36. As described herein, in an embodiment, a slit 96 need not be associated with a transverse edge of a layer, such as transverse edge 48 of layer 36.

In an embodiment, such as, for example, an embodiment in which more than one slit 96 can be associated with a transverse edge of a layer, such as layer 36 or 38, a width 102 (illustrated in FIG. 13) can separate a slit 96 from the next successive slit 96. The width 102 can be any distance as deemed suitable. In an embodiment, the width 102 can range from about 1, 2, 3, 4, 5, 6 or 7 mm to about 8, 9, 10, 11, 12, 13, 14 or 15 mm. In an embodiment in which slits 96 are associated with a transverse edge of a layer, such as layer 36 or 38, as described herein, the width 102 can be the width of a contact element 88. Two successive slits 96 associated with a transverse edge can create a contact element 88.

FIG. 13-24 illustrate various embodiments of slits 96 incorporated into at least one layer, 36 and/or 38, of an absorbent structure 34 and associated with a transverse edge. As shown in the non-limiting examples of FIG. 13-24, the slits 96 can be incorporated into a layer(s), 36 and/or 38, such as, for example, by being cut through from a first surface to a second surface of at least one layer, such as layer 36 and/or 38. While particular embodiments are illustrated and described, it is to be understood that various changes and modifications can be made to the embodiments illustrated and described without departing from the spirit and scope of the disclosure.

Figure 13:
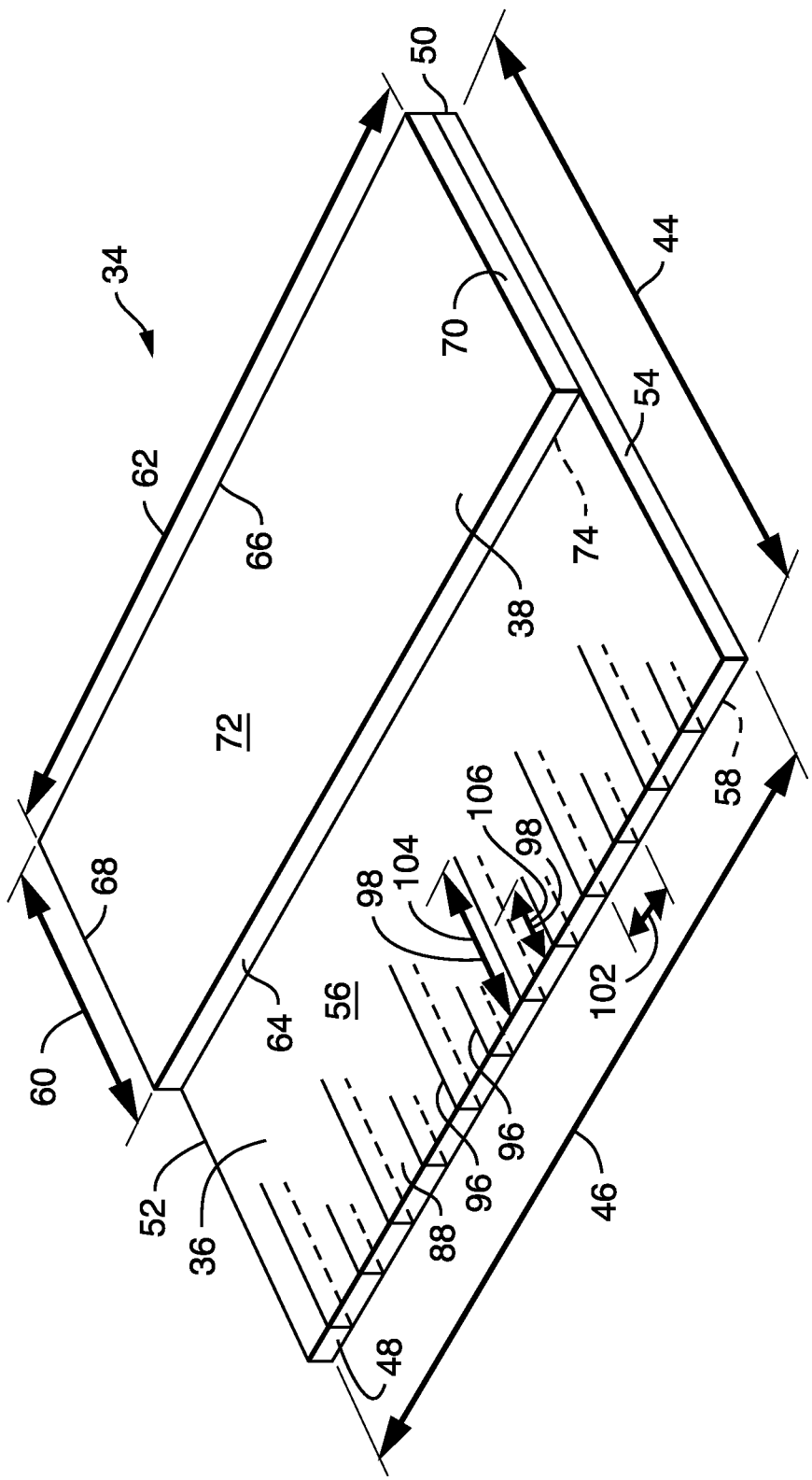
FIG. 13 is a perspective view of an embodiment of an absorbent structure with at least one contact element.

FIG. 13 provides a non-limiting example of an absorbent structure 34 which can have two layers, 36 and 38. The first layer 36 of the absorbent structure 34 can have a first length 44 which can be greater than the second length 60 of the second layer 38. The first width 46 of the first layer 36 can be substantially similar to the second width 62 of the second layer 38. The first layer 36 can have two transverse edges, 48 and 50, and the second layer 38 can have two transverse edges, 64 and 66. In the non-limiting example, transverse edge 66 of the second layer 38 can be substantially aligned with transverse edge 50 of the first layer 36. In the non-limiting illustration of FIG. 13, first layer 36 can have at least one slit 96 associated with transverse edge 48. The first layer 36 can have at least two successive slits 96 associated with transverse edge 48 and the two successive slits 96 can create a contact element 88. The slits 96 can extend from a first surface 56 of the first layer 36 through to a second surface 58 of the first layer 36. The slits 96 can extend from the transverse edge 48 in a direction away from the transverse edge 48 and towards an interior region of the first layer 36 of the absorbent structure 34 such that the slits 96 can extend in a direction toward the opposite transverse edge 50 of the first layer 36. It should be realized that the slits 96 can have any length 98 as desired as the slits 96 extend from transverse edge 48 in a direction towards the opposite transverse edge 50 of the first layer 36. As illustrated in FIG. 13 in a non-limiting embodiment, at least one of the slits 96 can have a first slit length 104 and at least one of the slits 96 can have a second slit length 106 wherein the first slit length 104 and the second slit length 106 are not the same. As illustrated in FIG. 13 in the non-limiting embodiment illustrated, the slits 96 may be incorporated into layer 36 in a pattern of alternating lengths. In an embodiment in which slits 96 having different lengths are incorporated into a layer, such as layer 36 and/or 38, the slits 96 having different lengths can be incorporated into the respective layer such that the different lengths of the slits 96 can be in a random sequence, in an alternating pattern, or in a repeating pattern. As illustrated in FIG. 13, the slits 96 do not necessarily extend the entire first length 44 of the first layer 36. While the second layer 38 is illustrated such that transverse edge 66 can be substantially aligned with transverse edge 50 of the first layer 36, it should be realized that transverse edge 66 of second layer 38 does not need to be substantially aligned with transverse edge 50 of the first layer 36. It should be realized that second layer 38 can be bonded to the first layer 36 at any position along the first length 44 of the first layer 36 as deemed suitable. It should be realized that transverse edge 64 of second layer 38 can also be positioned anywhere along the first length 44 of the first layer 36 as desired and the second length 60 of second layer 38 can be any dimension as desired. In an embodiment, layer 38 can at least partially or completely overlay the contact elements 88 incorporated into layer 36. As described herein, transverse edge 48 can be located at the insertion end 18 or the withdrawal end 20 of a resultant tampon 10. In an embodiment, the contact elements 88 of the absorbent structure 34 illustrated in FIG. 13 can be located at the insertion end 18 or the withdrawal end 20 of a resultant tampon 10. In the non-limiting embodiment illustrated in FIG. 13, the contact elements 88 can be oriented towards the insertion end 18 or the withdrawal end 20 of a resultant tampon 10. In an embodiment, a slit 96 can also be incorporated into second layer 38.

Figure 14:
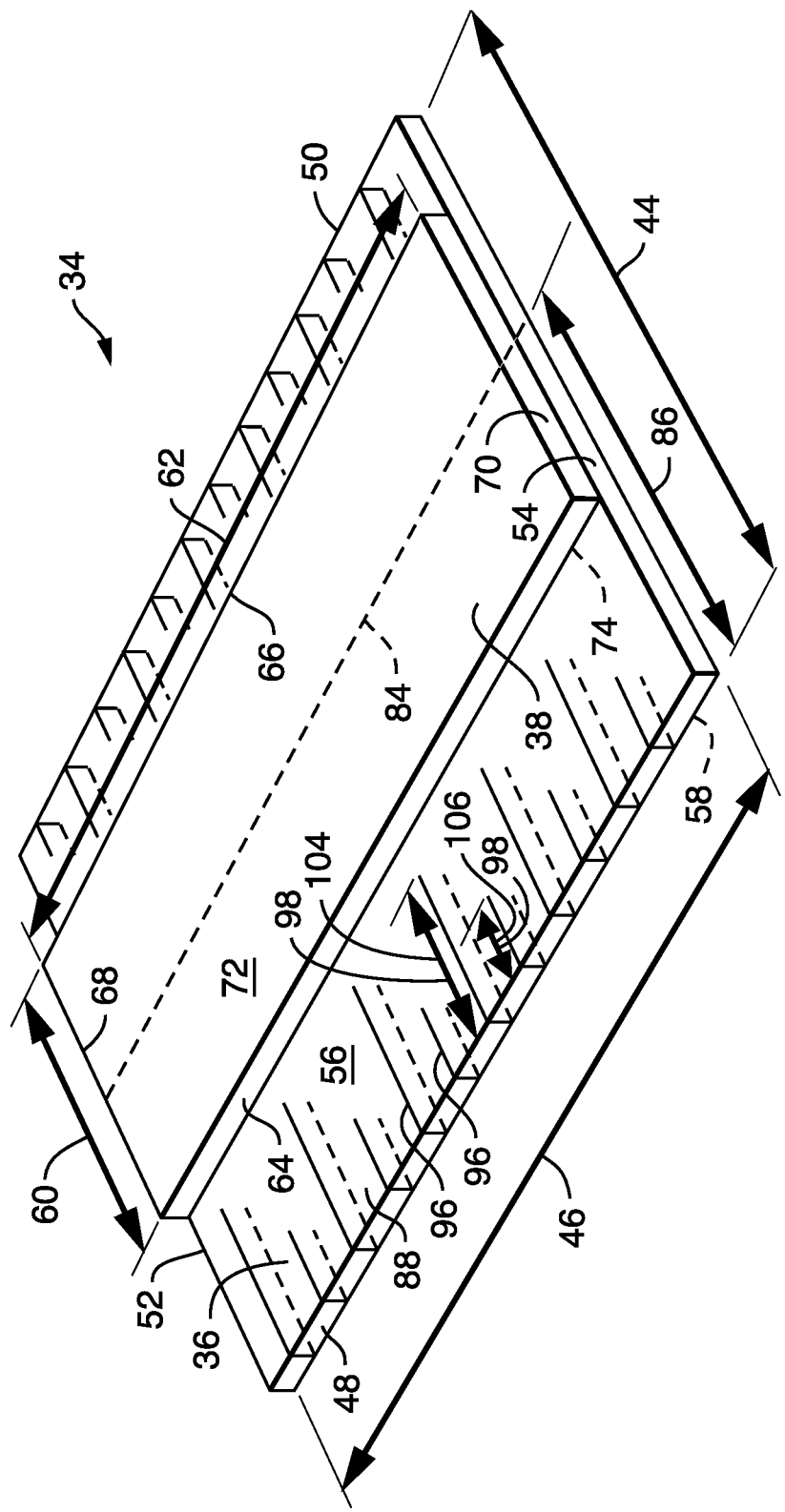
FIG. 14 is a perspective view of an embodiment of an absorbent structure with at least one contact element.

FIG. 14 provides an illustration of a non-limiting example of an embodiment of an absorbent structure 34 in which the first layer 36 can have a first length 44 greater than the second length 60 of the second layer 38. As illustrated in FIG. 14, the first width 46 of the first layer 36 can be substantially similar to the second width 62 of the second layer 38. In the non-limiting example illustrated in FIG. 14, the second layer 38 can be bonded to the first layer 36 in the central region of the first length 44 of the first layer 36. The central region of the first length 44 can be the area adjacent a center line 84 of the first length 44 of the first layer 36 of the absorbent structure 34. It is to be understood that the central region of the first length 44 does not need to be the exact center of the first layer 36, but can be located generally around the center line 84 of the first length 44. In an embodiment, the central region of the first layer 36 can be a position along the first length 44 which can be a distance 86 that can be about 0.35 to about 0.65 times the first length 44, as measured from either transverse edge, 48 or 50, of the first layer 36. In an embodiment, the second layer 38 does not have to be bonded to the first layer 36 in the central region of the first length 44, but rather could be bonded to the first layer 36 in an area adjacent to one of the transverse edges, 48 or 50, or at any other position along the first length 44 of the first layer 36 as deemed suitable. In the non-limiting illustration of FIG. 14, the first layer 36 can have at least one slit 96 associated with each of the transverse edges, 48 and 50, of first layer 36. The first layer 36 can have at least two successive slits 96 associated with transverse edges 48 and 50, respectively, and the two successive slits 96 associated with a transverse edge can create a contact element 88. The slits 96 can extend from a first surface 56 of the first layer 36 through to a second surface 58 of the first layer 36. The slits 96 can extend from the transverse edge, 48 or 50, respectively, in a direction towards an interior region of the first layer 36 of the absorbent structure 34 such that the slits 96 can extend from the associated transverse edge, 48 or 50, and in a direction toward the opposite transverse edge, 48 or 50, respectively, of the first layer 36. It should be realized that the slits 96 can have any length 98 as desired as the slits 96 extend from a transverse edge, 48 or 50, in a direction towards the opposite transverse edge, 48 or 50, of the first layer 36. As illustrated in FIG. 14 in a non-limiting embodiment, at least one of the slits 96 can have a first slit length 104 and at least one of the slits 96 can have a second slit length 106 wherein the first slit length 104 and the second slit length 106 are not the same. As illustrated in FIG. 14 in a non-limiting embodiment, the slits 96 may be incorporated into layer 36 in a pattern of alternating lengths. In an embodiment in which slits 96 having different lengths are incorporated into a layer, such as layer 36 and/or 38, the slits 96 having different lengths can be incorporated into the respective layer such that the different lengths of the slits 96 can be in a random sequence, in an alternating pattern, or in a repeating pattern. As illustrated in FIG. 14, the slits 96 do not necessarily extend the entire first length 44 of the first layer 36. It should be realized that transverse edges, 64 and 66, of second layer 38 can be positioned anywhere along the first length 44 of the first layer 36 as desired and the second length 60 of second layer 38 can be any dimension as desired. In an embodiment, layer 38 can at least partially or completely overlay the contact elements 88 incorporated into layer 36. As described herein, the transverse edges, 48 and 50, can be located at the insertion end 18 and the withdrawal end 20 of a resultant tampon 10. Thus, in an embodiment, the contact elements 88 of the absorbent structure 34 illustrated in FIG. 14 can be located at the insertion end 18 and the withdrawal end 20 of a resultant tampon 10. In the non-limiting embodiment illustrated in FIG. 14, the contact elements 88 can be oriented towards the insertion end 18 and the withdrawal end 20 of a resultant tampon 10. In an embodiment, a slit 96 can also be incorporated into second layer 38.

Figure 15:
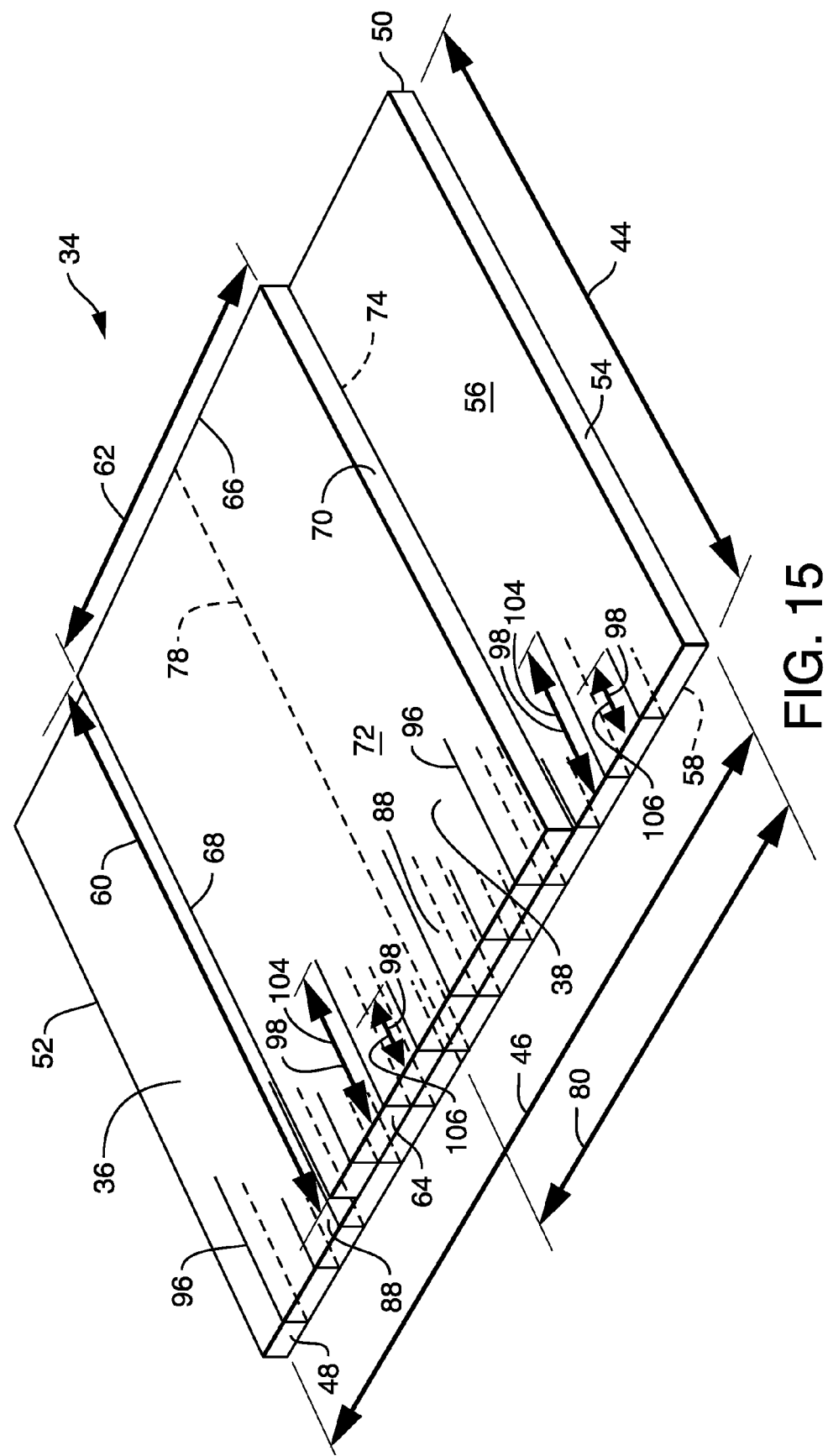
FIG. 15 is a perspective view of an embodiment of an absorbent structure with at least one contact element.

FIG. 15 provides an illustration of a non-limiting example of an embodiment of an absorbent structure 34 in which the first layer 36 can have a first width 46 greater than the second width 62 of the second layer 38. As illustrated in FIG. 15, the first length 44 of the first layer 36 can be substantially similar to the second length 60 of the second layer 38. In the non-limiting example illustrated in FIG. 15, the second layer 38 can be bonded to the central region of the first width 46 of the first layer 36. The central region of the first width 46 can be the area adjacent a center line 78 of the first width 46 of the first layer 36 of the absorbent structure 34. It is to be understood that the central region of the first width 46 does not need to be the exact center of the first layer 36, but can be located generally around the center line 78 of the first width 46. In an embodiment, the central region of the first width 46 of the first layer 36 can be a position along the first width 46 which can be a distance 80 that can be about 0.35 to about 0.65 times the first width 46, as measured from either longitudinal edge, 52 or 54, of the first layer 36. In an embodiment, the second layer 38 does not have to be bonded to the first layer 36 in the central region of the first width 46, but rather could be bonded to the first layer 36 in an area adjacent to one of the longitudinal edges, 52 or 54, or at any other position along the first width 46 of the first layer 36 as deemed suitable. In the non-limiting embodiment of FIG. 15, first layer 36 can have at least one slit 96 associated with transverse edge 48 and second layer 38 can have at least one slit 96 associated with transverse edge 64. Each layer, 36 and 38, can have at least two successive slits 96 associated with their respective transverse edges, 48 and 64, and the two successive slits 96 can create a contact element 88 in each layer, 36 and 38. With regards to the at least one slit 96 associated with the transverse edge 48 of the first layer 36, the slit 96 can extend from a first surface 56 of the first layer 36 through to a second surface 58 of the first layer 36. The slit 96 associated with transverse edge 48 can extend from the transverse edge 48 in a direction towards an interior region of the first layer 36 of the absorbent structure 34 such that the slit 96 can extend in a direction towards the opposite transverse edge 50 of the first layer 36. With regards to the at least one slit 96 associated with the transverse edge 64 of the second layer 38, the slit 96 can extend from a first surface 72 through to a second surface 74 of the second layer 38. The slit 96 associated with transverse edge 64 can extend from the transverse edge 64 in a direction towards an interior region of the second layer 38 of the absorbent structure 34 such that the slit 96 can extend from the transverse edge 64 in a direction towards the opposite transverse edge 66 of the second layer 38. While the slits 96 of the first layer 36 and the slits 96 of the second layer 38 are illustrated in a manner in which the slits 96 of the second layer 38 can be positioned to substantially align with the slits 96 of the first layer 36, it should be realized that the slits 96 of the second layer 38 can be offset from the slits 96 of the first layer 36. An offset of the slits 96 of the second layer 38 from the slits 96 of the first layer 36 can be in any amount as deemed suitable. It should be realized that the slits 96 of each of the layers, 36 and 38, can have any length 98 as desired as the slits 96 extend from a transverse edge, 48 or 64, in a direction towards the opposite transverse edge, 50 or 66, of the first layer 36 or second layer 38, respectively. As illustrated in FIG. 15 in a non-limiting embodiment, at least one of the slits 96 of layer 36 and/or 38 can have a first slit length 104 and at least one of the slits 96 of the same layer, 36 and/or 38, can have a second slit length 106 wherein the first slit length 104 and the second slit length 106 are not the same. As illustrated in FIG. 15 in a non-limiting embodiment, the slits 96 may be incorporated into layer 36 and layer 38 in a pattern of alternating lengths. In an embodiment in which slits 96 having different lengths are incorporated into a layer, such as layer 36 and/or 38, the slits 96 having different lengths can be incorporated into the respective layer such that the different lengths of the slits 96 can be in a random sequence, in an alternating pattern, or in a repeating pattern. As illustrated in FIG. 15, the slits 96 do not necessarily extend the entire length, 44 or 60, of the first layer 36 or the second layer 38, respectively. As described herein, the transverse edges, 48, 50, 64, and 66, can be located at the insertion end 18 or the withdrawal end 20 of a resultant tampon 10. Thus, in an embodiment, the contact elements 88 of the absorbent structure 34 illustrated in FIG. 15 can be located at the insertion end 18 or the withdrawal end 20 of a resultant tampon 10. In the non-limiting embodiment illustrated in FIG. 15, the contact elements 88 of layers 36 and 38 can be oriented towards the insertion end 18 or the withdrawal end 20 of a resultant tampon 10. In an embodiment, at least one of the layers, 36 and/or 38, can also have at least one slit 96 associated with the opposite transverse edge, 50 and/or 66, respectively. It should be realized that in the non-limiting embodiment illustrated in FIG. 15, the contact elements 88 of the first layer 36 and the contact elements 88 of the second layer 38 need not be bonded to each other. Thus, it should be realized that the two layers, 36 and 38, do not need to be bonded to each other in any region wherein a contact element 88 is present.

Figure 16:
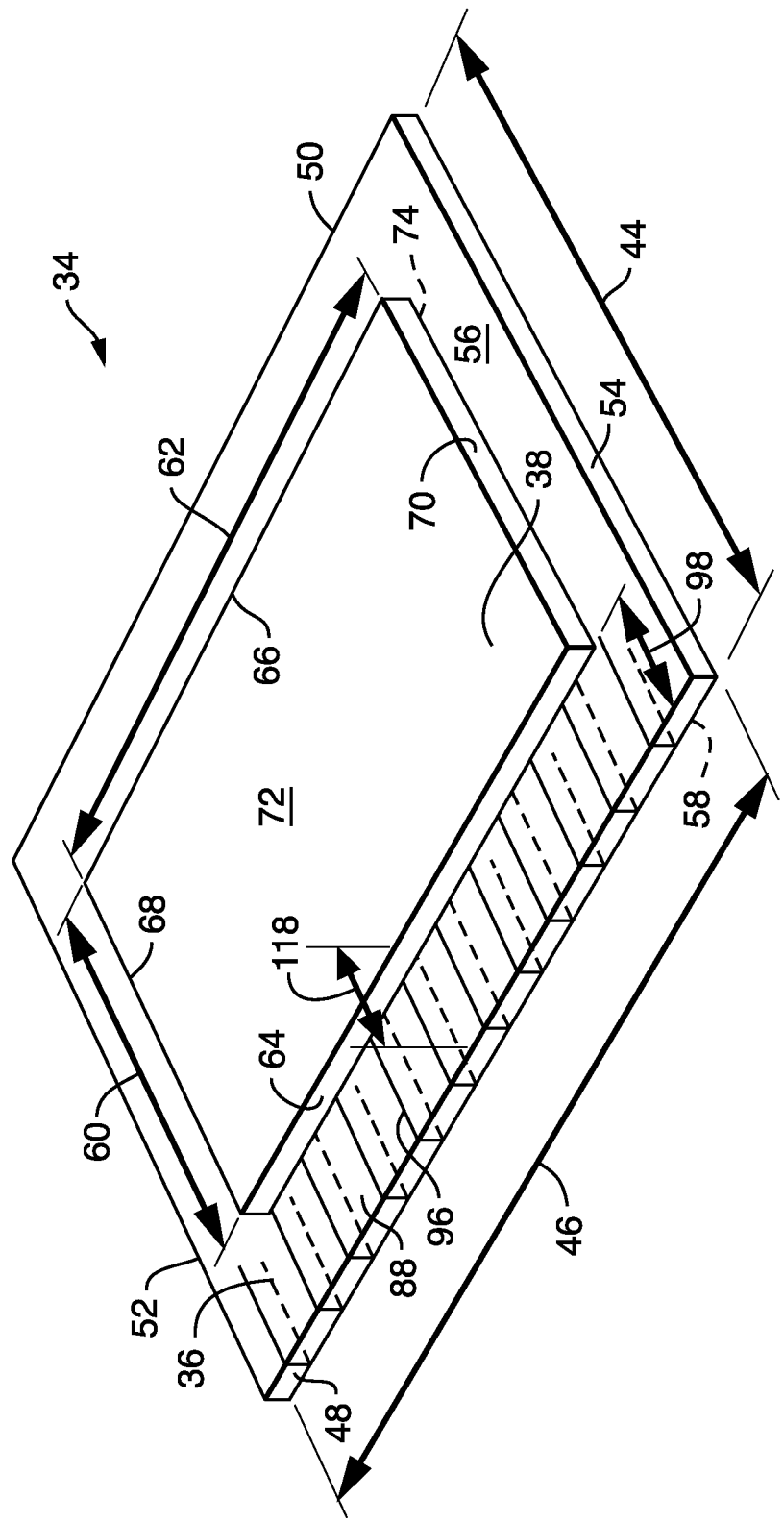
FIG. 16 is a perspective view of an embodiment of an absorbent structure with at least one contact element.

FIG. 16 provides an illustration of a non-limiting example of an embodiment of an absorbent structure 34 in which the first layer 36 can have a first length 44 and a first width 46 that can each be greater than the second length 60 and the second width 62 of the second layer 38. In the non-limiting illustration of FIG. 16, first layer 36 can have at least one slit 96 associated with a transverse edge such as transverse edge 48. The first layer 36 can have at least two successive slits 96 associated with transverse edge 48 and the two successive slits 96 can create a contact element 88. The slits 96 can extend from a first surface 56 of the first layer 36 through to a second surface 58 of the first layer 36. The slits 96 can extend from the transverse edge 48 in a direction away from the transverse edge 48 and towards an interior region of the first layer 36 of the absorbent structure 34 such that the slits 96 can extend in a direction toward the opposite transverse edge 50 of the first layer 36. It should be realized that the slits 96 can have any length 98 as desired as the slits 96 extend from transverse edge 48 in a direction towards the opposite transverse edge 50 of the first layer 36. As illustrated in FIG. 16 in a non-limiting embodiment, each slit 96 can have a length 98 substantially similar to the length 98 of each other slit 96 present. In an embodiment, the slits 96 can have varying lengths 98. As illustrated in FIG. 16, the slits 96 do not necessarily extend the entire first length 44 of the first layer 36. In an embodiment, the slits 96 can extend a length 98 that is substantially similar to, less than or greater than a distance 118 between transverse edge 48 and transverse edge 64. It should be realized that second layer 38 can be bonded to the first layer 36 at any position along the first length 44 and/or first width 46 of the first layer 36 as deemed suitable and can have any size dimension as deemed suitable. It should be realized that the two layers, 36 and 38, do not need to be bonded to each other in any region wherein a contact element 88 is present. As described herein, the transverse edge 48 can be located at the insertion end 18 or the withdrawal end 20 of a resultant tampon 10. Thus, in an embodiment, the contact elements 88 of the absorbent structure 34 illustrated in FIG. 16 can be located at the insertion end 18 or the withdrawal end 20 of a resultant tampon 10. In the non-limiting embodiment illustrated in FIG. 16, the contact elements 88 can be oriented towards the insertion end 18 or the withdrawal end 20 of a resultant tampon 10. In embodiment, at least one slit 96 can also be incorporated into second layer 38.

Figure 17:
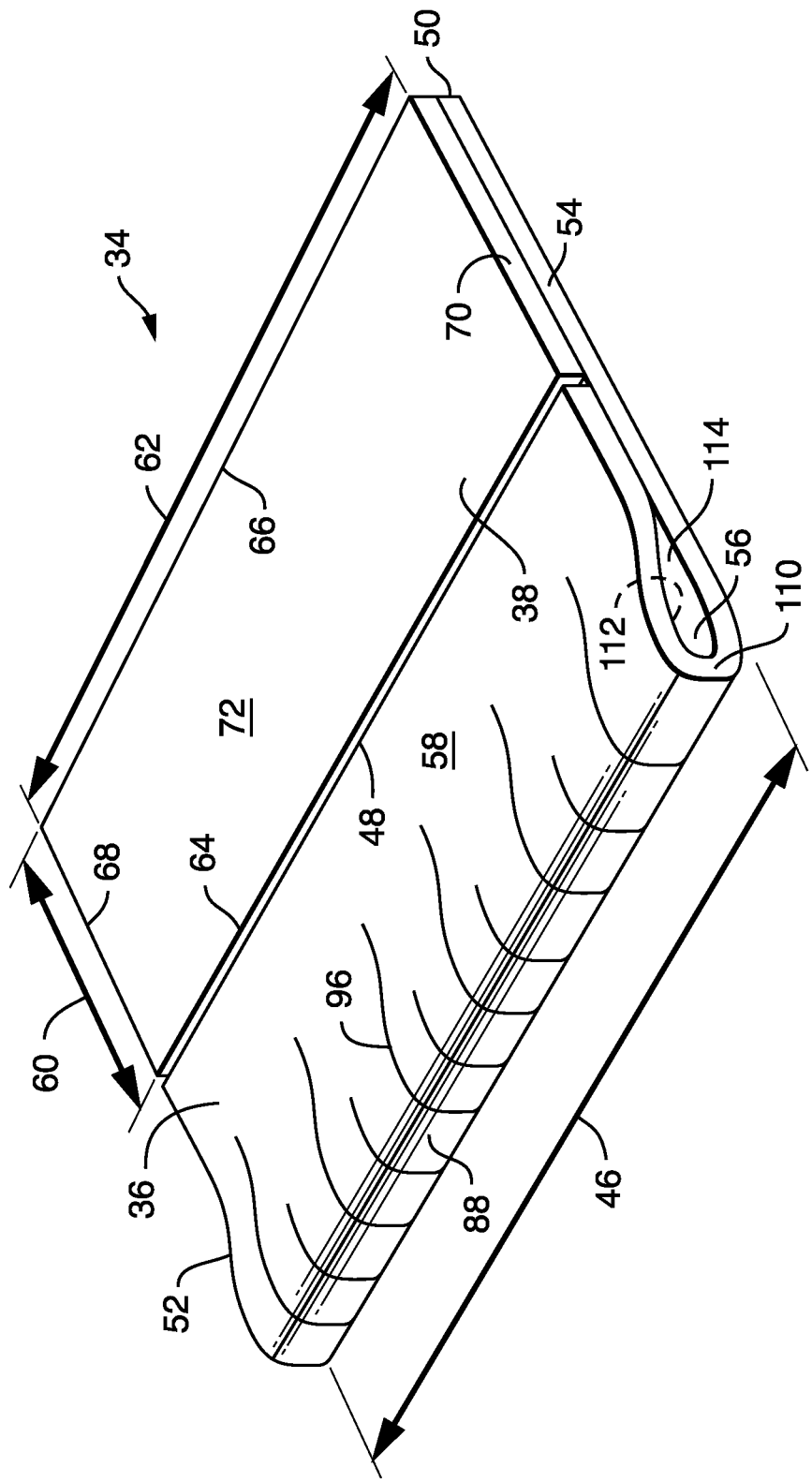
FIG. 17 is a perspective view of an embodiment of an absorbent structure with at least one contact element.

FIG. 17 provides an illustration of a non-limiting example of an embodiment of an absorbent structure 34 which can have two layers, 36 and 38. As illustrated, first layer 36 can have a first width 46 that can be substantially similar to a second width 62 of the second layer 38. As illustrated, first layer 36 can have at least one fold 110 incorporated therein. In such an embodiment in which a fold 110 is present, the first layer 36 can be bent upon itself such that a first portion of at least one of the surfaces, 56 or 58, can be in communication with a second portion of the same surface, 56 or 58. As a non-limiting example, as illustrated in FIG. 17, the first layer 36 can contain a single fold 110 bringing a first portion 112 of the first surface 56 into communication with a second portion 114 of the first surface 56. In the non-limiting embodiment illustrated in FIG. 17, the fold 110 can bring transverse edge 48 of first layer 36 into communication with transverse edge 64 of the second layer 38. It should be realized that layer 36 can have a first length 44 greater than a second length 60 of layer 38 and fold 110 can occur at any desired location along the first length 44 of layer 36. In an embodiment, a fold 110 can bring transverse edge 48 of layer 36 into communication with transverse edge 64 of layer 38, into communication with a portion of second layer 38 located between transverse edges 64 and 66, into communication with transverse edge 66 of second layer 38, into a configuration wherein transverse edge 48 can extend beyond transverse edge 66, or to a location of first layer 36 such that transverse edge 48 is not in communication with the second layer 38. As illustrated, first layer 36 can have at least one slit 96 which can be cut through from a second surface 58, through the first and second portions, 112 and 114, of the first surface 56, and to the opposite second surface 58 of the first layer 36. The first layer 36 can have at least two successive slits 96 and the two successive slits 96 can create a contact element 88. As illustrated, the slit(s) 96 can be associated with the fold 110 of the first layer 36. The slit(s) 96 can extend from the fold 110 of the first layer 36 in a direction away from the fold 110 and towards the interior region of the absorbent structure 34 such that the slits 96 can extend from the fold 110 of first layer 36 in a direction towards transverse edge 50 of layer 36. The slit(s) 96 can be incorporated into the first layer 36 prior to or after fold 110 has been incorporated into layer 36. It should be realized that, in an embodiment, at least one slit 96 can be incorporated into second layer 38. In an embodiment, at least one of the layers, 36 and/or 38, can have at least one slit 96 associated with the transverse edges, 48, 50, 64 and/or 66, respectively. As described herein, the fold 110 can be located at the insertion end 18 or the withdrawal end 20 of a resultant tampon 10. Thus, in an embodiment, the contact elements 88 of the absorbent structure 34 illustrated in FIG. 17 can be located at the insertion end 18 or the withdrawal end 20 of a resultant tampon 10. In the non-limiting embodiment illustrated in FIG. 17, the contact elements 88 can be oriented towards the insertion end 18 or the withdrawal end 20 of a resultant tampon 10.

Figure 18:
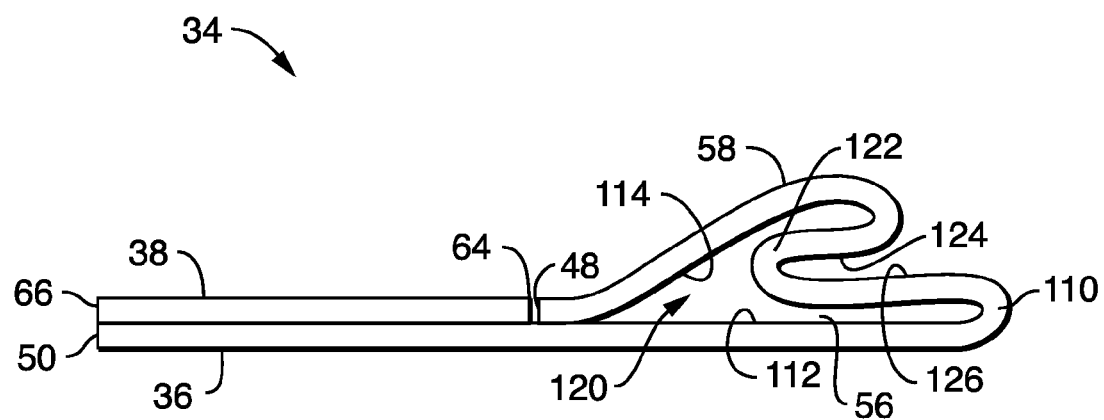
FIG. 18 is a side view of an embodiment of an absorbent structure.

FIG. 18 provides an illustration of a non-limiting example of an embodiment of an absorbent structure 34 which can have two layers 36 and 38. As illustrated, the first layer 36 can have two transverse edges, 48 and 50, and the second layer 38 can have two transverse edges, 64 and 66. In an embodiment, the first layer 36 can have more than one fold, such as folds 110 and 122, incorporated therein. In such an embodiment, the first fold 110 can bring transverse edge 48 of first layer 36 into communication with transverse edge 64 of the second layer 38. In an embodiment, fold 110 can bring transverse edge 48 of layer 36 into communication with transverse edge 64 of layer 38, into communication with a portion of layer 38 located between transverse edges 64 and 66, into communication with transverse edge 66 of layer 38, into a configuration wherein transverse edge 48 can extend beyond transverse edge 66, or to a location of layer 36 such that transverse edge 48 is not in communication with layer 38. In such an embodiment, a first portion 112 of first surface 56 of the first layer 36 can be brought into a face-to-face relationship with a second portion 114 of first surface 56 of the first layer 36. In an embodiment, the fold 110 can be utilized to bring the two portions, 112 and 114, into a facing relationship and, in some embodiments, a space 120 can exist between the two portions, 112 and 114, while they are in a facing relationship. In an embodiment, such as illustrated in the non-limiting embodiment of FIG. 18, a second fold 122 can be incorporated into layer 36. In the non-limiting illustration, the second fold 122 can be incorporated into layer 36 at any location of the first layer 36 such as, for example, at a location between the transverse edge 48 and the first fold 110. The second fold 122 can be configured such that the second fold 122 can position a portion of the first layer 36 into the space 120 created by the first fold 110. The second fold 122 can bring a first portion 124 of the second surface 58 into a facing relationship with a second portion 126 of the second surface 58 of the first layer 36. The first layer 36 can have at least one slit 96 incorporated therein (not shown). The at least one slit 96 can be incorporated into layer 36 before or after the incorporation of either of the folds, 110 and/or 122. The at least one slit 96 can be associated with either or both of the folds 110 and/or 122. In an embodiment in which slits 96 are associated with only one of the folds, 110 or 122, the contact element(s) 88 formed by the incorporation of the slits 96 can be in an at least partially overlapping relationship with a portion of the folded first layer 36 not containing any slits 96 or contact elements 88. In an embodiment in which slits 96 are associated with each of the folds, 110 and 122, the contact element(s) 88 formed by the incorporation of the slits 96 can be in an at least partially overlapping relationship. As described herein, the folds 110 and 122 can be located at the insertion end 18 or the withdrawal end 20 of a resultant tampon 10. Thus, in an embodiment, the contact elements 88 of the absorbent structure 34 illustrated in FIG. 18 can be located at the insertion end 18 or the withdrawal end 20 of a resultant tampon 10. In the non-limiting embodiment illustrated in FIG. 18, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 19:
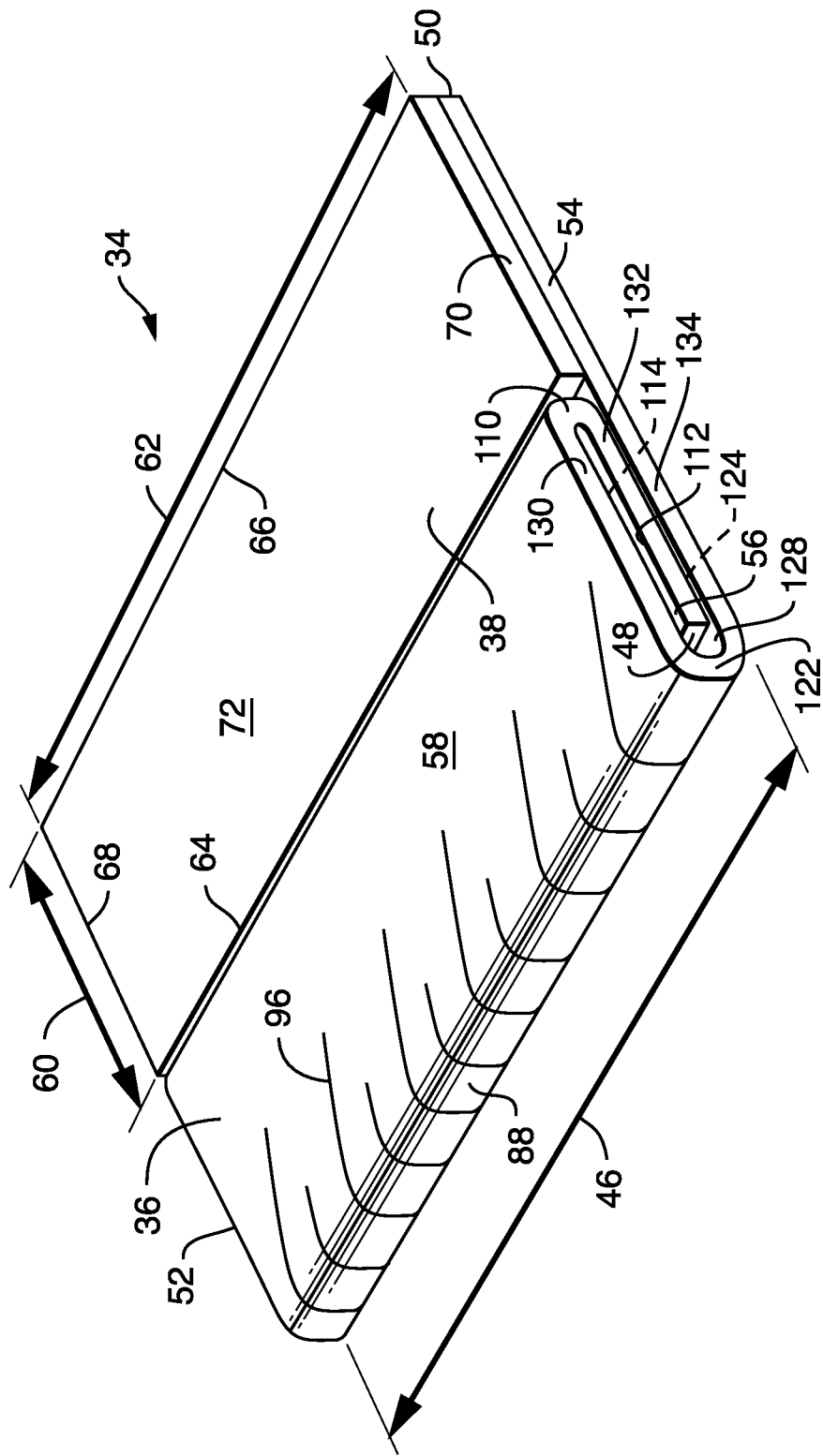
FIG. 19 is a perspective view of an embodiment of an absorbent structure with at least one contact element.

FIG. 19 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, first layer 36 can have at least two folds, 110 and 122, incorporated therein. In such an embodiment in which two folds, 110 and 122, are present, the layer 36 can be bent upon itself such that a first portion of one surface, 56 or 58, of the layer 36 can be in a facing relationship with a second portion of the same surface, 56 or 58, and a third portion of one surface, 56 or 58, of the layer 36 can be in a facing relationship with a first portion of the other surface, 56 or 58. As a non-limiting example, as illustrated in FIG. 19, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a third portion 128 of the first surface 56 into a facing relationship with a first portion 124 of the second surface 58 of layer 36. The second fold 122 can be created by bending layer 36 at a location along the first length 44 of layer 36 between the transverse edge 48 of layer 36 and the transverse edge 64 of layer 38. As illustrated in FIG. 19, following the folding of layer 36 with fold 122, transverse edge 48 need not be in communication with second layer 38 of the absorbent structure 34. In an embodiment, each fold 110 and 122 can result in layer 36 having multiple layers, such as layers 130, 132, and 134. In an embodiment, layer 36 can have at least one slit 96 extending through the layers, 130, 132 and 134, of the layer 36. The first layer 36 can have at least two successive slits 96 and the two successive slits 96 can create a contact element 88. As illustrated, the at least one slit 96 can extend from the second surface 58 of layer 36, through the first and second portions, 112 and 114, of the first surface 56 of layer 36, through the first portion 124 of the second surface 58 of layer 36 and the third portion 128 of the first surface 56 of layer 36, and to the opposite second surface 58 of the first layer 36. As illustrated, the slit(s) 96 can be associated with the second fold 122 of the first layer 36. The slit(s) 96 can extend from the fold 122 of the first layer 36 in a direction away from the fold 122 and towards the interior region of the absorbent structure 34 such that the slits 96 can extend from the fold 122 of first layer 36 in a direction towards transverse edge 50 of layer 36. The at least one slit 96 can be incorporated into layer 36 prior to or after layer 36 has been folded. As described herein, the fold 122 can be located at the insertion end 18 or the withdrawal end 20 of a resultant tampon 10. Thus, in an embodiment, the contact elements 88 of the absorbent structure 34 illustrated in FIG. 19 can be located at the insertion end 18 or the withdrawal end 20 of a resultant tampon 10. In the non-limiting embodiment illustrated in FIG. 19, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 20:
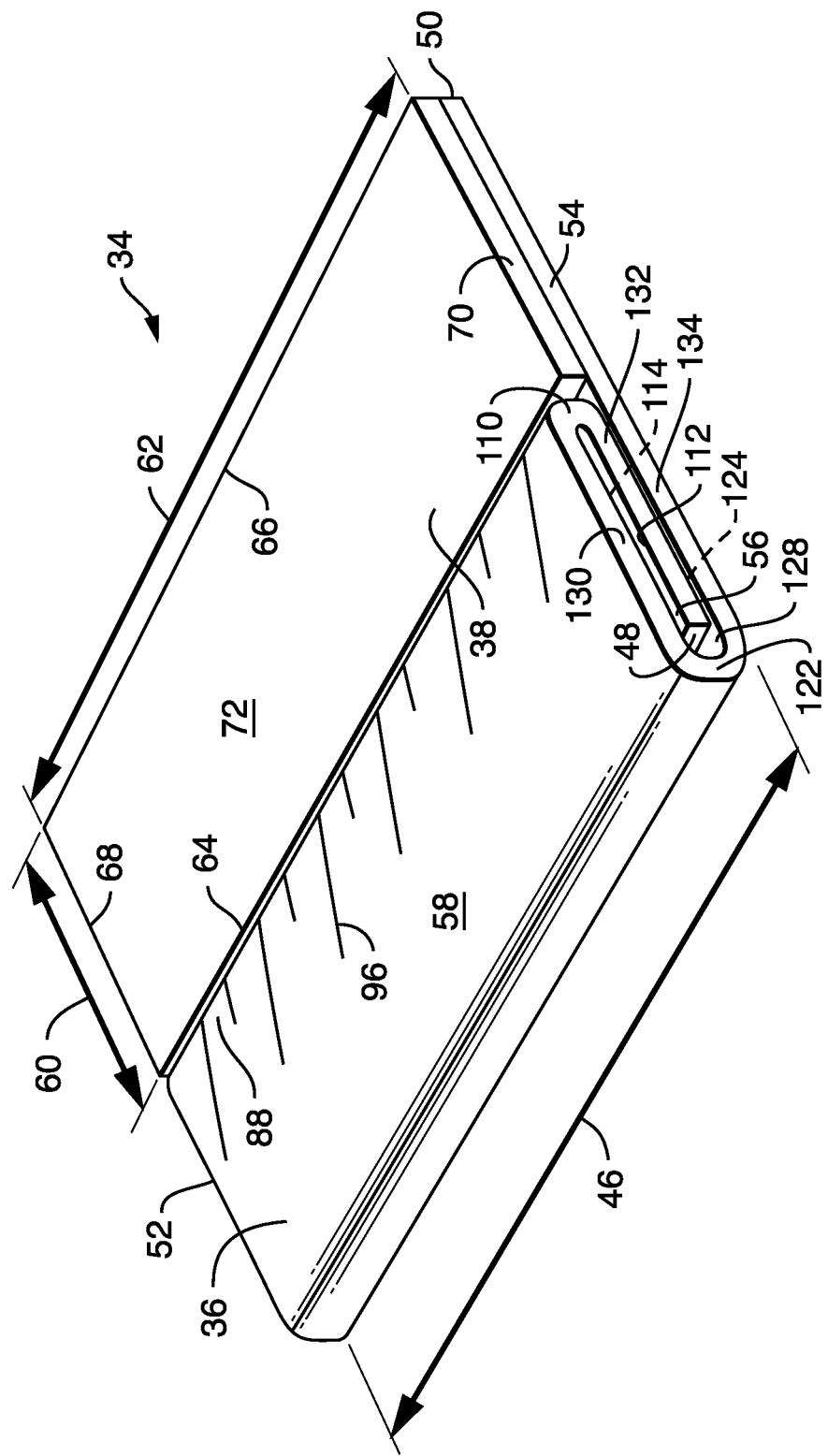
FIG. 20 is a perspective view of an embodiment of an absorbent structure with at least one contact element.

FIG. 20 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, first layer 36 can have at least two folds, 110 and 122, incorporated therein. In such an embodiment in which two folds 110 and 122, are present, the layer 36 can be bent upon itself such that a first portion of one surface, 56 or 58, of the layer 36 can be in a facing relationship with a second portion of the same surface, 56 or 58, and a third portion of one surface, 56 or 58, of the layer 36 can be in a facing relationship with a first portion of the other surface, 56 or 58. As a non-limiting example, as illustrated in FIG. 20, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a third portion 128 of the first surface 56 into a facing relationship with a first portion 124 of the second surface 58 of layer 36. The second fold 122 can be created by bending layer 36 at a location along the first length 44 of layer 36 between the transverse edge 48 of layer 36 and the transverse edge 64 of layer 38. As illustrated in FIG. 20, following the folding of layer 36 with fold 122, transverse edge 48 need not be in communication with second layer 38 of the absorbent structure 34. In an embodiment, each fold 110 and 122 can result in layer 36 having multiple layers, such as layers 130, 132, and 134. In an embodiment, layer 36 can have at least one slit 96 extending through the layers, 130 and 132, of the layer 36.

The first layer 36 can have at least two successive slits 96 extending through the layers, 130 and 132, and the two successive slits 96 can create a contact element 88. As illustrated, the at least one slit 96 can extend from the second surface 58 of layer 36 and through the first and second portions, 112 and 114, of the first surface 56 of layer 36 to the first portion 124 of the second surface 58 of layer 36. As illustrated, the slit(s) 96 can be associated with the first fold 110 of the first layer 36. The slit(s) 96 can extend from the fold 110 of the first layer 36 in a direction away from the fold 110 and towards the second fold 122 of the first layer 36. The at least one slit 96 can be incorporated into layer 36 prior to or after layer 36 has been folded with the first fold 110. As described herein, the fold 110 can be located at a location between the insertion end 18 and the withdrawal end 20 of a resultant tampon 10. Thus, in an embodiment, the contact elements 88 of the absorbent structure 34 illustrated in FIG. 20 can be located at a location between the insertion end 18 and the withdrawal end 20 of a resultant tampon 10. In the non-limiting embodiment illustrated in FIG. 20, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 21:
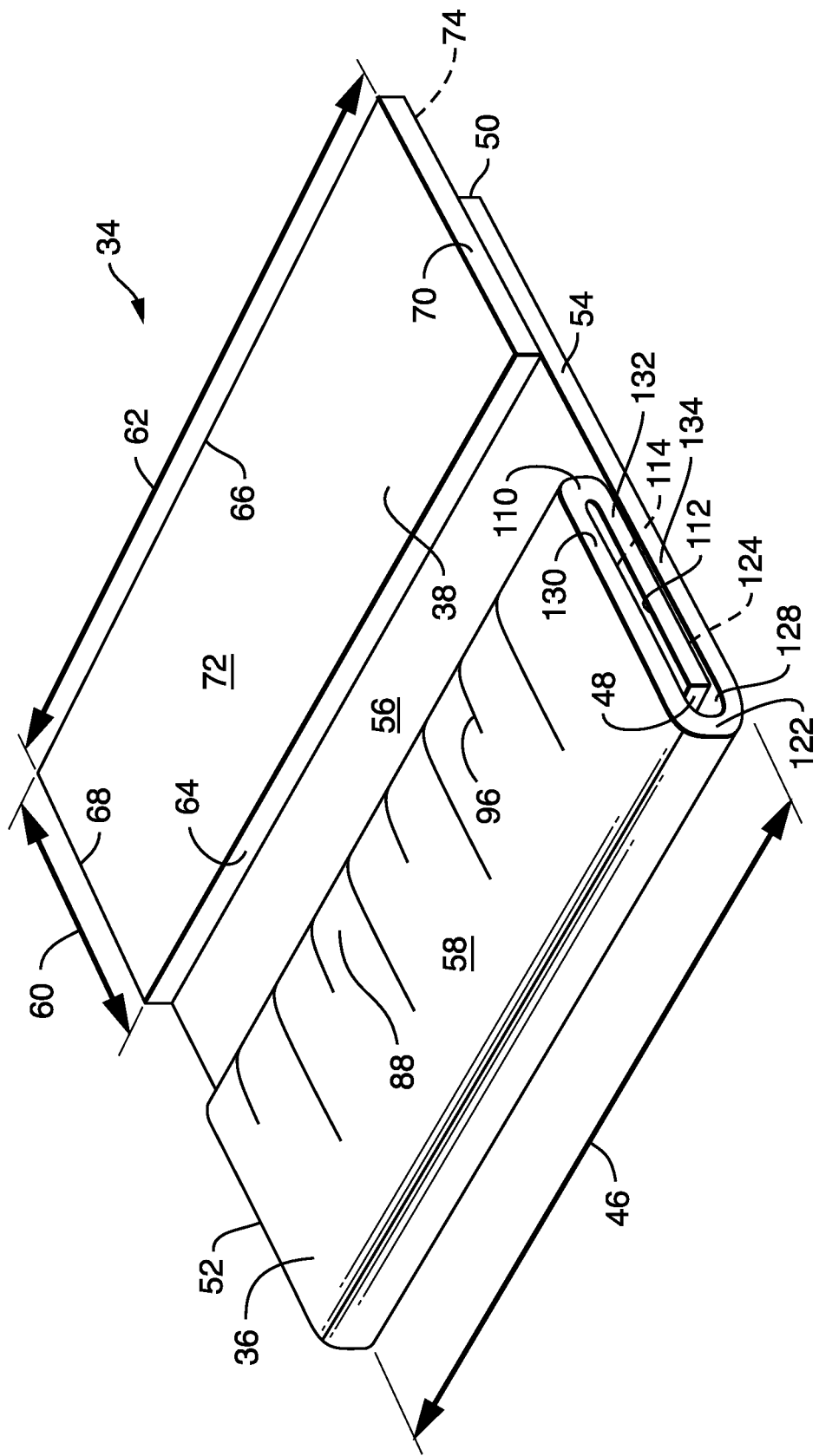
FIG. 21 is a perspective view of an embodiment of an absorbent structure with at least one contact element.

FIG. 21 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, less than 100% of surface 74 of second layer 38 can be in a face to face relationship with surface 56 of first layer 36. As illustrated, first layer 36 can have at least two folds, 110 and 122, incorporated therein. In such an embodiment in which two folds 110 and 122 are present, the layer 36 can be bent upon itself such that a first portion of one surface, 56 or 58, of the layer 36 can be in a facing relationship with a second portion of the same surface, 56 or 58, and a third portion of one surface, 56 or 58, of the layer 36 can be in a facing relationship with a first portion of the other surface, 56 or 58. As a non-limiting example, as illustrated in FIG. 21, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a third portion 128 of the first surface 56 into a facing relationship with a first portion 124 of the second surface 58 of layer 36. The second fold 122 can be created by bending layer 36 at a location along the first length 44 of layer 36 between the transverse edge 48 of layer 36 and the transverse edge 64 of layer 38. As illustrated in FIG. 21, following the folding of layer 36 with fold 122, transverse edge 48 need not be in communication with second layer 38 of the absorbent structure 34. In an embodiment, each fold 110 and 122 can result in layer 36 having multiple layers, such as layers 130, 132, and 134. In an embodiment, layer 36 can have at least one slit 96 extending through the layers, 130 and 132, of the layer 36. The first layer 36 can have at least two successive slits 96 extending through the layers, 130 and 132, and the two successive slits 96 can create a contact element 88. As illustrated, the at least one slit 96 can extend from the second surface 58 of layer 36 and through the first and second portions, 112 and 114, of the first surface 56 of layer 36 to the first portion 124 of the second surface 58 of layer 36. As illustrated, the slit(s) 96 can be associated with the first fold 110 of the first layer 36. The slit(s) 96 can extend from the fold 110 of the first layer 36 in a direction away from the fold 110 and towards the second fold 122 of the first layer 36. The at least one slit 96 can be incorporated into layer 36 prior to or after layer 36 has been folded with the first fold 110. As described herein, the fold 110 can be located at a location between the insertion end 18 and the withdrawal end 20 of a resultant tampon 10. Thus, in an embodiment, the contact elements 88 of the absorbent structure 34 illustrated in FIG. 21 can be located at a location between the insertion end 18 and the withdrawal end 20 of a resultant tampon 10. In the non-limiting embodiment illustrated in FIG. 21, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 22:
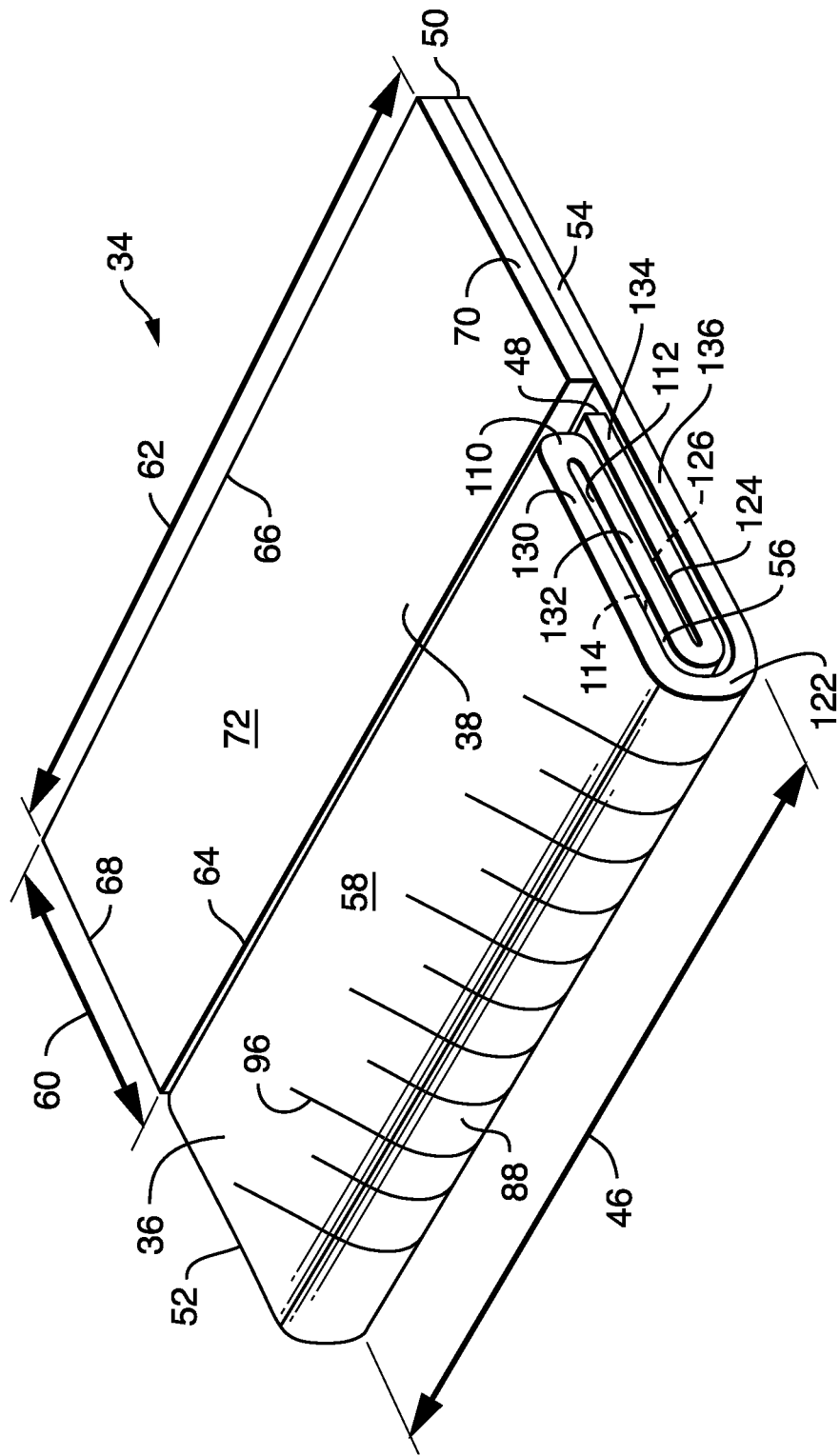
FIG. 22 is a perspective view of an embodiment of an absorbent structure with at least one contact element.

FIG. 22 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, first layer 36 can have at least two folds, 110 and 122, incorporated therein. In such an embodiment as illustrated in FIG. 22 in which two folds, 110 and 122, are present, the layer 36 can be bent upon itself such that a first portion of one surface, 56 or 58, of the layer 36 can be in a facing relationship with a second portion of the same surface, 56 or 58, and a first portion of the other surface, 56 or 58, of the layer 36 can be in a facing relationship with a second portion of the same surface, 56 or 58. As a non-limiting example, as illustrated in FIG. 22, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a first portion 124 of the second surface 58 into a facing relationship with a second portion 126 of the second surface 58 of layer 36. The second fold 122 can be created by bending layer 36 at a location along the first length 44 of layer 36 between the transverse edge 48 of layer 36 and the first fold 110 of layer 36. As illustrated in FIG. 22, transverse edge 48 of layer 36 can be in communication with transverse edge 64 of the second layer 38 of the absorbent structure 34. In an embodiment, each fold 110 and 122 can result in layer 36 having multiple layers, such as layers 130, 132, 134 and 136. In an embodiment, layer 36 can have at least one slit 96 extending through the layers, 130, 132, 134, and 136, of the layer 36. The first layer 36 can have at least two successive slits 96 extending through the layers, 130, 132, 134, and 136, and the two successive slits 96 can create a contact element 88. As illustrated, the at least one slit 96 can extend from the second surface 58 of layer 36, through the first and second portions, 112 and 114, of the first surface 56 of layer 36, through the first and second portions, 124 and 126, of the second surface 58 of layer 36, through opposite first and second portions, 112 and 114, of the first surface 56 of layer 36, and to the opposite second surface 58 of the first layer 36. As illustrated, the slit(s) 96 can be associated with the second fold 122 of the first layer 36. The slit(s) 96 can extend from the fold 122 of the first layer 36 in a direction away from the fold 122 and towards the interior region of the absorbent structure 34 such that the slits 96 can extend from the fold 122 of first layer 36 in a direction towards transverse edge 50 of layer 36. The at least one slit 96 can be incorporated into layer 36 prior to or after layer 36 has been folded. As described herein, the fold 122 can be located at the insertion end 18 or the withdrawal end 20 of a resultant tampon 10. Thus, in an embodiment, the contact elements 88 of the absorbent structure 34 illustrated in FIG. 22 can be located at the insertion end 18 or the withdrawal end 20 of a resultant tampon 10. In the non-limiting embodiment illustrated in FIG. 22, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 23:
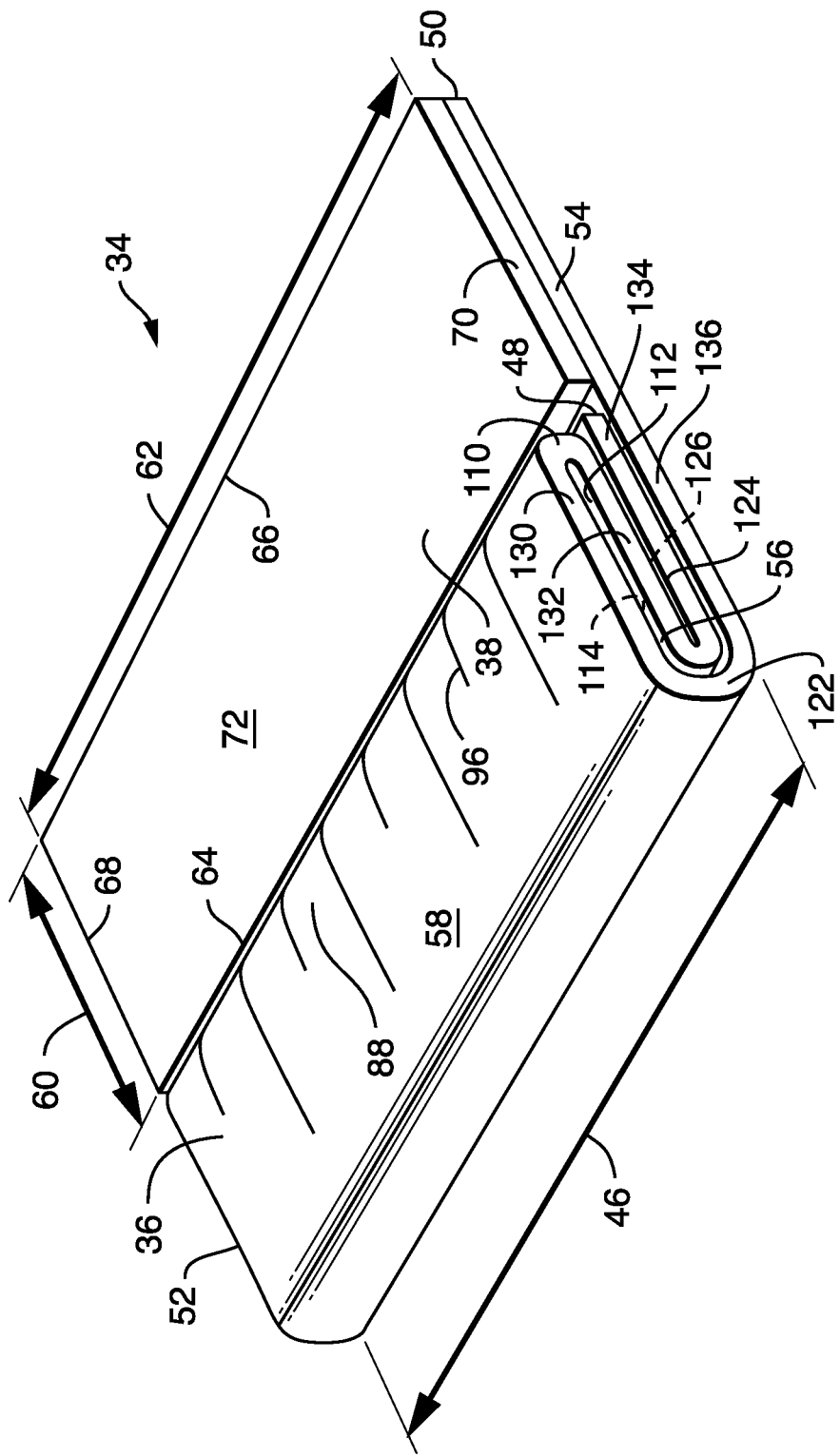
FIG. 23 is a perspective view of an embodiment of an absorbent structure with at least one contact element.

FIG. 23 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, first layer 36 can have at least two folds, 110 and 122, incorporated therein. In such an embodiment as illustrated in FIG. 23 in which two folds, 110 and 122, are present, the layer 36 can be bent upon itself such that a first portion of one surface, 56 or 58, of the layer 36 can be in a facing relationship with a second portion of the same surface, 56 or 58, and a first portion of the other surface, 56 or 58, of the layer 36 can be in a facing relationship with a second portion of the same surface, 56 or 58. As a non-limiting example, as illustrated in FIG. 23, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a first portion 124 of the second surface 58 into a facing relationship with a second portion 126 of the second surface 58 of layer 36. The second fold 122 can be created by bending layer 36 at a location along the first length 44 of layer 36 between the transverse edge 48 of layer 36 and the first fold 110 of layer 36. As illustrated in FIG. 23, transverse edge 48 of layer 36 can be in communication with transverse edge 64 of the second layer 38 of the absorbent structure 34. In an embodiment, each fold 110 and 122 can result in layer 36 having multiple layers, such as layers 130, 132, 134 and 136. In an embodiment, layer 36 can have at least one slit 96 extending through the layers, such as layers 130 and 132, of the layer 36. The first layer 36 can have at least two successive slits 96 extending through the layers, 130 and 132, and the two successive slits 96 can create a contact element 88. As illustrated, the at least one slit 96 can extend from the second surface 58 of layer 36, through the first and second portions, 112 and 114, of the first surface 56 of layer 36, and to the second portion 126 of the second surface 58 of layer 36. As illustrated, the slit(s) 96 can be associated with the first fold 110 of the first layer 36. The slit(s) 96 can extend from the fold 110 of the first layer 36 in a direction away from the fold 110 and towards the second fold 122 of first layer 36. The at least one slit 96 can be incorporated into layer 36 prior to or after layer 36 has been folded. As described herein, the fold 110 can be located between the insertion end 18 and the withdrawal end 20 of a resultant tampon 10. Thus, in an embodiment, the contact elements 88 of the absorbent structure 34 illustrated in FIG. 23 can be located between the insertion end 18 and the withdrawal end 20 of a resultant tampon 10. In the non-limiting embodiment illustrated in FIG. 23, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

Figure 24:
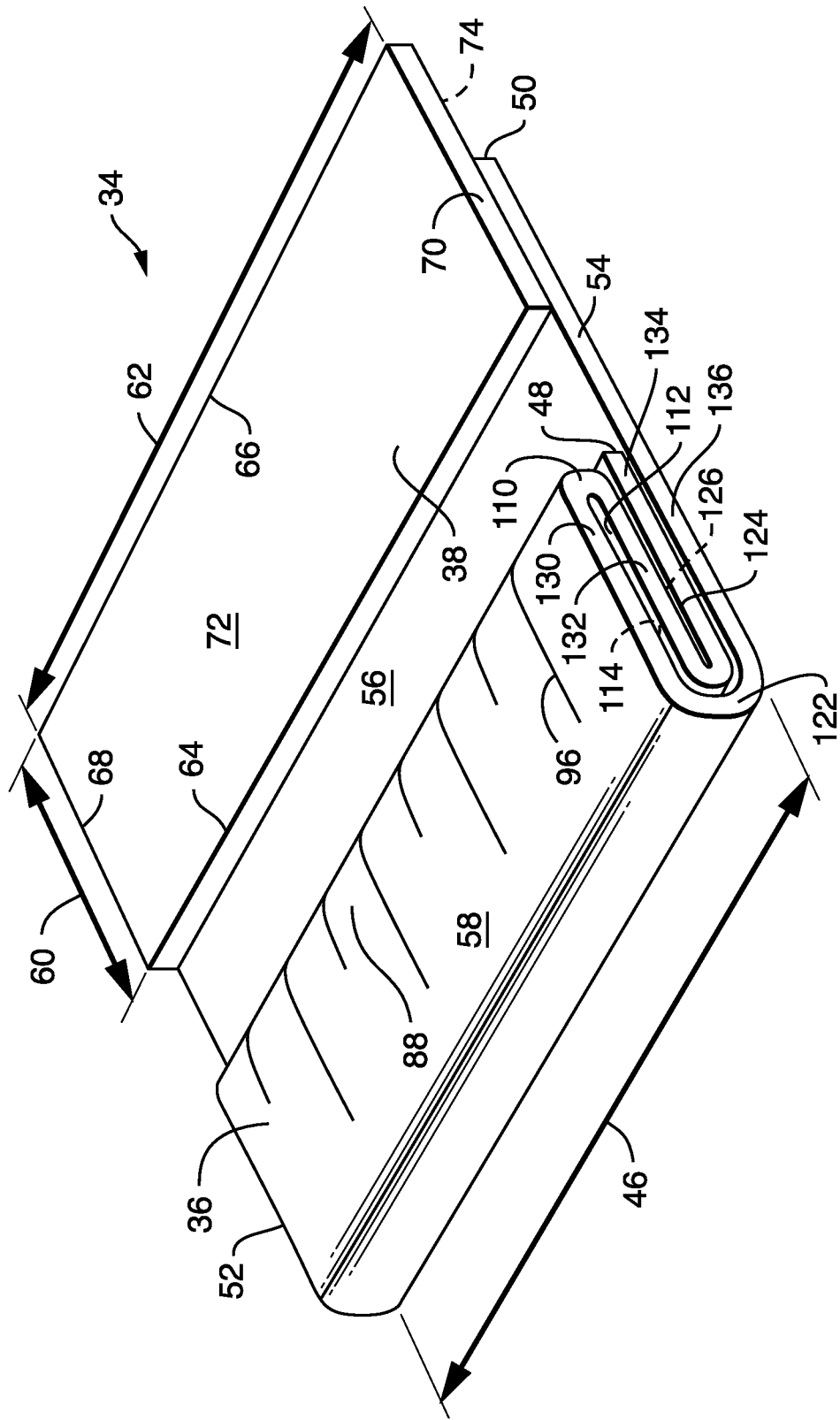
FIG. 24 is a perspective view of an embodiment of an absorbent structure with at least one contact element.

FIG. 24 provides an illustration of a non-limiting embodiment of an absorbent structure 34 which can have two layers, 36 and 38. As illustrated, the first layer 36 can have a first width 46 that can be substantially similar to a second width 62 of the second layer 38. The first layer 36 can have a first length 44 which can be longer than a second length 60 of the second layer 38. As illustrated, less than 100% of surface 74 of second layer 38 can be in a face to face relationship with surface 56 of first layer 36. As illustrated, first layer 36 can have at least two folds, 110 and 122, incorporated therein. In such an embodiment as illustrated in FIG. 24 in which two folds 110 and 122 are present, the layer 36 can be bent upon itself such that a first portion of one surface, 56 or 58, of the layer 36 can be in a facing relationship with a second portion of the same surface, 56 or 58, and a first portion of the other surface, 56 or 58, of the layer 36 can be in a facing relationship with a second portion of the same surface, 56 or 58. As a non-limiting example, as illustrated in FIG. 24, the layer 36 can contain a first fold 110 bringing a first portion 112 of the first surface 56 into a facing relationship with a second portion 114 of the first surface 56. Following the creation of the first fold 110, the transverse edge 48 of layer 36 can be located at any location along the first length 44 of layer 36 between the first fold 110 and transverse edge 64 of layer 38. The layer 36 can contain a second fold 122 bringing a first portion 124 of the second surface 58 into a facing relationship with a second portion 126 of the second surface 58 of layer 36. The second fold 122 can be created by bending layer 36 at a location along the first length 44 of layer 36 between the transverse edge 48 of layer 36 and the first fold 110 of layer 36. As illustrated in FIG. 24, transverse edge 48 of layer 36 does not have to be, but can be, in communication with transverse edge 64 of the second layer 38 of the absorbent structure 34. In an embodiment, each fold 110 and 122 can result in layer 36 having multiple layers, such as layers 130, 132, 134 and 136. In an embodiment, layer 36 can have at least one slit 96 extending through the layers, 130 and 132, of the layer 36. The first layer 36 can have two successive slits 96 extending through the layers, 130 and 132, and the two successive slits 96 can create a contact element 88. As illustrated, the at least one slit 96 can extend from the second surface 58 of layer 36, through the first and second portions, 112 and 114, of the first surface 56 of layer 36, and to the second portion 126 of the second surface 58 of layer 36. As illustrated, the slit(s) 96 can be associated with the first fold 110 of the first layer 36. The slit(s) 96 can extend from the fold 110 of the first layer 36 in a direction away from the fold 110 and towards the second fold 122 of first layer 36. The at least one slit 96 can be incorporated into layer 36 prior to or after layer 36 has been folded. As described herein, the fold 110 can be located between the insertion end 18 and the withdrawal end 20 of a resultant tampon 10. Thus, in an embodiment, the contact elements 88 of the absorbent structure 34 illustrated in FIG. 24 can be located between the insertion end 18 and the withdrawal end 20 of a resultant tampon 10. In the non-limiting embodiment illustrated in FIG. 24, the contact elements 88 can be oriented towards the insertion end 18 or the withdrawal end 20 of a resultant tampon 10. In an embodiment, at least one slit 96 can be incorporated into second layer 38. In an embodiment, at least one of the layers, 36 and/or 38, can have at least one slit 96 associated with the transverse edges, 48, 50, 64 and/or 66, respectively.

As described herein, the nonwoven ribbon 32 of an absorbent structure 34 can be separated into individual units of fleece 30 which can have the same absorbent structure 34 as was present in the nonwoven ribbon 32. The fleece 30 can be formed into a blank 28 which can then be compressed into a pledget 12 of a tampon 10. In various embodiments, the tampon 10 can have a cover 138 and a withdrawal aid 14.

In various embodiments a cover 138 can be provided. As used herein, the term "cover" relates to materials that are in communication with and cover or enclose surfaces of a pledget 12 to prevent the fibrous materials of the absorbent structure 34 from directly contacting the inner walls of a woman's vagina and to reduce the ability of portions (e.g., fibers and the like) from becoming separated from the pledget 12 or the tampon 10 and being left behind upon removal of the tampon 10 from the woman's vagina. In various embodiments, the cover 138 can be a fluid-permeable cover 138. By "fluid-permeable" it is meant that body fluid is able to pass through the cover 138. The cover 138 can be hydrophobic or hydrophilic. By "hydrophilic" it is meant that the cover 138 has an affinity for absorbing or tending to combine with water. By "hydrophobic" it is meant that the cover 138 is antagonistic to or tending not to combine with water. The cover 138 can also be treated with a surfactant or other material to make it hydrophilic or to make it more hydrophilic.

The cover 138 can be bonded with: the nonwoven ribbon 32 prior to separation into individual units of fleece 30, an individual unit of fleece 30, a blank 28 which has been formed from a fleece 30, or to the pledget 12 following compression of the blank 28. In an embodiment in which the cover 138 is bonded with a pledget 12 following compression of a blank 28, the cover 138 can be extensible such that the tampon 10 can expand within the vaginal cavity. In an embodiment in which the absorbent structure 34 is multi-layered, the cover 138 can be bonded with at least one layer of the absorbent structure 34 before, after, or while the layer of the absorbent structure 34 is bonded to another layer of the absorbent structure 34. The absorbent structure 34 can be in a nonwoven ribbon 32 or can be in a fleece 30.

In various embodiments, the cover 138 can be formed from nonwoven materials or apertured films. The nonwoven materials can include, but are not limited to, materials such as natural fibers, synthetic fibers, or blends of natural and synthetic fibers. Natural fibers include, but are not limited to, rayon, cotton, wood pulp, flax, and hemp. Synthetic fibers can include, but are not limited to, fibers such as polyester, polyolefin, nylon, polypropylene, polyethylene, polyacrylic, vinyl polyacetate, polyacrylate, cellulose acetate, or bicomponent fibers, such as bicomponent polyethylene and polypropylene fibers. The cover 138 can be made by any number of suitable techniques such as, for example, being spunbonded, carded, hydroentangled, thermally bonded, and resin bonded. In an embodiment, the cover 138 can be formed from an apertured thermoplastic film having either a two-dimensional or a three-dimensional thickness. In an embodiment, the cover 138 can be a 12 gsm smooth calendared material made from bicomponent, polyethylene sheath and polyester core, fibers such as Sawabond 4189 available from Sandler AG, Schwarzenbach, Germany. In an embodiment, the cover 138 can be formed from a single piece of material.

In an embodiment, the cover 138 can be formed from multiple discrete pieces of material which are bonded together. In an embodiment, the cover 138 can be bleached. In an embodiment, the cover 138 can have a color.

In an embodiment, the cover 138 can be treated with an aqueous solution to reduce frictional drag, to give the tampon 10 a permanent wettability, to enhance the ease of insertion into and withdrawal from a woman's vagina, and combinations thereof. In an embodiment, the cover 138 can be treated either before being rolled or folded up with the fleece 30 into a blank 28 or after the blank 28 has been formed and the cover 138 has been bonded with the blank 28.

Figure 25:
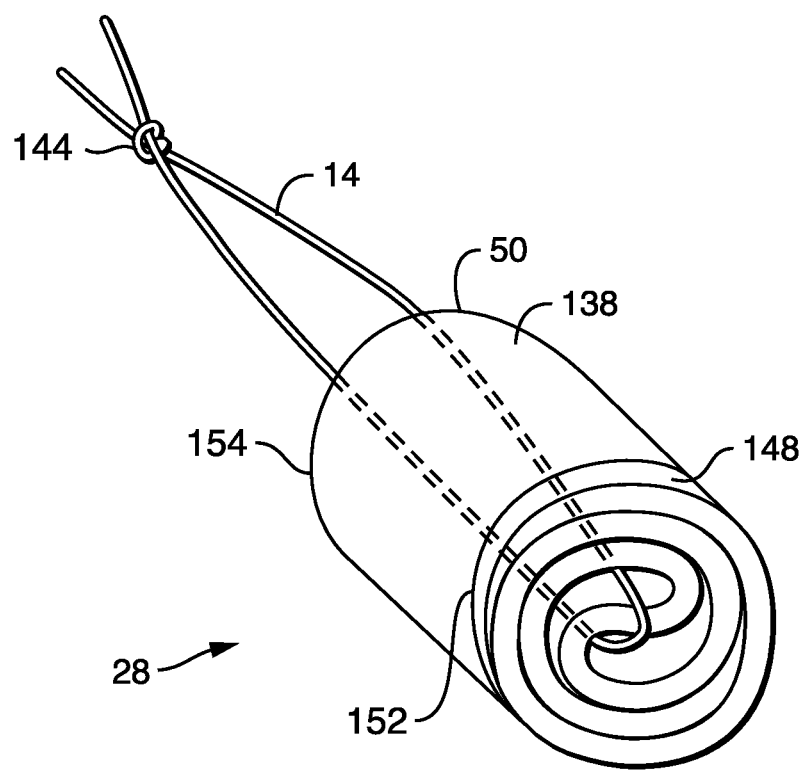
FIG. 25 is a perspective view of an embodiment in which a cover is bonded to a blank.
Figure 26A:
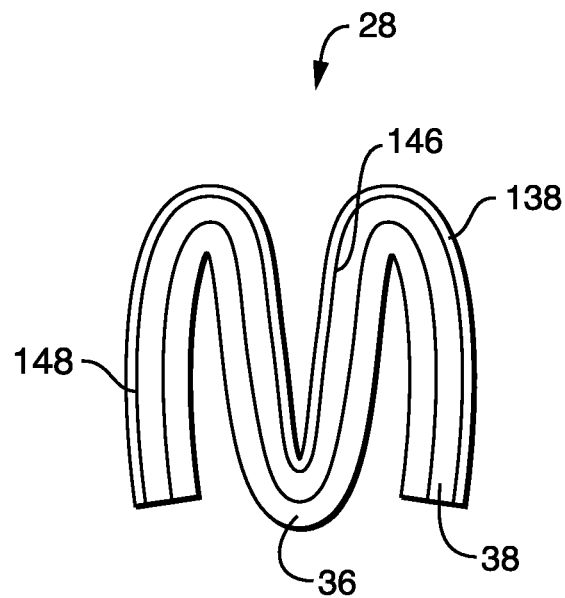
FIG. 26A is an end view of an embodiment in which a cover is bonded to a blank.
Figure 26B:
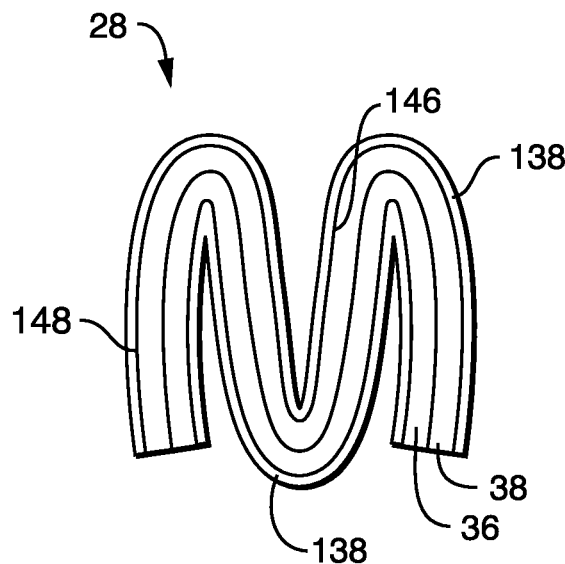
FIG. 26B is an end view of an embodiment in which a cover is bonded to a blank.
Figure 27:
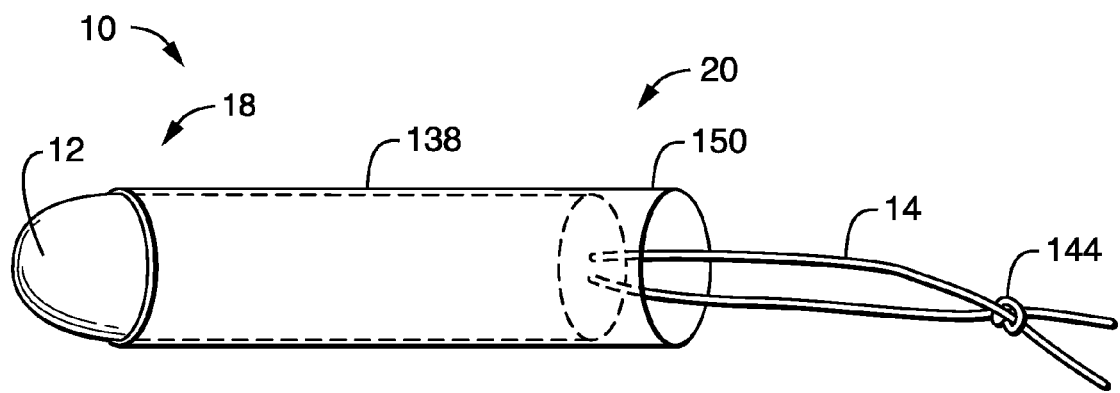
FIG. 27 is a side view of an embodiment of a tampon wherein the cover defines a skirt.

In various embodiments, at least a portion of a cover 138 can cover a body facing surface 148, a portion of an interior surface 146, or combinations thereof of a blank 28. FIG. 25 provides an illustration of a non-limiting embodiment in which at least a portion of a cover 138 can cover a portion of a body facing surface 148 of a blank 28, such as a softwind. As illustrated in FIG. 26A, in an embodiment, at least a portion of a cover 138 can cover a portion of an interior surface 146 of a blank 28 when a fleece 30 is compressed, such as, for example, via side compression. As illustrated in FIG. 26A, in an embodiment, at least a portion of the cover 138 can cover a combination of the body facing surface 148 and the interior surface 146 of a blank 28. The interior surface 146 of the blank 28 can result from folding, rolling, or otherwise manipulating the fleece 30 into the blank 28. It is to be understood that in an embodiment, the interior surface 146 of the pledget 12 may come into contact with the vaginal walls as the tampon 10 can expand when contacted by body fluids. The expansion of the tampon 10 can, therefore, cause exposure of the interior surface 146 of the pledget 12 to the vaginal walls and body fluid. As illustrated in FIG. 26B, in an embodiment two covers 138 can be in communication with a fleece 30 which can be compressed, such as, for example, via side compression, into a blank 28. As illustrated in FIG. 26B, in such an embodiment, at least a portion of each of the covers 138 can cover a portion of an interior surface 146 of a blank 28 of a pledget 12. In such an embodiment, at least a portion of each of the covers 138 can cover a combination of the body facing surface 148 and the interior surface 146 of a blank 28 of a pledget 12. In various embodiments, the cover 138 can extend beyond the withdrawal end 20 of the pledget 12 to form a skirt 150 as illustrated in FIG. 27. It is to be understood that, in an embodiment, the cover 138 can extend beyond the insertion end 18 of a pledget 12.

In an embodiment, the cover 138 can have two edges, 152 and 154. As noted above, the cover 138 can be bonded to a nonwoven ribbon 32, a fleece 30, a blank 28, or a pledget 12. In an embodiment, during the bonding process, at least one of the edges, 152 or 154, of the cover 138 can be substantially aligned with one of the transverse edges, such as transverse edges 48 and 50 or 64 or 66. In an embodiment, during the bonding process, the cover 138 can be bonded to the nonwoven ribbon 32, the fleece 30, the blank 28, or the pledget 12 so as to produce a spiral or helical pattern on the resulting pledget 12. In an embodiment, the two edges, 152 and 154, can be perpendicular to the longitudinal axis 16 of a pledget 12. In an embodiment, the two edges, 152 and 154, can be positioned in a direction parallel to the longitudinal axis 16 of a pledget 12 or at any other angle to the longitudinal axis 16 of a pledget 12 such as may occur if the cover 138 is spirally wound about the pledget 12. Thus, while the cover 138 and the edges, 152 and 154, may be discussed herein in an orientation perpendicular to the longitudinal axis 16 of a pledget 12, one of ordinary skill will be able to recognize how to provide a cover 138 and edges, 152 and 154, in an orientation parallel with the longitudinal axis 16 of a pledget 12 or in an orientation having any other angle in relation to the longitudinal axis 16 of a pledget 12.

In an embodiment, the cover 138 can have uniform properties. In an embodiment, the cover 138 can have non-uniform properties. In such an embodiment, the cover 138 can have regions with differing properties which can be coordinated to increase or decrease absorbency and/or level of expansion of the tampon 10. For example, a region can be more hydrophilic or hydrophobic in comparison to another region of the cover 138. In an embodiment, the hydrophilic region of the cover 138 could substantially cover the portion of the tampon 10 that would contact the menses first to increase menses absorption and as a result increase expansion of that portion of the tampon 10.

The regions of the cover 138 with differing properties may be produced by various methods. One example of a method is by treating the regions of the cover 138 with chemical finishes, such as hydrophilic or hydrophobic finishes that make the regions either more hydrophilic or more hydrophobic, respectively. The regions can also be mechanically altered. Any method known in the art of mechanically altering nonwovens or films can be used. Mechanically altering includes, but is not limited to, processes such as ring-rolling, corrugating, SELFing, and aperturing.

The composition of the cover 138 can also provide for differing properties of the cover 138. Different regions of the cover 138 can be produced from different materials. For example, one region of the cover 138 may have a higher concentration of rayon than another section of the cover 138 to make that region more hydrophilic. Materials could be selected for any property desired for a cover 138 known in the art, such as a selection of a material to provide a region of the cover 138 with greater extensibility. In an embodiment, the cover 138 may include multiple discrete pieces that are bonded together to form a single cover 138. The discrete pieces can have differing properties such as described above. In an embodiment, the discrete pieces of the cover 138 may form the different regions of the cover 138 such as described above. In such an embodiment, one discrete piece may form one region and another discrete piece may form a different region of the cover 138. The discrete pieces can be bonded by any method known to one of ordinary skill in the art, such as sewing, adhesive, thermal bonding, fusion bonding, or combinations thereof.

Figure 28:
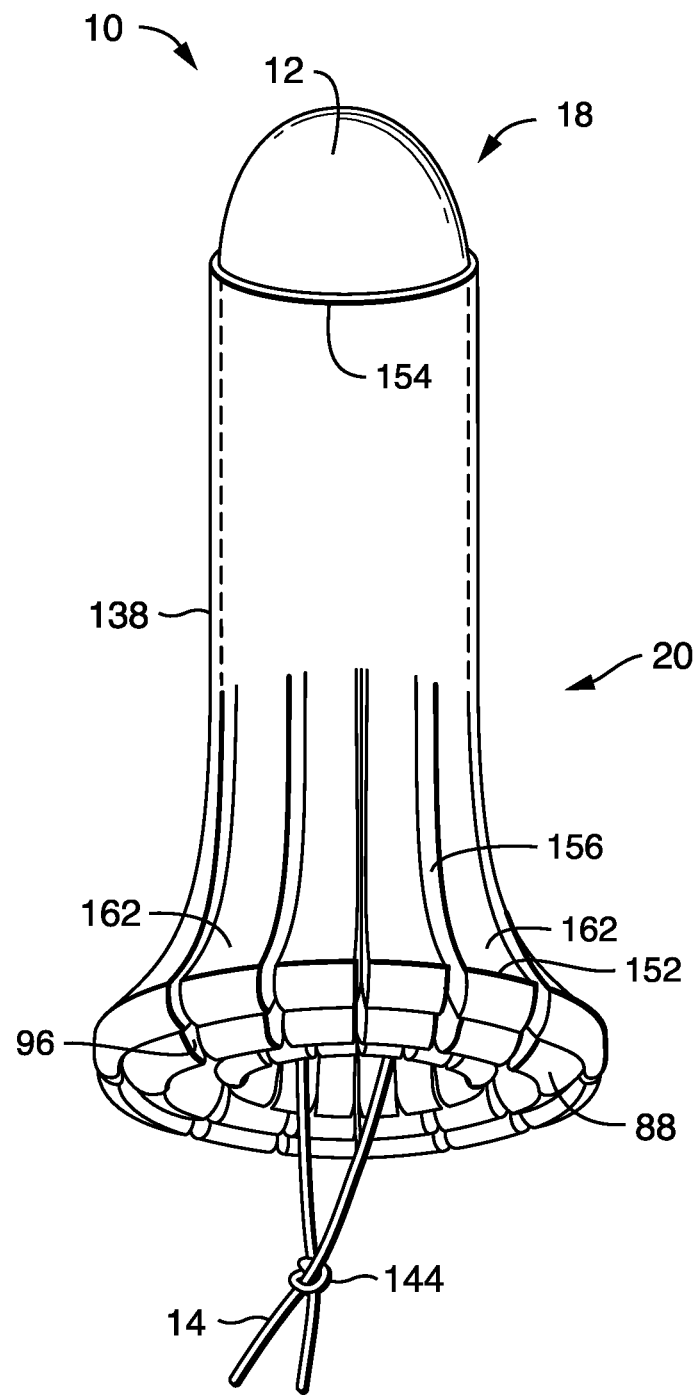
FIG. 28 is a perspective view of an embodiment of a tampon in an activated configuration.

As illustrated in FIG. 28, in an embodiment, the cover 138 can have at least one slit 156. In an embodiment, the slit(s) 156 can be located between the two edges, 152 and 154, of the cover 138. In such an embodiment, the slit 156 can form a cover contact element 162. In an embodiment, the slit(s) 156 can be associated with at least one of the edges, 152 and/or 154. In an embodiment, at least one slit 156 can be associated with at least one of the edges, 152 and/or 154, and at least one slit 156 can be located between the two edges, 152 and 154. In an embodiment in which slits 156 are associated with at least one of the edges, 152 and 154, the cover 138 can have at least two slits 156 which can form a cover contact element 162. The cover contact element 162 can come into contact with the walls of the vagina and can direct fluid flow towards the tampon 10. In an embodiment, the cover 138 can have at least one cover contact element 162. In an embodiment, the cover 138 can have at least 1, 2, 3, 4, 5, 6, 7, 8, 9, or 10 cover contact elements 162. In an embodiment, the cover 138 can have from about 1, 2, 3, 4, 5, 6, 7, 8, 9, or 10 to about 11, 12, 13, 14, 15, 16, 17, 18, 19 or 20 cover contact elements 162. In an embodiment, a cover contact element 162 can be oriented perpendicular to the longitudinal axis 16 of a tampon 10. In an embodiment, a cover contact element 162 can be oriented parallel with the longitudinal axis 16 of a tampon 10. In an embodiment, a cover contact element 162 can be oriented at any angle as desired to the longitudinal axis 16 of a tampon 10.

In an embodiment, a slit 156 of the cover 138 can be substantially aligned with a slit 96 of a layer(s), such as layer(s) 36 and/or 38. In an embodiment, a slit 156 can be offset from a slit 96 of a layer(s), such as layer(s) 36 and/or 38. In an embodiment, a slit 156 of a cover 138 can be substantially aligned with a slit 96 of a layer(s), such as layer(s) 36 and/or 38, and a slit 156 of a cover 138 can be offset from a slit 96 of a layer(s), such as layer(s) 36 and/or 38. In the non-limiting embodiment illustrated in FIG. 28, the slits 156 of the cover 138 can be substantially aligned with the slits 96 of a layer of the absorbent structure 34. In such an embodiment, a slit 156 in the cover 138 can allow the contact element 88 to expand in a direction away from the tampon 10 and to deform and flex away from the tampon 10. In an embodiment, the length of a slit 156 in the cover 138 can be any length deemed suitable. In an embodiment, the length of a slit 156 in the cover 138 can be substantially similar to the length 98 of a slit 96 in a layer(s), such as layer(s) 36 and/or 38. In an embodiment, a width between two successive slits 156 in the cover 138 can be any width as deemed suitable. In an embodiment, the width between two successive slits 156 in the cover 138 can be substantially similar to the width 102 between two successive slits 96 in one of the layers, 36 and/or 38. In an embodiment, the length of a slit 156 and the width between two successive slits 156 in the cover 138 can be substantially similar to or different from the length 98 of a slit 96 and the width 102 between slits 96 in a layer(s), such as layer(s) 36 and/or 38, when the slits 156 in a cover 138 substantially align with the slits 96 in a layer(s), such as layer(s) 36 and/or 38, or when the slits 156 in a cover 138 are offset from the slits 96 in a layer(s), such as layer(s) 36 and/or 38. In an embodiment, a cover contact element 162 can substantially align with a contact element 88 of a layer(s), such as layer(s) 36 and/or 38. In an embodiment, a cover contact element 162 can be offset from a contact element 88 of a layer(s), such as layer(s) 36 and/or 38.

In various embodiments, the pledget 12 may be subject to further processing to result in a finished tampon. For example, the pledget 12 may be joined with a withdrawal aid 14 and/or applicator.

Figure 29:
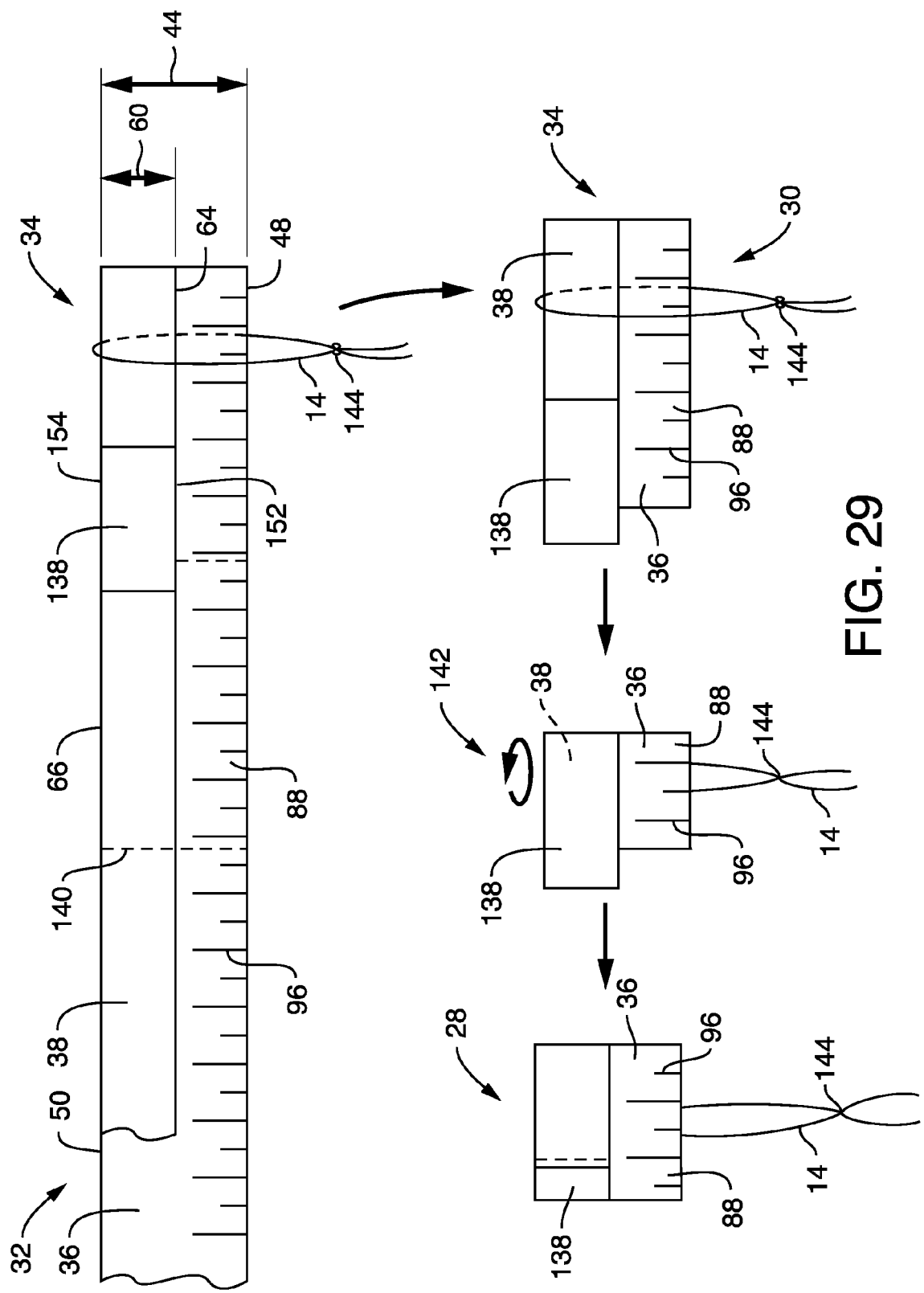
FIG. 29 is a perspective view of an embodiment of a method of manufacturing an absorbent structure.

The withdrawal aid 14 may be attached to the pledget 12 in any suitable manner. For example, an opening can be formed through the pledget 12 (and cover 138 if provided) so as to provide a means for attaching a withdrawal aid 14. In various embodiments, the withdrawal aid 14 can be attached to the fibrous material before or after it is compressed into the pledget 12. The withdrawal aid 14 can be attached to the fibrous material and then looped upon itself. As illustrated in FIG. 29, the withdrawal aid 14 can be associated with the nonwoven ribbon 32 and can further be associated with the fleece 30. In such an embodiment, the withdrawal aid 14 can be, as illustrated, wound with the fleece 30 in the formation of a blank 28. A knot 144 can be formed near the free ends of the withdrawal aid 14 to assure that the withdrawal aid 14 does not separate from the fibrous material. The knot 144 can also serve to prevent fraying of the withdrawal aid 14 and to provide a location where a woman can grasp the withdrawal aid 14 when she is ready to remove the tampon 10 from her vagina.

The withdrawal aid 14 can be constructed from various types of threads or ribbons. A thread or ribbon can be made from 100% cotton fibers and/or other materials in whole or part. The withdrawal aid 14 can be bonded to the absorbent fibers with or without tying. The withdrawal aid 14 can have any suitable length and/or the withdrawal aid 14 can be dyed and/or treated with an anti-wicking agent, such as wax, before being secured to the pledget 12.

FIG. 29 provides a non-limiting illustration of an embodiment of a method of manufacturing a blank 28 of the present disclosure. A nonwoven ribbon 32 which can have an absorbent structure 34, can ultimately result in a blank 28. In an embodiment, the absorbent structure 34 of the nonwoven ribbon 32 can be a single layer. In an embodiment, the absorbent structure of the nonwoven ribbon 32 can be multi-layered. The absorbent structure 34 of the nonwoven ribbon 32, can be manufactured via a multi-bank laydown process, a process whereby pre-formed fibrous material layers are bonded together, or a combination thereof. During the manufacture of the absorbent structure 34 of the nonwoven ribbon 32, the absorbent structure 34 can have any configuration of layers as desired. During the manufacture of a multi-layered absorbent structure 34 of a nonwoven ribbon 32, the layers can be configured into any desired configuration, such as, but not limited to, the configurations described and illustrated herein. The nonwoven ribbon 32 illustrated in FIG. 29 can have an absorbent structure 34 which can have two layers, 36 and 38, which can be placed into communication with each other. In an embodiment, the two layers, 36 and 38, can be bonded to each other after they are placed into communication with each other. Each of the layers, 36 and 38, can have transverse edges, such as transverse edges 48 and 50 of layer 36 and 64 and 66 of layer 38. In the non-limiting illustration of FIG. 29, transverse edge 50 of first layer 36 can be substantially aligned with transverse edge 66 of second layer 38. As illustrated in the non-limiting illustration of FIG. 29, the first layer 36 can have a first length 44 which can be longer than a second length 60 of second layer 38. As noted herein, the two layers, 36 and 38, can be arranged into any desired configuration including, but not limited to, any of the configurations described and illustrated herein. As described herein, at least one slit 96 can be incorporated into at least one of the layers, 36 and/or 38, forming the absorbent structure 34 of the nonwoven ribbon 32. The slit(s) 96 can be incorporated into at least one of the layer(s), such as layer(s) 36 and/or 38, prior to, after, or while placing one of the layers of the absorbent structure 34 into communication with another layer of the absorbent structure 34. In the non-limiting illustration of FIG. 29, the slit(s) 96 can be associated with a transverse edge of one of the layers, 36 and/or 38, such as transverse edge 48 of layer 36. As described herein, in an embodiment, at least one slit 96 can be incorporated into at least one of the layers, 36 and/or 38, in such a configuration so as to not be associated with one of the transverse edges of either of the layers, 36 and/or 38. In the non-limiting embodiment illustrated, a first layer 36 having two transverse edges, 48 and 50, can be provided and a plurality of slits 96 can be associated with transverse edge 48 to form at least one contact element 88. As discussed herein, in an embodiment, a contact element 88 can be associated with any of the transverse edges or can be located between the transverse edges of a layer. As illustrated in the non-limiting embodiment shown in FIG. 29, the contact elements 88 can be associated with transverse edge 48 of layer 36. The nonwoven ribbon 32 can also be provided with a cover 138 and a withdrawal aid 14. As noted above, to create a blank 28, the nonwoven ribbon 32 can be separated into individual units of fleece 30. The separation of the nonwoven ribbon 32 into individual units of fleece 30 can occur by any suitable method such as stretching, perforating, or cutting such as with the use of a die cutter or a knife cutter, and the like. As illustrated in FIG. 29, the nonwoven ribbon 32 can be provided with perforation cuts 140 which can facilitate the separation of the nonwoven ribbon 32 into individual units of fleece 30. The cover 138 can be provided to the nonwoven ribbon 32 before the nonwoven ribbon 32 has been separated into an individual unit of fleece 30 and can be provided in such a way as to span at least a portion of the perforation cuts 140.

As noted above, the nonwoven ribbon 32 can be separated into individual units of fleece 30 which can be rolled, stacked, folded or otherwise manipulated into blanks 28 before the blanks 28 are formed into pledgets 12. For example, suitable menstrual tampons may include "cup" shaped pledgets like those disclosed in U.S. Publication No. 2008/0287902 to Edgett and U.S. Pat. No. 2,330,257 to Bailey; "accordion" or "W-folded" pledgets like those disclosed in U.S. Pat. No. 6,837,882 to Agyapong; "radially wound" pledgets like those disclosed in U.S. Pat. No. 6,310,269 to Friese; "sausage" type or "wad" pledgets like those disclosed in U.S. Pat. No. 2,464,310 to Harwood; "M-folded" tampon pledgets like those disclosed in U.S. Pat. No. 6,039,716 to Jessup; "stacked" tampon pledgets like those disclosed in U.S. 2008/0132868 to Jorgensen; or "bag" type tampon pledgets like those disclosed in U.S. Pat. No. 3,815,601 to Schaefer.

As illustrated in FIG. 29, the fleece 30 can be radially wound into a blank 28, such as a softwind. As illustrated in FIG. 29, the nonwoven ribbon 32 can be separated into individual units of fleece 30, which can undergo a radial winding process, illustrated by the partially wound unit 142, to result in a blank 28. A suitable method for making "radial wound" pledgets is disclosed in U.S. Pat. No. 4,816,100 to Friese. The radial winding method can also include a method for forming the blank into a pledget like that disclosed in U.S. Pat. No. 6,310,269 to Friese. Suitable methods for making "W-folded" pledgets are disclosed in U.S. Pat. No. 6,740,070 to Agyapong; U.S. Pat. No. 7,677,189 to Kondo; and U.S. 2010/0114054 to Mueller. A suitable method for making "cup" pledgets and "stacked" pledgets is disclosed in U.S. 2008/0132868 to Jorgensen.

In various embodiments, the blank 28 can be formed into a pledget 12. In an embodiment, forming the blank 28 into a pledget 12 can include a compressing step which can utilize any suitable means and apparatus. For example, the compressing step may utilize a plurality of dies which reciprocate relative to one another so as to form a mold cavity therebetween. When the blank 28 (e.g., a softwind) is positioned within the mold cavity, the dies may be actuated so as to move tangent to or towards one another, tangent to or towards the blank 28 and compress the blank 28. The blank 28 may be compressed any suitable amount. For example, the blank 28 may be compressed at least about 25%, 50%, or 75% of the initial dimensions. For example, a blank 28 can be reduced in diameter to approximately ¼ of the original diameter. The cross-sectional configuration of the resultant pledget 12 may be circular, ovular, rectangular, hexagonal, or any other suitable shape.

In various embodiments, the compressing step may not include any additional heat applied to the pledget 12. In other words, the blank 28 can be compressed into a pledget 12 without external heat being applied to the compression equipment or the blank 28. In various embodiments, the compressing step may incorporate or may be followed by one or more additional stabilization steps. This secondary stabilization can serve to maintain the compressed shape of the pledget 12. In general, the secondary stabilization step can create hydrogen bonds between the absorbent fibers and/or may further strengthen the entanglement of the absorbent fibers to maintain the shape of the compressed pledget 12.

Figure 30:
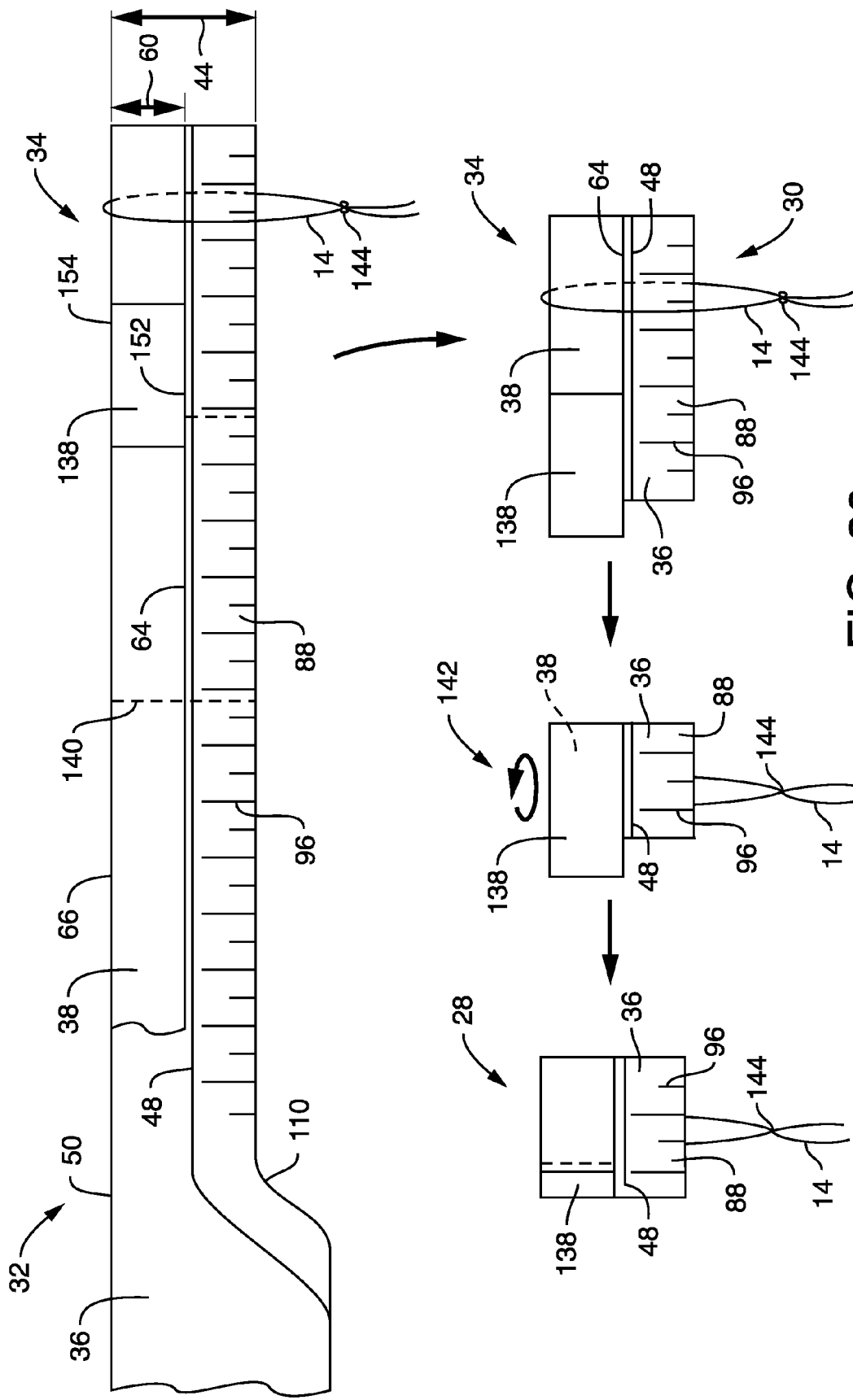
FIG. 30 is a perspective view of an embodiment of a method of manufacturing an absorbent structure.

FIG. 30 provides a non-limiting illustration of an embodiment of a method of manufacturing a nonwoven ribbon 32 of the present disclosure. A nonwoven ribbon 32 which can have an absorbent structure 34, can ultimately result in a blank 28. In an embodiment, the absorbent structure 34 of the nonwoven ribbon 32 can be a single layer. In an embodiment, the absorbent structure of the nonwoven ribbon 32 can be multi-layered. As described herein, the absorbent structure 34 of the nonwoven ribbon 32, can be manufactured via a multi-bank laydown process, a process whereby pre-formed fibrous material layers are bonded together, or a combination thereof. During the manufacture of the absorbent structure 34 of the nonwoven ribbon 32, the absorbent structure 34 can have any configuration of layers as desired. During the manufacture of a multi-layered absorbent structure 34 of a nonwoven ribbon 32, the layers can be configured into any desired configuration, such as, but not limited to, the configurations described and illustrated herein. The nonwoven ribbon 32 illustrated in FIG. 30 can have an absorbent structure 34 which can have two layers, 36 and 38, which can be placed into communication with each other. In an embodiment, the two layers, 36 and 38, can be bonded to each other after having been placed into communication with each other. Each of the layers, 36 and 38, can have transverse edges, such as transverse edges 48 and 50 of layer 36 and 64 and 66 of layer 38. In the non-limiting illustration of FIG. 30, transverse edge 50 of first layer 36 can be substantially aligned with transverse edge 66 of second layer 38. As illustrated in the non-limiting illustration of FIG. 30, the first layer 36 can have a first length 44 which can be longer than a second length 60 of second layer 38. As noted herein, the two layers, 36 and 38, can be arranged into any desired configuration including, but not limited to, any of the configurations described and illustrated herein. In the non-limiting embodiment illustrated, a fold 110 can be incorporated into first layer 36. The fold 110 can bring transverse edge 48 of layer 36 into communication with transverse edge 64 of layer 38. As discussed herein, additional folds can be incorporated into the absorbent structure 34 as desired and into any configuration as desired. As described herein, at least one slit 96 can be incorporated into at least one of the layers, 36 and/or 38, forming the absorbent structure 34 of the nonwoven ribbon 32. The slit(s) 96 can be incorporated into at least one of the layer(s), such as layers 36 and/or 38, prior to, after, or while placing one of the layers of the absorbent structure 34 into communication with another layer of the absorbent structure 34. In the non-limiting illustration of FIG. 30, the slit(s) 96 can be associated with the fold 110 of first layer 36. As illustrated in FIG. 30, a plurality of slits 96 can be associated with the fold 110 of first layer 36 to form at least one contact element 88. As discussed herein, in an embodiment, a contact element 88 can be associated with any of the transverse edges, a fold, or can be located between the transverse edges of a layer. As described herein, in an embodiment, at least one slit 96 can be incorporated into at least one of the layers, 36 and/or 38, in such a configuration so as to not be associated with one of the transverse edges of either of the layers, 36 and/or 38. The nonwoven ribbon 32 can also be provided with a cover 138 and a withdrawal aid 14. As noted above, to create a blank 28, the nonwoven ribbon 32 can be separated into individual units of fleece 30. The separation of the nonwoven ribbon 32 into individual units of fleece 30 can occur by any suitable method such as stretching, perforating, or cutting such as with the use of a die cutter or a knife cutter, and the like. As illustrated in FIG. 30, the nonwoven ribbon 32 can be provided with perforation cuts 140 which can facilitate the separation of the nonwoven ribbon 32 into individual units of fleece 30. The cover 138 can be provided to the nonwoven ribbon 32 before the nonwoven ribbon 32 has been separated into an individual unit of fleece 30 and can be provided in such a way as to span at least a portion of the perforation cuts 140.

As illustrated in FIG. 30, the fleece 30 can be radially wound into a blank 28, such as a softwind. As illustrated in FIG. 30, the nonwoven ribbon 32 can be separated into individual units of fleece 30, which can undergo a radial winding process, illustrated by the partially wound unit 142, to result in a blank 28. As described herein, in various embodiments, the blank 28 can be formed into a pledget 12.

In various embodiments, the pledget 12 may be subject to further processing to result in a finished tampon. For example, the pledget 12 may be joined with a withdrawal aid 14, such as described herein, and/or applicator.

The withdrawal aid 14 may be attached to the pledget 12 in any suitable manner. For example, an opening can be formed through the pledget 12 (and cover 138 if provided) so as to provide a means for attaching a withdrawal aid 14. In various embodiments, the withdrawal aid 14 can be attached to the fibrous material before or after it is compressed into the pledget 12. The withdrawal aid 14 can be attached to the fibrous material and then looped upon itself. As illustrated in FIGS. 29 and 30, the withdrawal aid 14 can be associated with the nonwoven ribbon 32 and can further be associated with the fleece 30. In such an embodiment, the withdrawal aid 14 can be, as illustrated, wound with the fleece 30 in the formation of a blank 28. A knot 144 can then be formed near the free ends of the withdrawal aid 14 to assure that the withdrawal aid 14 does not separate from the fibrous material. The knot 144 can also serve to prevent fraying of the withdrawal aid 14 and to provide a place or point where a woman can grasp the withdrawal aid 14 when she is ready to remove the tampon 10 from her vagina.

In various embodiments, the tampon 10 may also include one or more additional features. For example, the tampon 10 may include a "protection" feature as exemplified by U.S. Pat. No. 6,840,927 to Hasse, U.S. 2004/0019317 to Takagi, U.S. Pat. No. 2,123,750 to Schulz, and the like. In some embodiments, the tampon 10 may include an "anatomical" shape as exemplified by U.S. Pat. No. 5,370,633 to Villalta, an "expansion" feature as exemplified by U.S. Pat. No. 7,387,622 to Pauley, an "acquisition" feature as exemplified by U.S. 2005/0256484 to Chase, an "insertion" feature as exemplified by U.S. Pat. No. 2,112,021 to Harris, a "placement" feature as exemplified by U.S. Pat. No. 3,037,506 to Penska, or a "removal" feature as exemplified by U.S. Pat. No. 6,142,984 to Brown.

FIGS. 31-40 illustrate one suitable embodiment of an apparatus, indicated generally at 200, and method for making a tampon, and more particularly for making a cover, such as a web (or ribbon) of cover material used to cover the pledget, such as pledget 12, in forming the tampon 10. As illustrated schematically in FIGS. 31 and 32, the apparatus 200 is for making a web of cover material from a pair of web materials, referred to broadly herein as a first or base material and a second or absorbent material. It is contemplated that the second material can have other properties in addition to or instead of being absorbent, such as, but not limited to wicking and/or wiping.

Materials suitable for the base material and the absorbent material are described above. For example, materials suitable for the base material can include materials described above with respect to the cover 138 and materials suitable of the absorbent material can include materials described above with respect to the absorbent structure 34. In one suitable embodiment, the absorbent material has a tensile strength in the MD direction of 2-38 Newtons per inch of width, a tensile strength in the CD direction of 0.13-6 Newtons per inch of width, and a thickness in the range of 0.25-1 mm. Suitably, the material used for the absorbent material is bondable, has a minimal Poisson's ratio, is hydrophilic, is drapable and soft, and has minimal linting. In one suitable embodiment, the base material, which is water permeable, has a tensile strength in the MD direction at of at least 5-75 Newtons per inch of width, a tensile strength in the CD direction of 1-20 Newtons per inch. Suitably, the material used for the base material is bondable, has a minimal Poisson's ratio, is drapable and soft, and has minimal linting.

Figure 31:
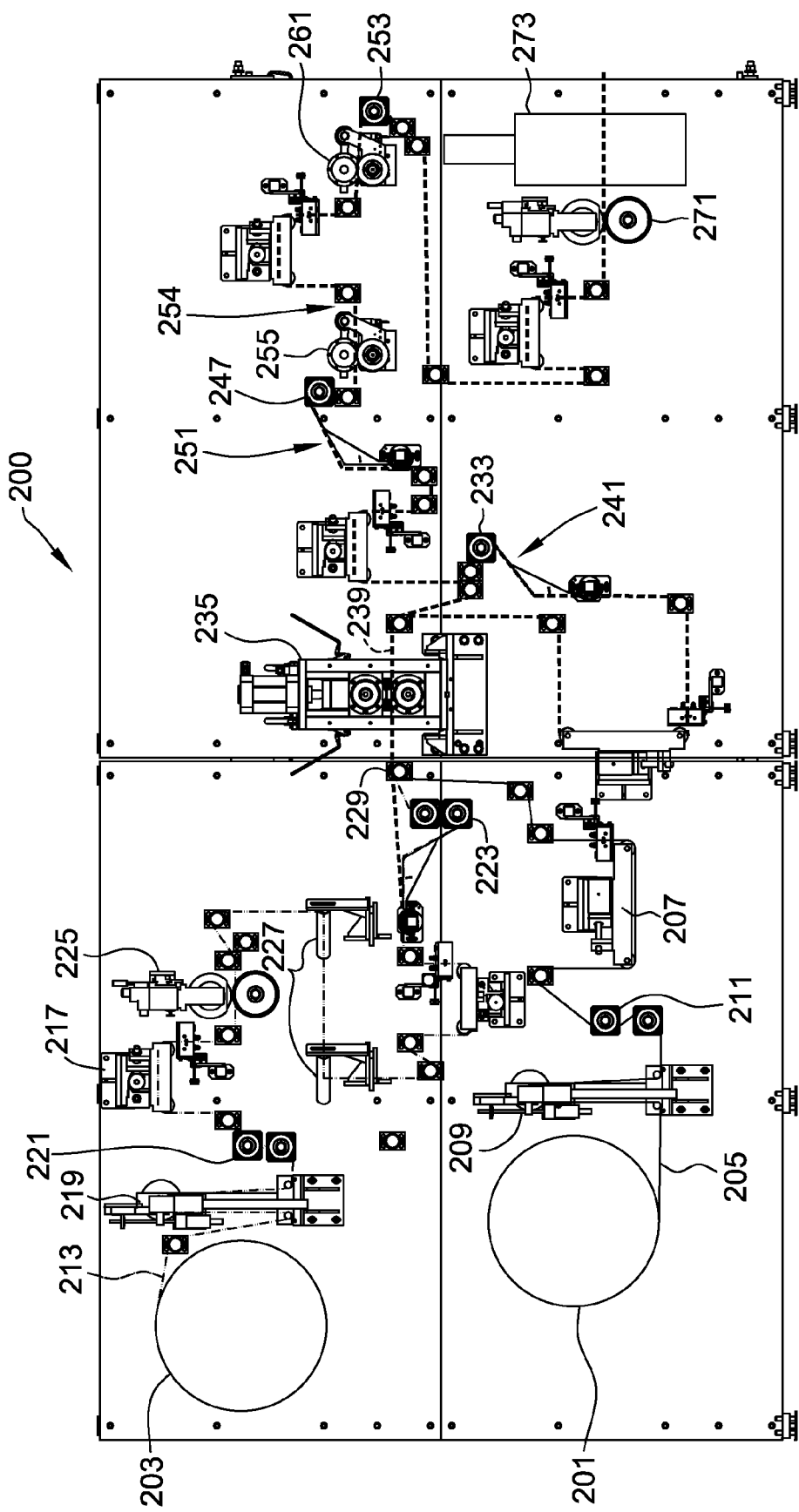
FIG. 31 is a schematic of one suitable embodiment of an apparatus for making a cover material used in forming the tampon.
Figure 32:
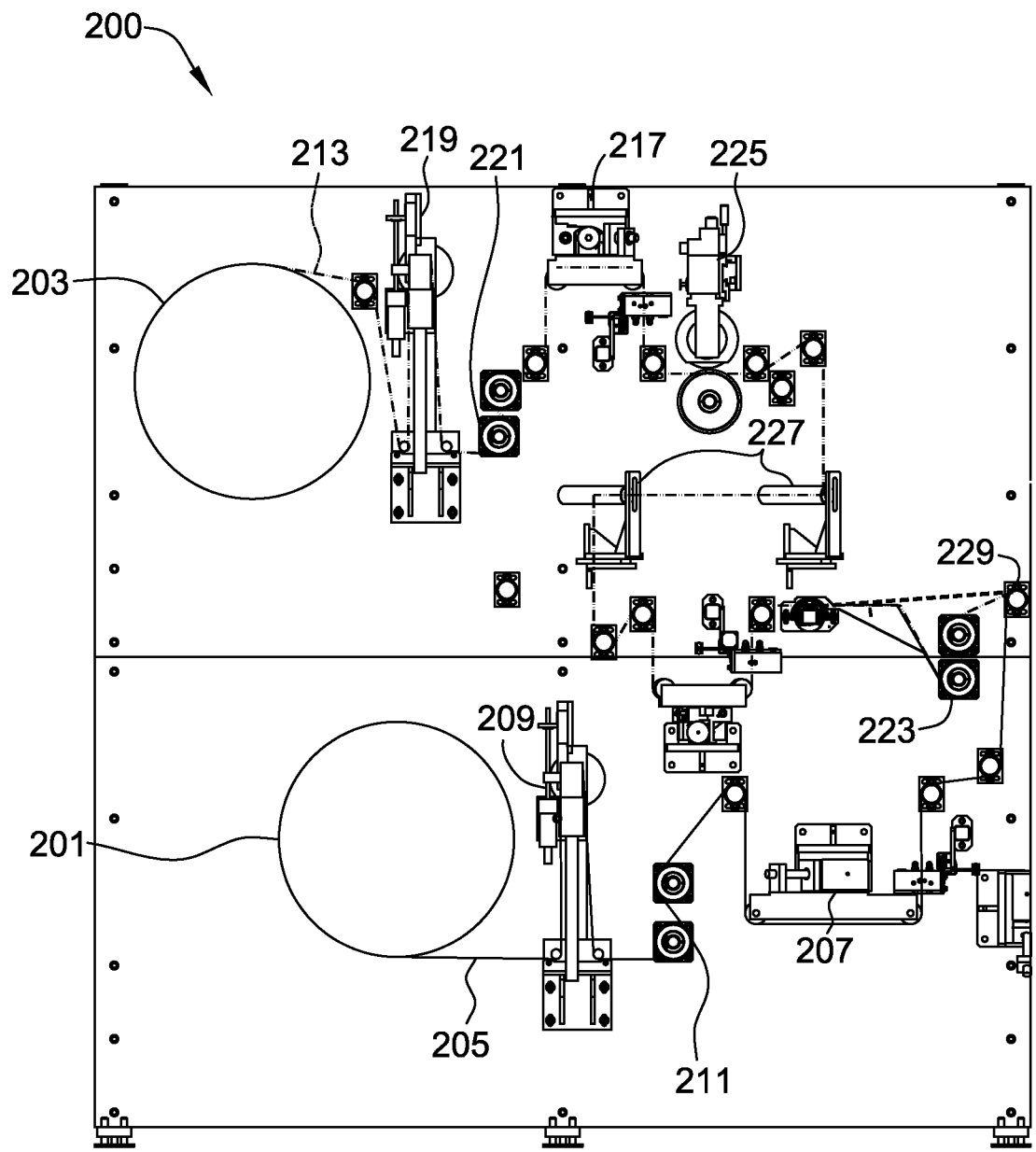
FIG. 32 is an enlarged schematic of a portion of the apparatus of FIG. 31.

As seen in FIGS. 31 and 32, the apparatus 200 includes a source of base material, such as a wound roll 201 comprising a wound or rolled continuous web 205 of base material, and a source of absorbent material, such as a wound roll 203 comprising a wound or rolled continuous web 213 of absorbent material. It is understood, however, that in other embodiments other suitable sources 201, 203 of base material and/or absorbent material may be used (e.g., blocks, boxes, bins, formed in-line).

In an embodiment, the web 205 of base material and the web 213 of absorbent material are unwound and moved throughout the apparatus in a machine direction (referenced throughout the various FIGs. as machine direction MD) (i.e., the direction in which the respective webs are moved forward through the apparatus). In the illustrated embodiment, the web 205 of base material has a width sufficient to simultaneously make a pair of side-by-side webs of cover material. For example, in one embodiment, the web 205 of base material has a width in the range of 100 mm (about four times the final width of the web of absorbent material) to about 150 mm (about six times the final width of the web of absorbent material), and more particularly about 110 mm. It is contemplated that the widths of the webs can be measured using any convention measuring technique including rulers, photoeyes, vision cameras, web width sensors, visual indicators, and combinations thereof.

The web 205 of base material is unwound from the roll 201 in the machine direction MD by a suitable drive member 211, and passes through a tensioning member 209 and guide rolls 207 following unwinding from the roll. Suitable drive members, tensioning members and guide rolls as used herein are conventional and thus not further described herein except to the extent necessary to disclose the present invention. The transverse, or cross-direction position of the web is established by the position of the unwind equipment (e.g., roll, etc.). Conventional centering components (e.g., shepherds, hooks, vertical idlers, and other suitable centering components) may be used to maintain the transverse or CD position of the web 205 relative to the machine direction MD. In addition to guide rolls, other conventional web handling components may be used to maintain the orientation and centering of the web as it moves through the apparatus, such as guide trays and the like. Suitable web guides and web guide controllers are commercially available, such as, the Fife web guiding system.

Thus, both the web 205 of base material and the web 213 of absorbent material are registered in both the MD and CD direction. In other words, both of the webs 205, 213 are aligned relative to one or more reference points. The one or more reference points can be a portion of the web 205, 213 itself, a portion of the other web, a component (or portion thereof) of the apparatus 200, and/or combinations thereof. In one suitable embodiment, CD registration of the webs 205, 213 is maintained within ±0-5 mm, and MD registration of webs is maintained within ±0-2 mm. The web 213 of absorbent material is centered at its desired location on the web 205 of base material within ±0-5 mm. Suitably, one or more inspection systems can be used to ensure proper CD and MD registration of the webs 205, 213.

In the illustrated embodiment, the web 213 of absorbent material on the roll 203 has a width sufficient to simultaneously make a pair of side-by-side webs of cover material. However, the width of the web 213 of absorbent material, in one embodiment, is also narrower than the width of the web 205 of base material. For example, in one embodiment the width of the web 213 of absorbent material on the roll 203 is in the range of about 25 mm to about 70 mm, and more particularly about 50 mm. In other embodiments, the web 205 of base material and the web 213 of absorbent material may have respective widths sufficient to make a single web of cover material, or more than two side-by-side webs of cover material. It is also contemplated that in other embodiments the relative widths of the web 205 of base material and the web 213 of absorbent material may be other than as described above.

The web 213 of absorbent material on the roll 203 is unwound from the roll in the machine direction thereof by a suitable drive member 221, and passes through a tensioning member 219 and guide rolls 217 following unwinding from the roll. The transverse, or cross-direction position of the web 213 is established by the position of the unwind equipment (e.g., roll, etc.). Conventional centering components (e.g., shepherds, hooks, vertical idlers, and other suitable centering components) may be used to maintain the transverse position of the web 213 relative to the machine direction MD. In addition to guide rolls, other conventional web handling components may be used to maintain the orientation and centering of the web 213 as it moves through the apparatus, such as guide trays and the like. Suitable web guides and web guide controllers are commercially available, such as, the Fife web guiding system.

A subsequent drive member 223 further moves the web 213 through a slitter 225 where the web of absorbent material is slit longitudinally (i.e., in the machine direction of the web) to form two separate side-by-side webs 213a, 213b of absorbent material, each corresponding to what will become a respective web of cover material upon association with the base material. The pair of absorbent material webs 213a, 213b is further passed over a series of turn rolls 227 to re-orient the webs and space them apart to a desired alignment for subsequent overlayment with the web 205 of base material. It is understood that the turn rolls 227 can be other suitable devices including, but not limited to, fife guides, guide trays. The webs 213a, 213b of absorbent material are directed over additional guide rolls, to the drive member 223 at which the webs of absorbent material are overlayed onto the web 205 of base material. It is contemplated that the webs 213a, 213b of absorbent material can be overlayed onto the web 205 of base material before or after the drive member 223. In one suitable embodiment, the webs 213a, 213b of absorbent material are overlayed onto the web 205 of base material at a bonder anvil.

Tension in each of the webs 205, 213, in one embodiment, is established using conventional devices, such as the respective drive members 211, 221, 223, spindle friction (not shown), dancer roll 209, 219, closed loop tension feedback device (not shown) and/or other suitable tension control devices. Web tensioning provides appropriate material strain in each of the webs 205, 213 to prevent wrinkling, curl and/or tearing during processing, and provides appropriate strain match during subsequent combining of the webs as described later herein.

Figure 34:
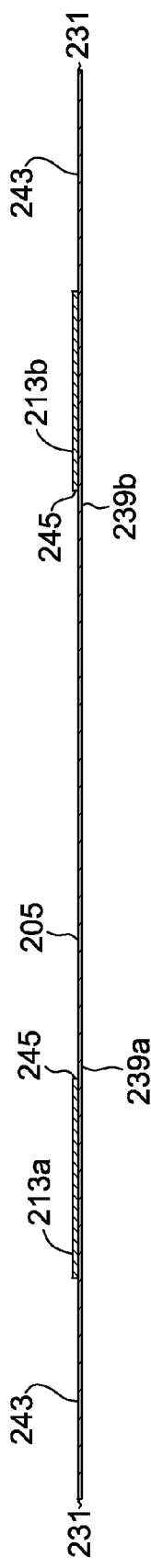
FIG. 34 is a cross-section showing a web of absorbent material overlayed onto a web of base material.
Figure 35:
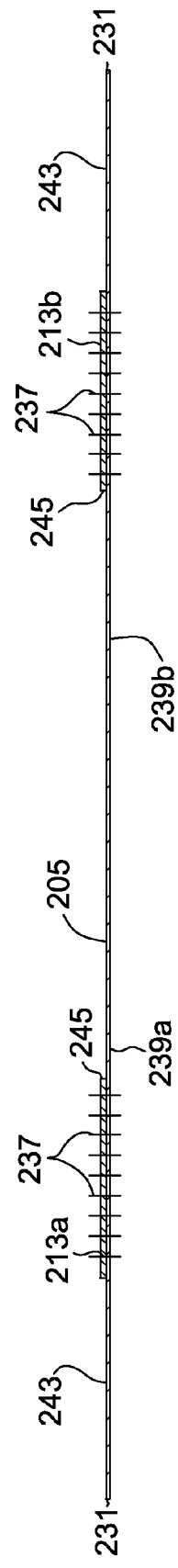
FIG. 35 is a cross-section similar to FIG. 34 but showing the web of absorbent material bonded to the web of base material.
Figure 36:
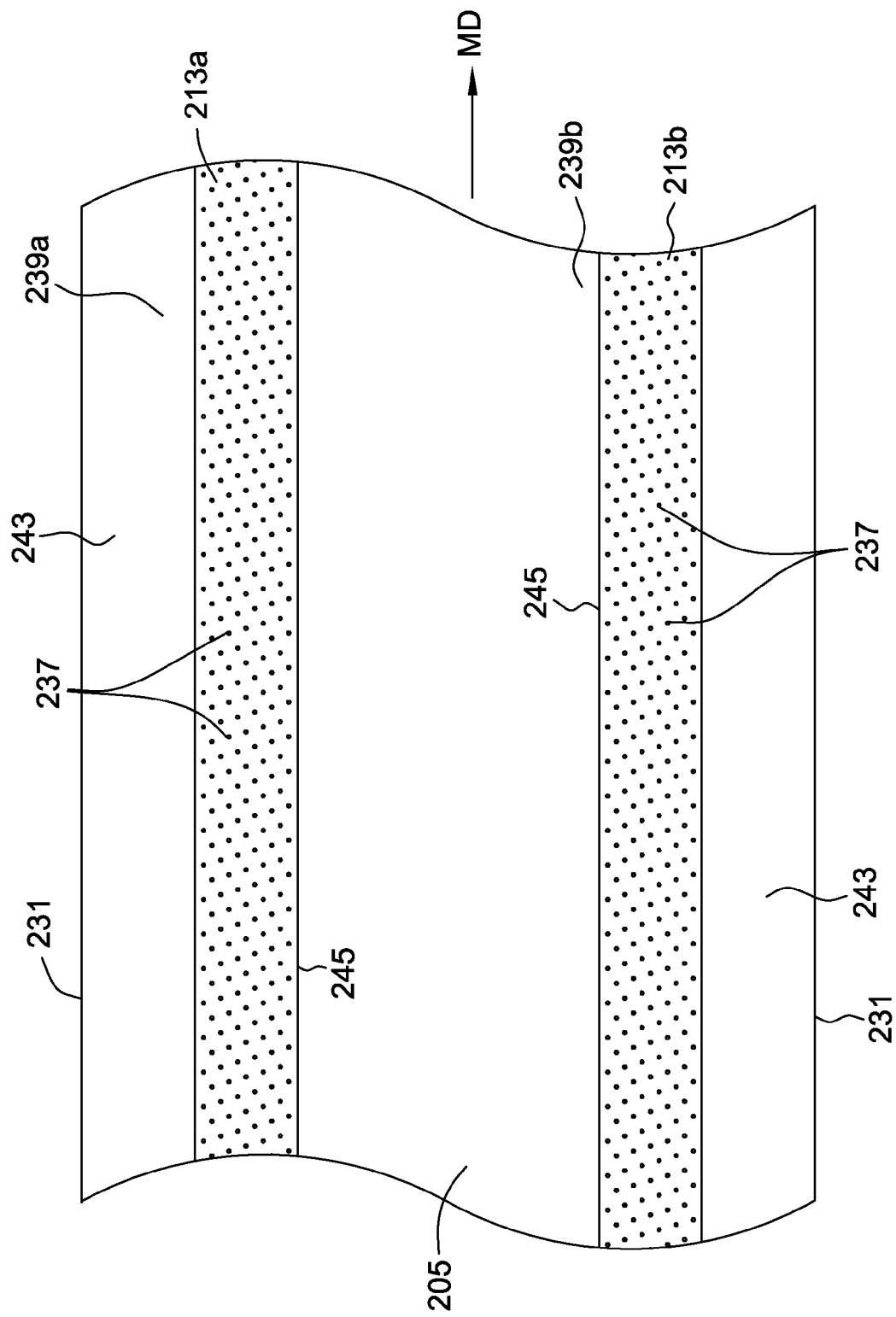
FIG. 36 is a fragmentary top view of the webs of FIG. 35.

With reference to FIG. 34, in one embodiment the webs 213a, 213b of absorbent material are overlayed onto the single web 205 of base material in transversely spaced (relative to the machine direction MD of the web) relationship with each other, but transversely inward from respective side edges 231 of the web of base material to allow for subsequent folding of the web of base material. For example, in one embodiment, the webs 213a, 213b of absorbent material are transversely spaced in the range of about 90 mm to about 130 mm from each other, and more particularly about 100 mm. The webs 213a, 213b are transversely spaced from the respective side edges 231 of the web 205 of base material a distance of about 0 mm to about 55 mm and more particularly about 55 mm, the reasons for which will become apparent. It is understood that the webs 213a, 213b of absorbent material can be transversely spaced from each and the respective side edge 231 by other suitable distances. The respective speeds of the webs 205, 213, i.e., the speed of movement in the machine direction MD, at the instant of overlayment are, in one embodiment, equal. In another embodiment, the webs 205, 213 may be moving at different speeds as overlayment occurs. The speeds of the webs 205, 213 can be controlled, for example, by servo motors, mechanical linkages, and the like.

It is contemplated that the webs 213a, 213b of absorbent material can be placed beneath the web 205 of base material or that the web of base material can be overlayed onto webs 213a, 213b of absorbent material. It is also contemplated that the webs 213a 213b of absorbent material can be placed on opposite faces of the web 205 of base material. For example, one of the webs 213a of absorbent material can be placed beneath the web 205 of base material and the other web 213b of absorbent material can be overlayed onto the web of absorbent material.

The overlayed webs 213a, 213b of absorbent material and web 205 of base material are then moved by a suitable drive member 233 through a bonding apparatus 235 for a bonding operation (broadly, a first securement) in which the webs of absorbent material are bonded (i.e., secured) to the web of base material. The bonding can occur by any method deemed suitable including, but not limited to, adhesives, heat bonding, vibration energy, mechanical bonding, chemical bonding, vacuum bonding, ultrasonic bonds, thermal bonds, pressure bonds, mechanical entanglement, hydroentanglement, microwave bonds, or any other conventional technique. The bonding can be continuous or it can be intermittent.

In one embodiment, the bonding apparatus is suitable for autogenous bonding, which as used herein means bonding provided by fusion and/or self-adhesion of fibers and/or filaments without an applied external adhesive or bonding agent. Autogenous bonding can be provided by contact between fibers and/or filaments while at least a portion of the fibers and/or filaments are semi-molten or tacky. Autogenous bonding may also be provided by blending a tackifying resin with the thermoplastic polymers used to form the fibers and/or filaments. Fibers and/or filaments formed from such a blend can be adapted to self-bond with or without the application of pressure and/or heat. Solvents may also be used to cause fusion of fibers and filaments which remain after the solvent is removed.

In one embodiment, the autogenous bonding is thermal point bonding, or pattern bonding, conducted by a suitable thermal point bonding apparatus 235 which involves passing the web between a heated calendar roll and an anvil roll. The calendar roll is usually, but not always, patterned in some way so that the entire fabric is not bonded across its entire surface, and the anvil roll is usually flat. As a result, various patterns for calendar rolls have been developed for functional as well as aesthetic reasons. For example, in the illustrated embodiment, the apparatus 235 bonds the webs 213a, 213b of absorbent materials to the web 205 of base material along a predetermined pattern of point bonds, such as the pattern of staggered point bonds 237 illustrated schematically in FIGS. 35 and 36. Other potential point bond patterns include staggered dashes, curved bond lines, or a combination of abstract, geometrical or realistic shapes and objects. Securing the webs 213a, 213b of absorbent materials to the web 205 of base material at this stage of manufacture allows for subsequent folding and processing of the webs while maintaining desired registration and alignment therebetween. In other embodiments, the first securement may be provided by thermal bonding, adhesive bonding or other suitable securement techniques. It is also understood that, in some embodiments, the webs 213a, 213b of absorbent material can be held in registration with the web 205 of base material using other suitable methods (e.g., vacuum conveyors).

Following this first securement operation, the secured webs 213a, 213b, 205 of absorbent material and base material together form a web 239 of cover material that in the illustrated embodiment is actually a pair of side-by-side (and at this stage connected) webs of cover material. The web 239 of cover material is then drawn by the drive member 233 through a folding station, which is generally indicated at 241. All of the folding stations of the illustrated apparatus 200 perform web alignment by creating a repeatable folded edge ensuring CD alignment of the web. In one embodiment, the folding station 241 is configured to fold transversely outward segments 243 of base material transversely inward over the entire respective web 213a, 213b of absorbent material to substantially enclose the web of absorbent material between opposed layers of the web of base material. Suitable folding devices include, without limitation, folding boards, folding skis, folding fingers, GEO folder and the like and combinations thereof. Additionally in an embodiment, the folding station 241 and first securement are designed to fold the web 205 of base material tightly around and in constant contact with the webs 213a, 231b of absorbent material. Thus, the web 205 of base material is inhibited from puckering, wrinkling or otherwise misalignment with the webs 213a, 213b of absorbent material.

Figure 37:
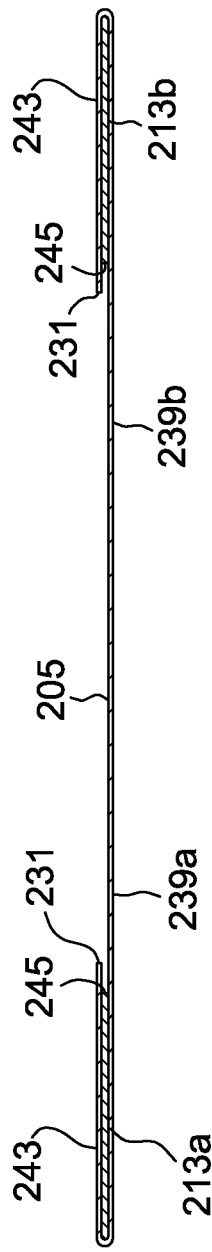
FIG. 37 is a cross-section similar to FIG. 35 but showing the web of base material being folded to cover the web of absorbent material.

FIG. 37 schematically illustrates the cross-section of the web 239 of cover material following folding at this folding station 241. In this embodiment, the inward folded transverse segments of the web 205 of base material extend transversely inward beyond inner side edges 245 of the respective webs 213a, 213b of absorbent material such that a portion of the opposed layers of the base material web face each other without any web of absorbent material therebetween. In other embodiments, the transverse segments of the web 205 of base material may extend transversely inward to the respective inner side edges 245 of the webs 213a, 213b of absorbent material, or extend short of the respective inner side edges of the webs of absorbent material.

The folded web 239 of cover material is subsequently drawn by a suitable drive member 247 through another folding station, generally indicated at 251, for additional folding. Suitable folding devices include, without limitation, folding boards, folding skis, folding fingers, GEO folder and the like and combinations thereof. In one embodiment, as illustrated schematically in FIG. 38, the already folded portion of the web 239 of cover material is further folded transversely inward upon itself. More particularly, it is folded over such that the web 213a, 213b of absorbent material is folded generally in half. In other embodiments, the already folded portion of the web 239 of cover material may be folded over upon itself more or less than illustrated in FIG. 38 without departing from the scope of this invention.

The folded web 239 of cover material is directed through a securement station, generally indicated at 255, comprising a bonding apparatus for a second bonding operation (broadly, a second securement) in which the webs 213a, 213b, 205 of absorbent material and base material are bonded (i.e., secured) together at the folded portions thereof in order to secure the web of cover material in its folded configuration. The bonding can occur by any method deemed suitable including, but not limited to, adhesives, heat bonding, vibration energy, mechanical bonding, chemical bonding, vacuum bonding, ultrasonic bonds, thermal bonds, pressure bonds, mechanical entanglement, hydroentanglement, microwave bonds, or any other conventional technique. The bonding can be continuous or it can be intermittent.

In one embodiment, the bonding apparatus is suitable for autogenous bonding. In an embodiment, the autogenous bonding is ultrasonic bonding performed by suitable ultrasonic bonding apparatus 255 that ultrasonically bonds all of the layers of the folded portions of the web 239 of cover material together in a predetermined bond pattern. For example, in the illustrated embodiment the apparatus 255 bonds the webs 213a, 213b, 205 of absorbent material and base material together at the folded portions thereof along a predetermined pattern of point bonds, such as the repeating but otherwise non-uniform (i.e., not symmetric in the machine direction and/or the transverse direction) snail-shaped pattern of point bonds illustrated schematically in FIG. 39. Other potential point bond patterns include staggered dots and/or dashes, curved bond lines, or a combination of abstract, geometrical or realistic shapes and objects. In other embodiments, the bond pattern may be any suitable bond pattern. For example, the bond pattern may be another suitable non-uniform bond pattern, or it may be any suitable uniform bond pattern.

The bond pattern in one embodiment is sufficient to provide an adequate number of bonds, or adequate bonded surface area, for each of the later-formed contact elements 162 (FIG. 28), e.g., formed by the slits 156 in the cover 138. In an embodiment, the bond pattern may be sufficient to provide an equal number of point bonds, or an even distribution of bonded surface area, over each of the later-formed contact elements 162. In another embodiment, the bond pattern may provide an unequal number of point bonds, or a non-uniform distribution of bonded surface area, over multiple later-formed contact elements 162.

In an embodiment, this second bonding (i.e., second securement) operation provides a bond having a bond strength that is greater than the bond strength provided by the first bonding (i.e., first securement) operation. It is understood that the bond strength, for example, can be controlled by pressure, energy, temperature, time and pattern used in the bonding process. For example, in the illustrated embodiment, the bond pattern provided by this second bonding operation has a higher bond point density and/or a higher bonded surface area than the bond pattern provided by the first bonding operation. In addition, the second bonding operation of the illustrated embodiment is operated at a temperature sufficient to melt the webs 213a, 213b of absorbent material and to the web 205 of base material whereas the first bonding operation is not operated at such a temperature.

Figure 33:
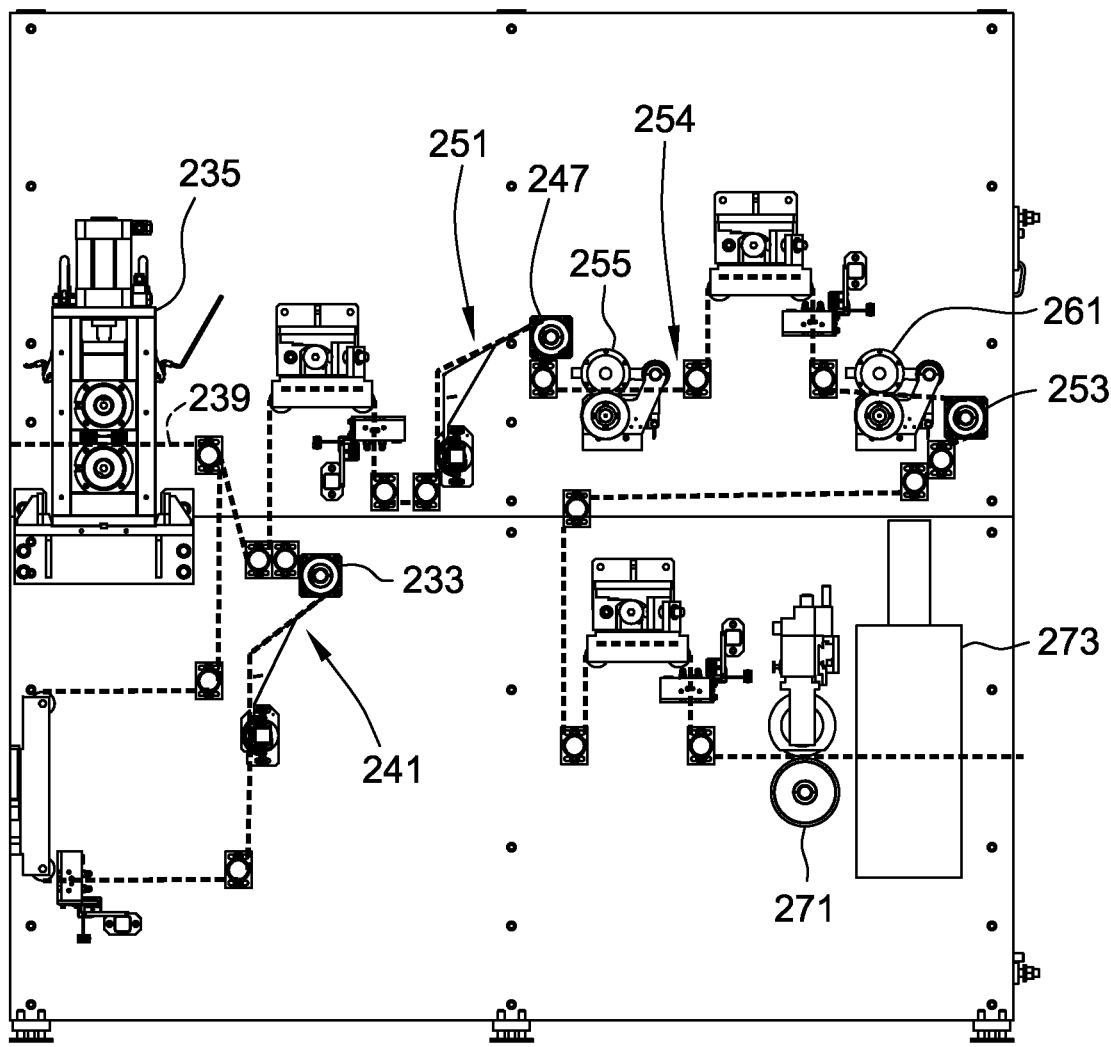
FIG. 33 is an enlarged schematic of another portion of the apparatus of FIG. 31.
Figure 40:
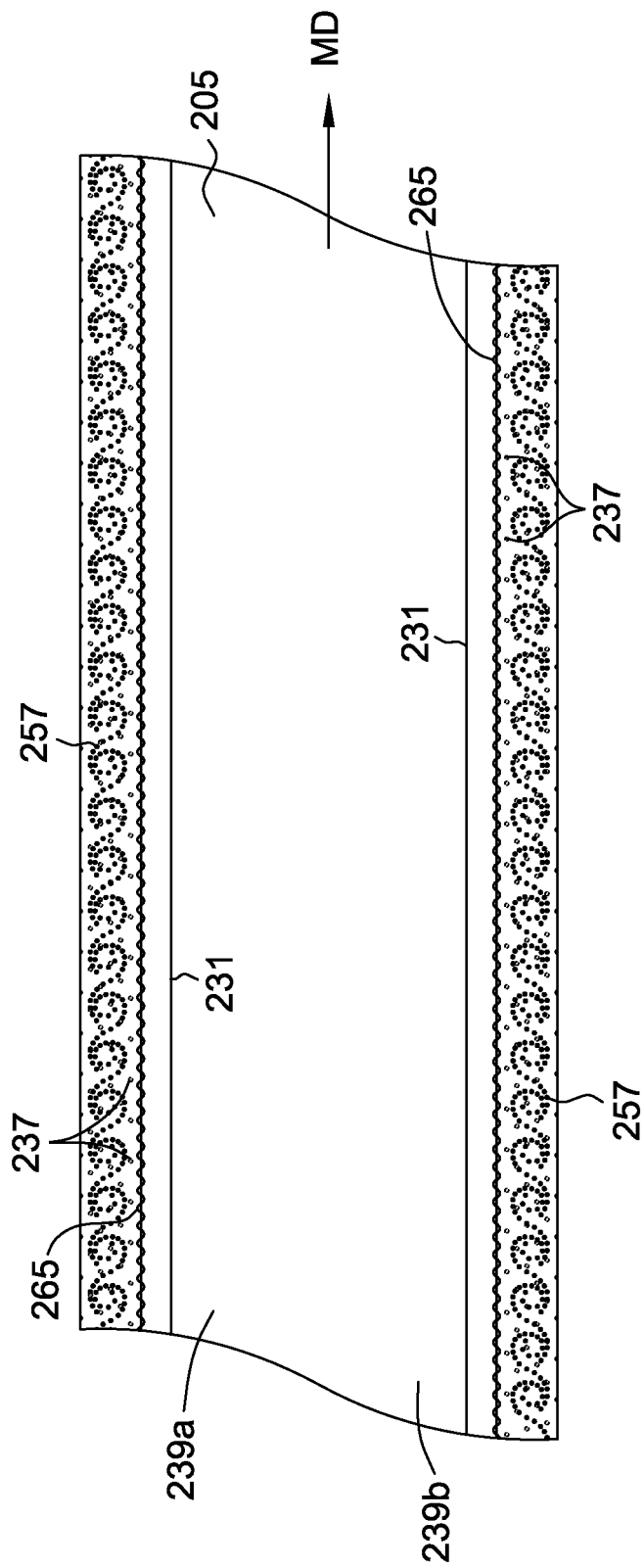
FIG. 40 is a fragmentary top view similar to FIG. 39 but showing inner edges of the folded outer portions of the webs being bonded.

In an embodiment, as illustrated in FIG. 33, the securement station further comprises an additional bonding apparatus 261. In the illustrated embodiment, the additional bonding apparatus 261 is also an ultrasonic bonding apparatus and is operable to bond the folded portions of the web 239 of cover material at a location that is at least in part different from the location at which the bond pattern is applied by the upstream bonding apparatus. More particularly, this bonding apparatus 261 bonds at least the folded portion of the web 205 of base material at which the opposed layers of base material face each other without intervening absorbent material therebetween. In one embodiment, as illustrated in FIG. 40, this additional bonding apparatus 261 additionally bonds all of the layers of the folded portion of the web 239 of cover material together generally along the inner side edges 245 of the respective webs 213*a*, 213*b* of absorbent material. This additional bonding operation securely encloses the webs 213*a*, 213*b* of absorbent material within the folded web 205 of base material.

In one embodiment, the bond pattern produced by this additional bonding operation is a uniform, generally sinusoidal (e.g., wave) bond pattern. In other embodiments, the bond pattern produced by this additional bonding operation may be any suitable uniform or non-uniform bond pattern. For example, in one embodiment, the bond pattern is an intermittent, offset stitch pattern to inhibit CD movement of the web as it passes through the apparatus 200. The bond strength provided by this additional bonding operation is also greater than the bond strength provided by the first bonding (i.e., first securement) operation.

Downstream of the securement station, the folded and bonded web 239 of cover material is subsequently drawn through a slitter 271 which is operable to slit the web of cover material into two discrete, side-by-side webs of cover material (FIGS. 31 and 33). For example, the web 239 of cover material may be slit along the transverse mid-point of the web, transversely inward of each of the folded portions of the web. In such an embodiment, each web 239 of cover material thus includes a folded portion and an unfolded portion comprised only of the base material.

In the embodiment illustrated in FIGS. 31 and 33, the webs 239*a*, 239*b* of cover material are further drawn through a die cutter 273 or other suitable cutting apparatus. The die cutter 273 is operable to cut slits in the folded portion of each of the webs of cover material, such as to form the slits 156 and corresponding contact elements 162 of the embodiment of FIG. 28. In an embodiment, the die cutter 273 may be operable to cut the slits in a pattern in which a set of equally spaced slits is cut into the folded portions of the webs 239 of cover material along a segment corresponding to the length of cover material to be applied to a single pledget to form a single tampon, followed by a relatively larger gap before the next set of equally spaced slits along a segment corresponding to the next length of cover material to applied to another pledget to form another tampon. In this embodiment, the gap can be used as a point of registration during further processing (e.g., cutting, bonding) of the webs 239*a*, 239*b* of cover material.

Figure 41:
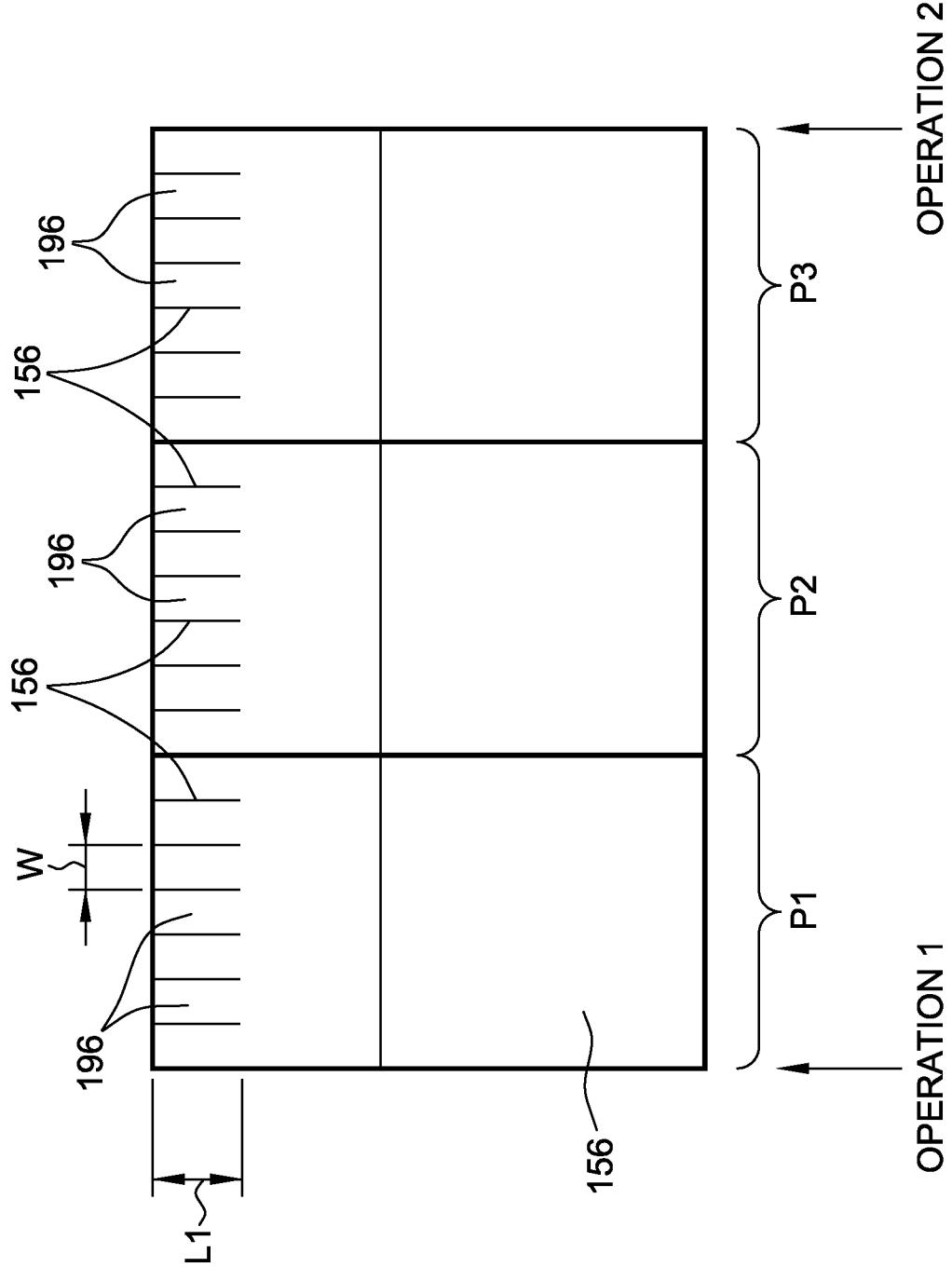
FIG. 41 is a top view of the webs illustrating slits cut into the web of absorbent material.

In another embodiment, which is illustrated in FIG. 41, the die cutter 273 may be operable to cut the slits 96 such that each slit is equally spaced in the folded portions of the webs 239 of cover material along a segment P1 corresponding to the length of cover material to be applied to a single pledget to form a single tampon, followed by the next set of equally spaced slits along a segment P2 corresponding to the next length of cover material to applied to another pledget to form another tampon. Thus, in this embodiment, each tampon 10 has the same number of contact elements 196 and each of the contact elements 196 has the same width W and the same length L1. In the illustrated embodiment, for example, each of the tampons 10 formed from the web 239 would have seven complete (i.e., whole) contact elements 196. It is understood, however, that number of contact elements 196 per tampon 10, the width W of each of the contact elements, and length L1 of each of the contact elements can differ. In yet another embodiment, the die cutter 273 may be omitted from the apparatus 200. In such an embodiment, the slits 96 can be formed in a later process as described in more detail below.

In an embodiment, after passing the die cutter 273 (or the slitter 271 if the die cutter is omitted) the webs 239*a*, 239*b* of cover material are wound onto respective rolls (not shown) for subsequent transport to a tampon making apparatus where the webs of cover material are each cut into discrete webs of cover material and applied about the circumference of an absorbent structure, such as a pledget 12, to form a tampon. In one suitable embodiment, one or both of the webs 239*a*, 239*b* of cover material is turned over about its centerline longitudinally before being wound into a roll. Winding of the webs 239*a*, 239*b* of cover material, in one suitable embodiment, can be done in a traverse spooling pattern and can be controlled (e.g., by steering devices, servos) such that the continuous longitudinal support structure of the web (unslit portion, or folded portion depending on die cutter placement) is registered to adjacent windings in the CD and radial layers in order to provide roll stability and prevent damage to the webs including any contact elements.

Figure 42:
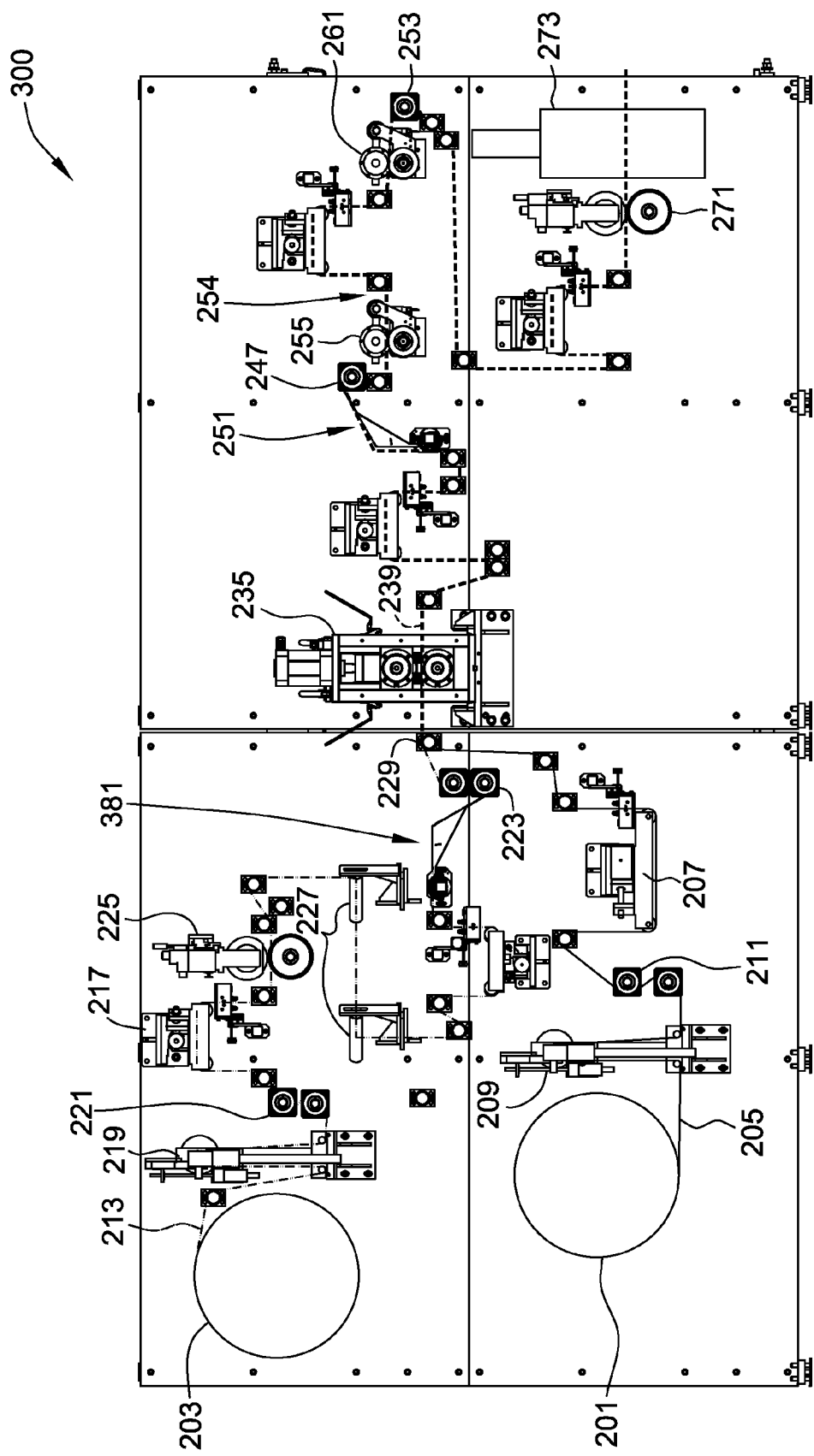
FIG. 42 is a schematic of another suitable embodiment of an apparatus for making a cover material used in forming the tampon.
Figure 43:
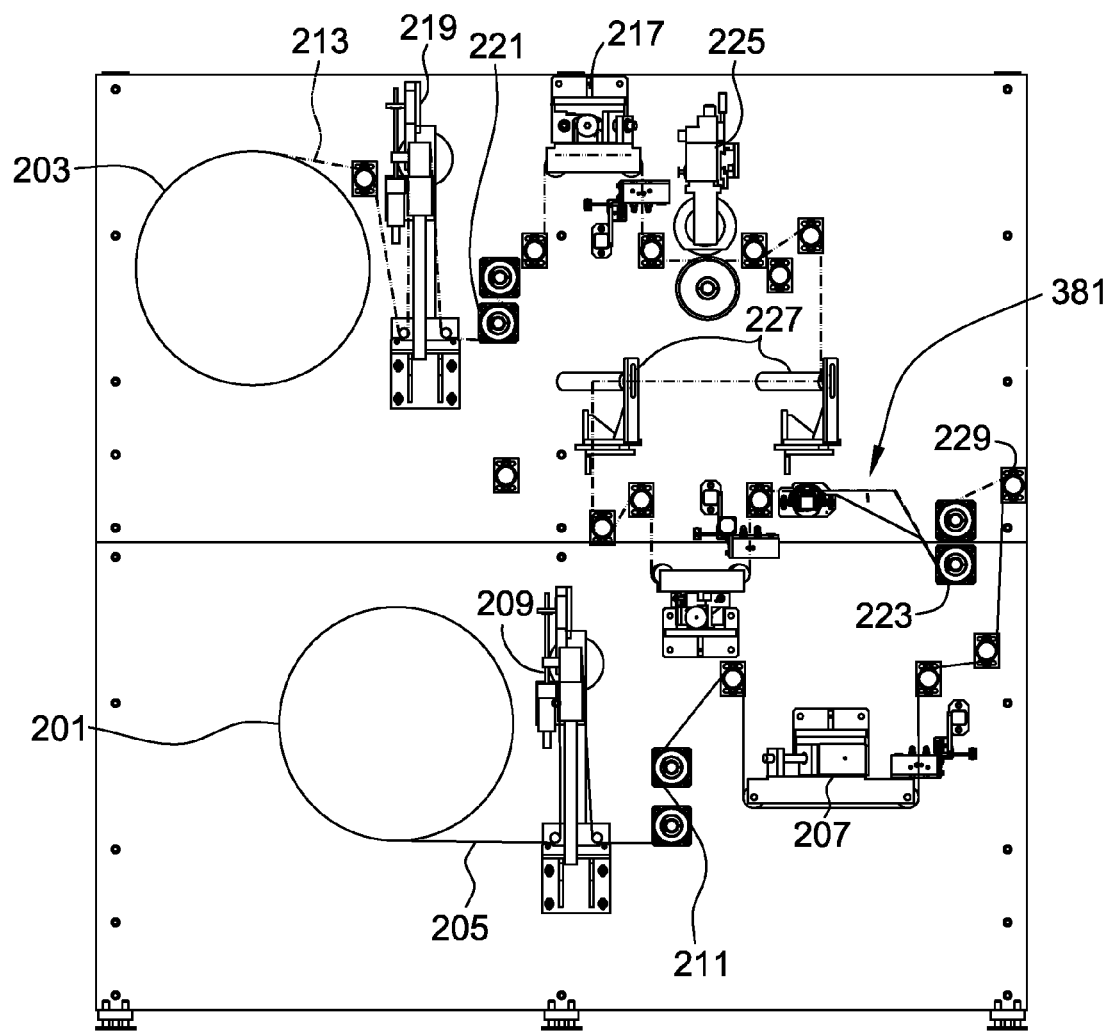
FIG. 43 is an enlarged schematic of a portion of the apparatus of FIG. 42.

FIGS. 42-50 illustrate another embodiment of an apparatus, indicated generally at 300, and method for making a tampon, and more particularly for making a cover, such as a web (or ribbon) of cover 138 used to cover the pledget, such as pledget 12, in forming the tampon. In this embodiment, a folding station, generally indicated at 381 in FIGS. 42 and 43, is disposed adjacent and prior to the drive member 223 (after the web 213 of absorbent material is split into the pair of side-by-side webs 213*a*, 213*b* of absorbent material) and the joint drive roll 229 (at which the webs of absorbent material are overlaid onto the web 205 of base material) in the machine direction of the webs of absorbent material. Suitable folding devices include, without limitation, folding boards, folding skis, folding fingers, GEO folder and the like and combinations thereof. At this initial folding station 381, each of the webs 213*a*, 213*b* of absorbent material is folded transversely inward upon at least a portion of itself. For example, in one embodiment, illustrated in FIG. 45, the transversely outermost one-third of each of the webs 213*a*, 213*b* of absorbent material is folded transversely inward at this initial folding station. In other embodiments, more or less than one-third of the outermost portion of each web 213*a*, 213*b* of absorbent material may be folded transversely inward over another portion thereof. In other embodiments, an innermost portion of each web 213*a*, 213*b* of absorbent material may be folded transversely outward over another portion thereof, or both an innermost portion and an outermost portion of each web of absorbent material may be folded over another portion thereof.

Figure 46:
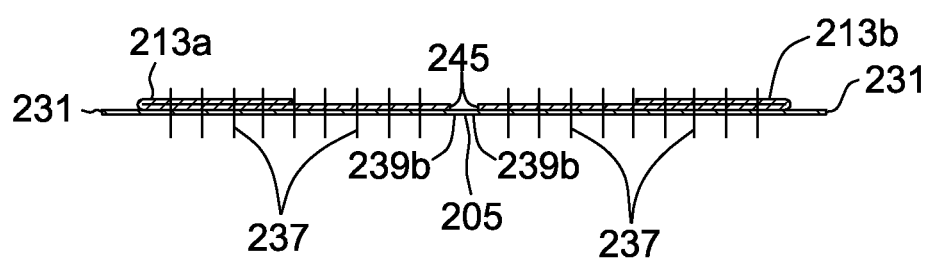
FIG. 46 is a cross-section showing the pair of webs of FIG. 45 overlayed onto and bonded to a web of base material.
Figure 47:
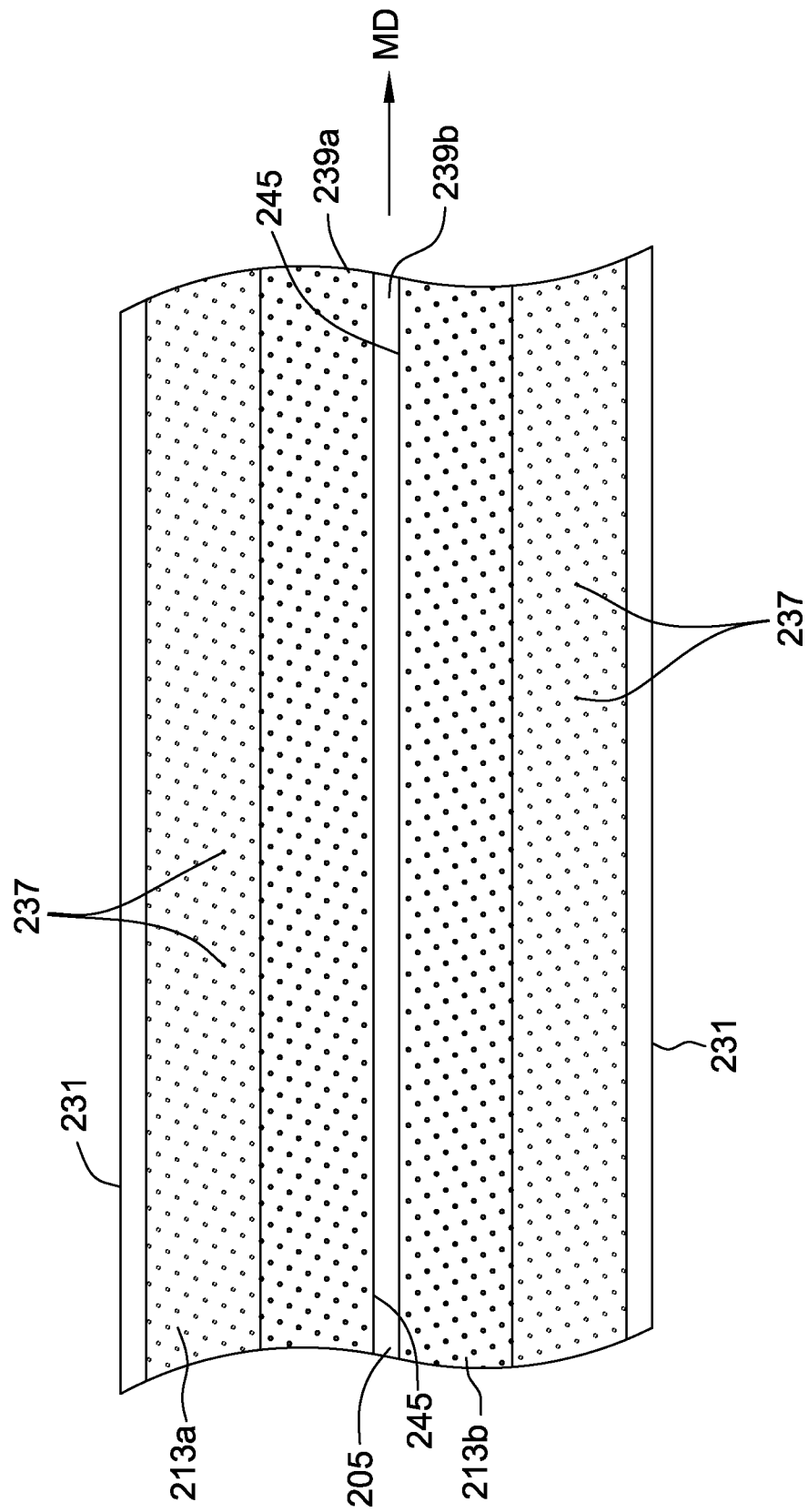
FIG. 47 is a fragmentary top view of the webs of FIG. 46.

The initially folded webs 213*a*, 213*b* of absorbent material are then drawn over the joint drive roll 229 where the webs of absorbent material are overlaid onto the web 205 of base material in transversely spaced (relative to the machine direction of the web) relationship with each other, but transversely inward from the respective side edges 231 of the web of base material (as illustrated in the embodiment of FIG. 46) for reasons which will become apparent. For example, in one embodiment the webs 213*a*, 213*b* of absorbent material are transversely spaced in the range of about 0 mm to about 55 mm from each other, and more particularly about 2 mm. The webs 213*a*, 213*b* are transversely spaced from the respective side edges 231 of the web 205 of base material a distance of about 0 mm to about 10 mm and more particularly about 3 mm.

The overlayed webs 213, 205 of absorbent material and web of base material are then moved by the drive member 233 through the bonding apparatus 235 for a bonding operation (broadly, a first securement) in which the webs of absorbent material are bonded (i.e., secured) to the web of base material. As discussed above, in one embodiment the bonding apparatus is a point bonding apparatus that bonds the webs of absorbent materials to the web of base material along a pattern of point bonds 237 as illustrated schematically in FIGS. 46 and 47. Securing the webs 213a, 213b of absorbent material to the web 205 of base material at this stage of manufacture allows for subsequent folding and processing of the webs while maintaining desired registration and alignment therebetween. In other embodiments, the first securement may be provided by thermal bonding, adhesive bonding or other suitable securement techniques.

Figure 44:
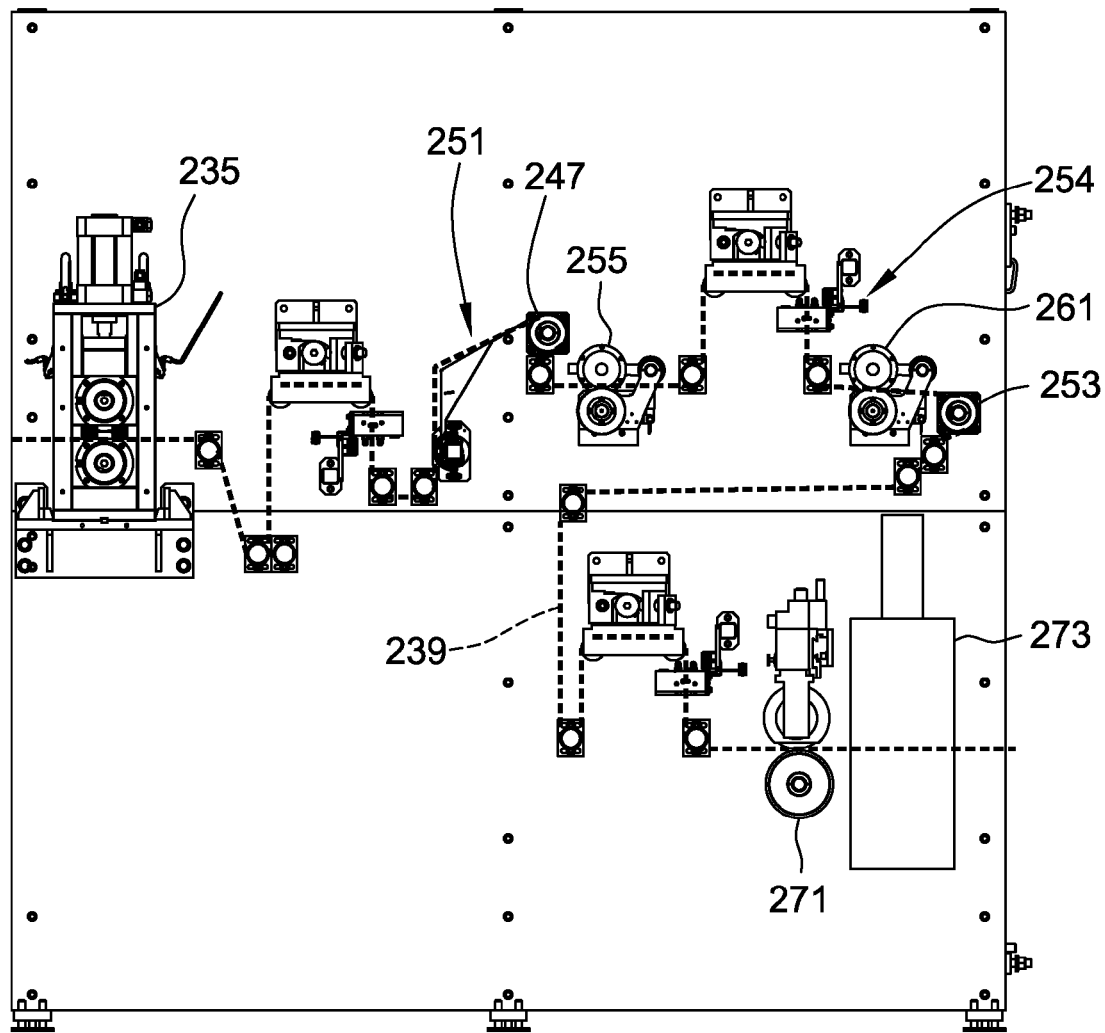
FIG. 44 is an enlarged schematic of another portion of the apparatus of FIG. 42.
Figure 45:
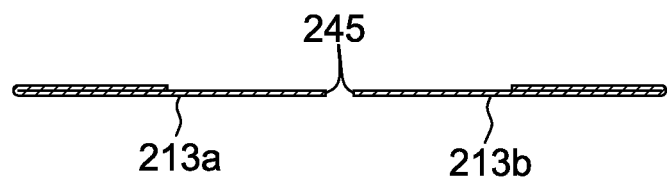
FIG. 45 is a cross-section of a pair of webs of absorbent material passing through the apparatus and having the outermost one-third of each of the webs folded inward.
Figure 48:
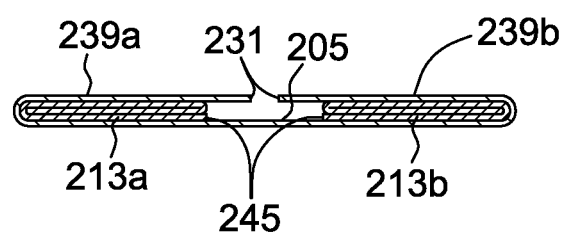
FIG. 48 is a cross-section showing the outer portions of the webs being folded inward.
Figure 49:
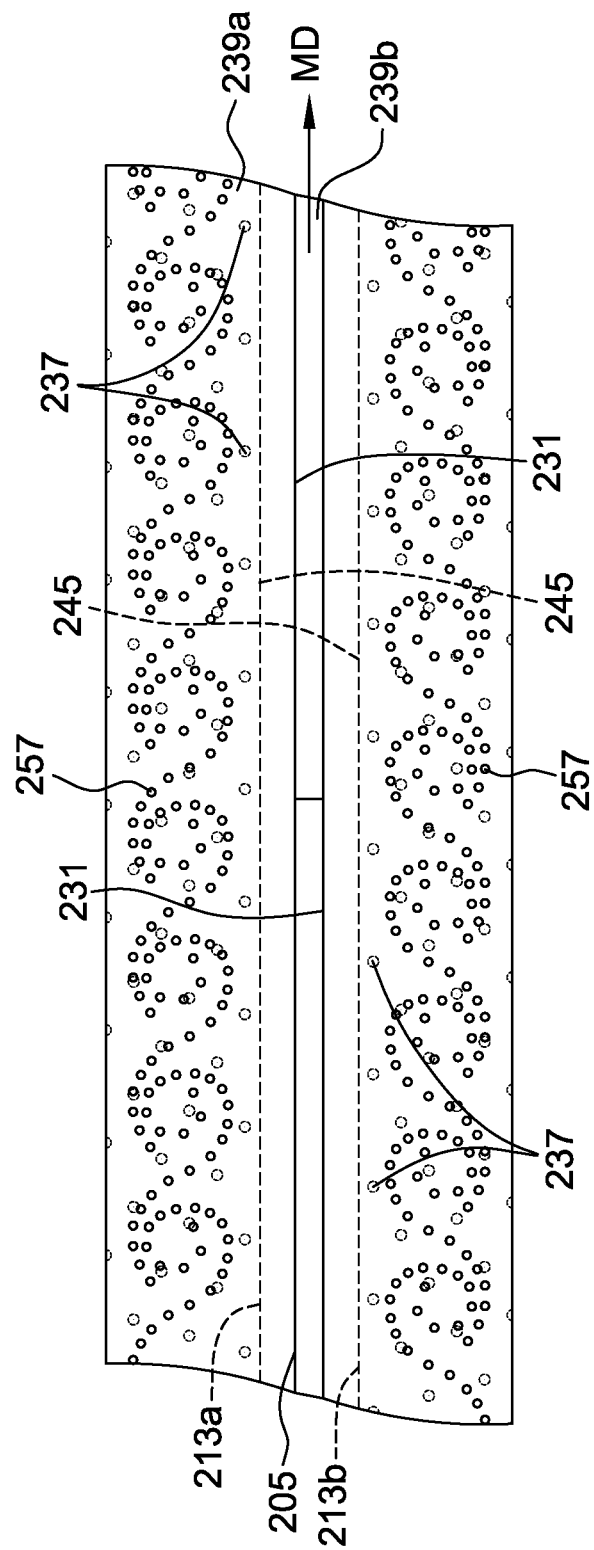
FIG. 49 is a fragmentary top view of the webs of FIG. 48 with the folded outer portions of the webs being bonded.

With reference to FIGS. 42 and 44, following this first securement operation, the secured webs 213, 205 of absorbent material and base material together form a web 239 of cover material that in the illustrated embodiment is actually a pair of side-by-side (and at this stage connected) webs 239a, 239b of cover material. The web 239 of cover material is then drawn by the drive member 247 through the folding station, generally indicated at 251. In one embodiment this folding station 251 is configured to fold each of the initially folded webs 213a, 213b of absorbent material transversely inward over at least another portion of itself to define three layers of the folded absorbent material as illustrated in FIG. 48. The web 205 of base material underlying each of the folded portions of the webs 213a, 213b of absorbent material is folded along with the webs of the absorbent material, with the side edges 231 of the web of base material extending transversely inward beyond the inner side edges 245 of the folded webs of absorbent material such that a portion of opposed layers of the base material web face each other without any absorbent material therebetween. In other embodiments, the webs 213a, 213b of absorbent material may be folded other than in segments of equal width. In another embodiment, the side edges 231 of the web 205 of base material may extend transversely inward to the respective inner side edges 245 of the webs 213a, 213b of absorbent material, or extend short of the respective inner side edges of the webs of absorbent material.

The drive member 253, which is disposed downstream of the folding station 251, also draws the folded web 239 of cover material through a securement station, generally indicated at 254, comprising a bonding apparatus 255 for a second bonding operation (broadly, a second securement) in which the webs 213, 205 of absorbent material and base material are bonded (i.e., secured) together at the folded portions thereof in order to secure the web of cover material in its folded configuration. In one embodiment, the bonding apparatus 255 is an ultrasonic bonding apparatus that ultrasonically bonds all of the layers of the folded portions of the web of cover material together in a predetermined bond pattern 257. In one embodiment, illustrated in FIG. 49, the bond pattern is a generally non-uniform bond pattern (i.e., not symmetric in the machine direction and/or the transverse direction), such as the illustrated snail-shaped bond pattern. In other embodiments, the bond pattern may be any suitable bond pattern. For example, the bond pattern may be another suitable non-uniform bond pattern, or it may be any suitable uniform bond pattern.

The bond pattern in one embodiment is sufficient to provide an adequate number of bonds, or adequate bonded surface area, for each of the later-formed contact members 162 (FIG. 28), e.g., formed by the slits 156 in the cover 138. In an embodiment, the bond pattern may be sufficient to provide an equal number of point bonds, or an even distribution of bonded surface area, over each of the later-formed contact elements 162. In another embodiment, the bond pattern may provide an unequal number of point bonds, or a non-uniform distribution of bonded surface area, over multiple later-formed contact elements 162.

In an embodiment, this second bonding (i.e., second securement) operation provides a bond having a bond strength that is greater than the bond strength provided by the first bonding (i.e., first securement) operation. It is understood that the bond strength can be controlled by pressure, energy, temperature, time and pattern used in the bonding process. For example, in the illustrated embodiment the bond pattern provided by this second bonding operation has a higher bond point density, and thus a higher bonded surface area, than the bond pattern provided by the first bonding operation.

Figure 50:
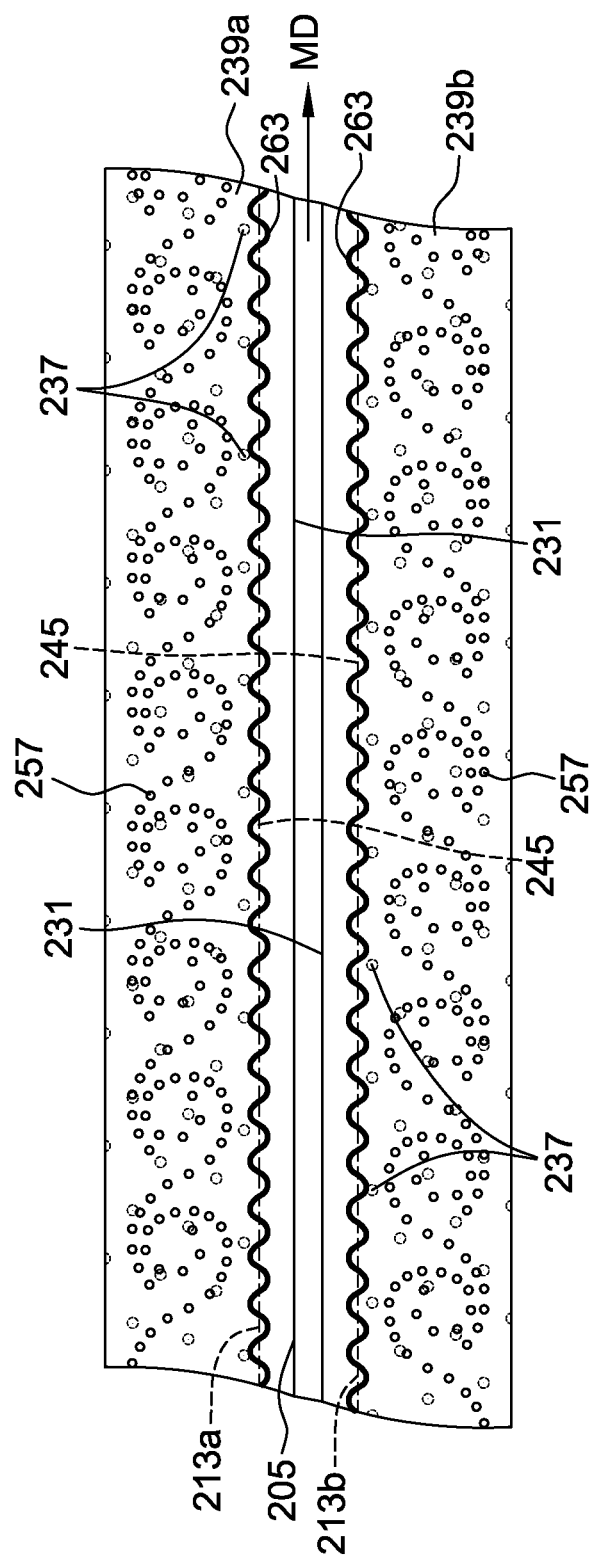
FIG. 50 is a fragmentary top view similar to FIG. 49 but showing inner edges of the folded outer portions of the webs being bonded.

In an embodiment, as illustrated in FIGS. 42 and 44, the securement station 254 further comprises the additional bonding apparatus 261. In the illustrated embodiment, the additional bonding apparatus 261 is also an ultrasonic bonding apparatus and is operable to bond the folded portions of the web 239 of cover material at a location that is at least in part different from the location at which the bond pattern 257 is applied by the upstream bonding apparatus. More particularly, this bonding apparatus 261 bonds at least the folded portion of the web 205 of base material at which the opposed layers of base material face each other without intervening absorbent material therebetween. In one embodiment, as illustrated in FIG. 50, this additional bonding apparatus 261 additionally bonds all of the layers of the folded portion of the web 239 of cover material together generally along the inner side edges 245 of the respective webs 213a, 213b of absorbent material. This additional bonding operation securely encloses the webs 213a, 213b of absorbent material within the folded web 205 of base material. It is contemplated that the bonding apparatus 261 can be any suitable bonding apparatus including, for example, a stitching or sewing apparatus.

In one embodiment, the bond pattern 263 produced by this additional bonding operation is a uniform, generally sinusoidal (e.g., wave) bond pattern. In other embodiments, the bond pattern 263 produced by this additional bonding operation may be any suitable uniform or non-uniform bond pattern. For example, in one embodiment, the bond pattern is an intermittent, offset stitch pattern to inhibit CD movement of the web as it passes through the apparatus 200. The bond strength provided by this additional bonding operation is also greater than the bond strength provided by the first bonding (i.e., first securement) operation.

Downstream of the securement station 254, the folded and bonded web 239 of cover material is subsequently drawn through the slitter 271 which is operable to slit the web of cover material into two discrete, side-by-side webs 239a, 239b of cover material. For example, the web 239 of cover material may be slit along the transverse mid-point of the web, transversely inward of each of the folded portions of the web. In such an embodiment, each web 239a, 239b of cover material thus includes a folded portion and an unfolded portion comprised only of the base material.

In the embodiment illustrated in FIGS. 42 and 44, the webs 239a, 239b of cover material are further drawn through the die cutter 273 or other suitable cutting apparatus. The die cutter 273 is operable to cut slits in the folded portion of each of the webs of cover material, such as to form the slits 156 and corresponding contact elements 162 of the embodiment of FIG. 28. In one suitable embodiment, the die cutter 273 may be operable to cut the slits 96 in a pattern in which a set of equally spaced slits is cut into the folded portions of the webs of cover material along a segment corresponding to the length of cover material to be applied to a single pledget to form a single tampon, followed by a relatively larger gap before the next set of equally spaced slits along a segment corresponding to the next length of cover material to applied to another pledget to form another tampon.

In another embodiment, which is illustrated in FIG. 41, the die cutter 273 may be operable to cut the slits 96 such that each slit is equally spaced in the folded portions of the webs 239 of cover material along a segment P1 corresponding to the length of cover material to be applied to a single pledget to form a single tampon, followed by the next set of equally spaced slits along a segment P2 corresponding to the next length of cover material to applied to another pledget to form another tampon. Thus, in this embodiment, each tampon 10 has the same number of contact elements 196 and each of the contact elements 196 has the same width W and the same length L1. In the illustrated embodiment, for example, each of the tampons 10 formed from the web 239 would have seven complete (i.e., whole) contact elements 196. It is understood, however, that number of contact elements 196 per tampon 10, the width W of each of the contact elements, and length L1 of each of the contact elements can differ. In yet another embodiment, the die cutter 273 may be omitted from the apparatus 300. In such an embodiment, the slits 96 can be formed in a later process as described in more detail below.

In an embodiment, after passing the die cutter 273 (or the slitter 271 if the die cutter is omitted) the webs 239a, 239b of cover material are wound onto respective rolls (not shown) for subsequent transport to a tampon making apparatus where the webs of cover material are each cut into discrete lengths of cover material and applied about the circumference of an absorbent structure, such as a pledget 12, to form a tampon.

Figure 51:
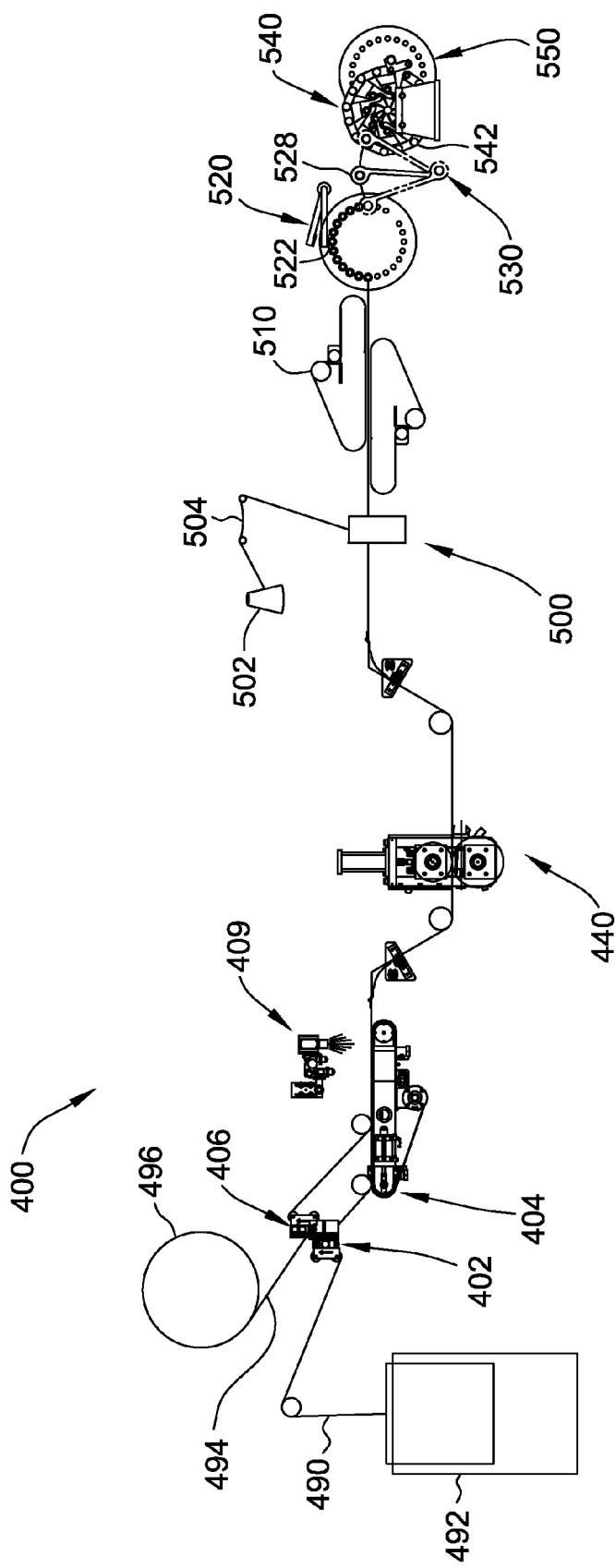
FIG. 51 is a schematic of one suitable embodiment of an apparatus for making the tampon.

FIG. 51 schematically illustrates one suitable embodiment of an apparatus, indicated generally at 400, for making the tampon 10. As seen in FIG. 51, a web 490 (e.g., a web of material suitable for the fleece 30 of the tampon 10) is fed from a suitable supply source (e.g., supply tub 492). In the illustrated embodiment, the web 490 (broadly, "a substrate") is fed from the supply tub 492 by a first web transfer device, indicated generally at 402, to an assembly station, indicated generally at 404.

While the illustrated embodiment of the apparatus 400 shows the web supply source as being the supply tub 492, it is understood that any suitable supply source (e.g., a roll, a barrel) can be used. It is also understood that the web 490 can be formed in-line. For example, the web 490 could be formed using any suitable web forming technique, such as a carding line, and fed directly to the web transfer device (not shown) upon its formation.

The first web transfer device (not shown) is adapted to draw the web 490 from the supply tub 492 at a predetermined rate (i.e., speed) and under a predetermined amount of tension. Web tensioning can suitably be established via the use of conventional tensioning devices (e.g., spindle friction, dancer roll, drive rolls, closed loop tension feedback device, and the like). The first web transfer device 402 also aligns the web 490 in the cross-machine direction (CD direction). In one suitable embodiment, the first web transfer device 402 aligns the web 490 generally along a machine centerline. As mentioned above, the web 490 is fed by the first web transfer device 402 to the assembly station 404.

The transverse, or cross-direction position of the web 490 is established by the position of the unwind equipment (e.g., roll, etc.). Conventional centering components (e.g., shepherds, hooks, vertical idlers, and other suitable centering components) may be used to maintain the transverse or CD position of the web 490 relative to the machine direction MD. In addition to guide rolls, other conventional web handling components may be used to maintain the orientation and centering of the web as it moves through the apparatus, such as guide trays and the like. Suitable web guides and web guide controllers are commercially available, such as, the Fife web guiding system.

Figure 54:
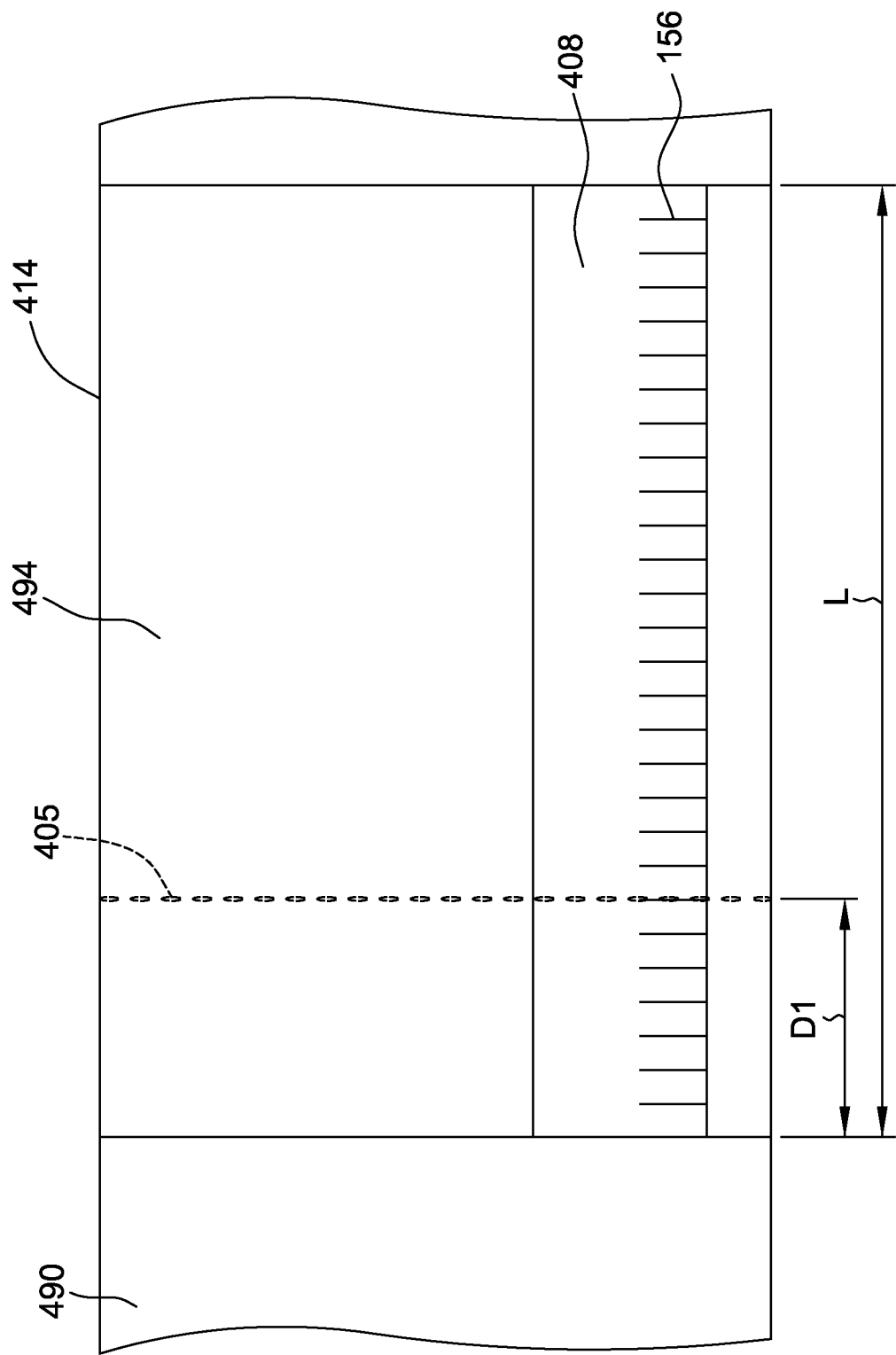
FIG. 54 is a fragmentary top view of the web of cover material overlying a web of fleece.

At the assembly station 404, the web 490 is perforated in the cross-machine direction at predetermined intervals to define transverse lines of weakness 405 in the web (FIG. 54). In one suitable embodiment, the assembly station 404 is configured to perforate the web 490 to define the transverse line of weakness 405 approximately every 256 mm of web. That is, in one embodiment, the lines of weakness 405 are spaced apart approximately every 256 mm along the length of the web 490. It is understood that the lines of weakness 405 can be formed in other suitable ways besides perforating the web 490. For example, the lines of weakness 405 can be formed by embossing, scoring, and/or combinations thereof. It is also understood that the lines of weakness 405 can be spaced apart any suitable distance along the length of the web 490. The web 490 having one of the lines of weakness 405 defined by a plurality of perforations is illustrated in FIG. 54

Simultaneously, a web (or multiple webs) 494 of suitable cover material is provided from a suitable supply source (e.g., supply roll 496). In the illustrated embodiment, the web 494 is fed from the supply roll 496 through a web guide device, indicated generally at 406, to the assembly station 404. In one suitable embodiment, the web 494 of cover material is fed in the machine direction and generally aligned with the web 490 of fleece material. It is understood, however, that one or both of the webs 490, 494 can be fed to the apparatus 400 at any suitable angle including, for example, the cross-section direction. While the illustrated embodiment of the apparatus 400 shows the web supply source as being the supply roll 496, it is understood that any suitable supply source (e.g., a tub, a barrel) can be used. It is also understood that the web 494 can be formed in-line. For example, the web 494 could be formed using the apparatus and methods described above.

Figure 52:
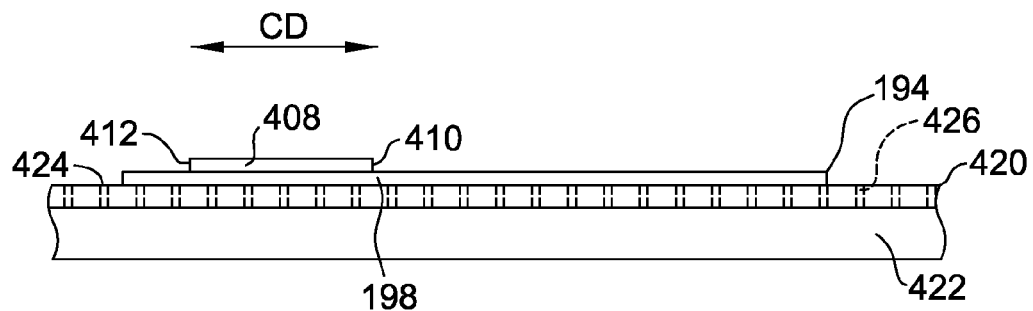
FIG. 52 is a cross-section of a vacuum conveyor being used to hold down and transport a web of cover material.

As seen in FIG. 52, which is a cross-section taken transversely (i.e., in the cross-machine direction) through the web 494, the web in one suitable embodiment comprises a base web 498 and an absorbent web 408 carried by the base web. In the illustrated embodiment, the base web 498 is a continuous web of material suitable for covering the fleece 30 of the tampon 10. It is understood that the base web 498 can have other suitable properties in addition to or instead of being absorbent, such as, for example cleaning and/or wiping. The absorbent web 408 can be a continuous web or a discontinuous web (i.e., discrete pieces) of a suitable absorbent material that is bonded at one end to the base web 498. Thus, the absorbent web 408 has a bonded end 410 and a free end 412 spaced from the bonded end. The free end 412 of the absorbent web 408 can move (e.g., by pivoting the absorbent web about the bonded end 410) relative to the base web 498. It is contemplated that in some embodiments the base web 498 and the absorbent web 408 can be formed as a single, integrated web. It is also contemplated that in some embodiments the absorbent web 408 can be bonded to the base web 498 through the full width (CD direction) of the absorbent web. It is further contemplated that in other embodiments the absorbent web 408 can be free from bonding to the base web 498.

Figure 53:
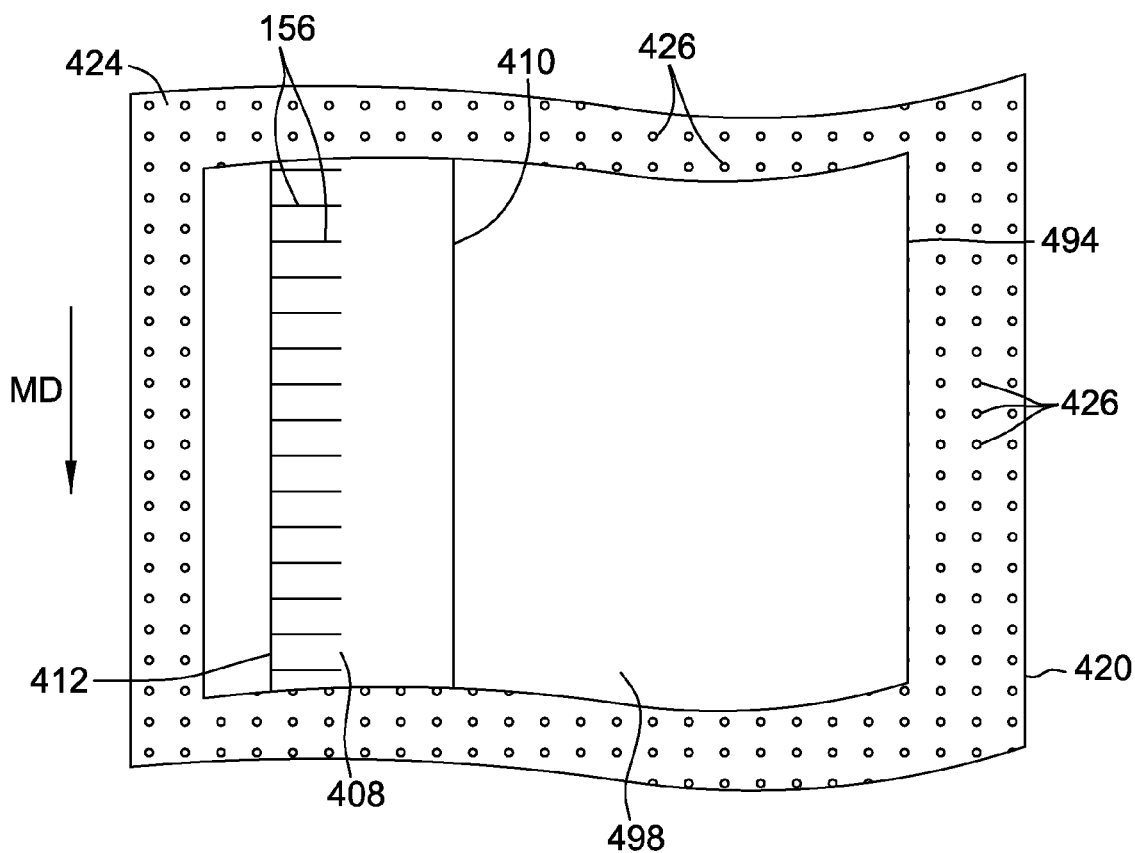
FIG. 53 is a fragmentary top view of the vacuum conveyor and web of FIG. 52.

With reference now to FIG. 53, which is a fragmentary top view of the web 494, the absorbent web 408 has a plurality of slits 96, which are provided to form the contact elements 88 of the tampon 10. As mentioned above, it is contemplated that other components of the tampon 10 can have slits 96 for forming the contact elements 88 of the tampon 10. It is also contemplated that the slits 96 can be preformed (i.e., formed before web 494 is to be used as the supply roll 496) or formed during the manufacturing of the tampon 10 as described in more detail below.

With reference again to FIG. 51, the second web transfer device 406 is adapted to draw the web 494 from the supply roll 496 at a predetermined rate (i.e., speed) and under a predetermined amount of tension. Web tensioning can suitably be established via the use of conventional tensioning devices (not shown) (e.g., spindle friction, dancer roll, drive rolls, closed loop tension feedback device, and the like). In one suitable embodiment, a second web transfer device (not shown) is adapted to control the wrinkling and/or to remove wrinkles present in one or both of the webs 494, 490. Web tensioning also provides the appropriate strain match during the combining of the webs 490, 494.

It is also contemplated that the second web transfer device 406 can be configured to detect splices or other defects in the web 494, to control/remove dust from the web, and/or to inhibit static charges from building up in the web. The second web transfer device 406 also aligns the web 494 in the cross-machine direction (CD direction). In one suitable embodiment, the second web transfer device 406 aligns the web 494 with the other web 490 (i.e., the web of fleece 30 material) generally along the machine centerline.

The transverse, or cross-direction position of the web 494 is established by the position of the unwind equipment (e.g., roll, etc.). Conventional centering components (e.g., shepherds, hooks, vertical idlers, and other suitable centering components) may be used to maintain the transverse or CD position of the web 494 relative to the machine direction MD. In addition to guide rolls, other conventional web handling components may be used to maintain the orientation and centering of the web as it moves through the apparatus, such as guide trays and the like. Suitable web guides and web guide controllers are commercially available, such as, the Fife web guiding system.

Thus, both of the webs 490, 494 are registered in both the MD and CD direction. In other words, both of the webs 490, 494 are aligned relative to one or more reference points. The one or more reference points can be a portion of the web 490, 494 itself, a portion of the other web, a component (or portion thereof) of the apparatus 400, and/or combinations thereof. In one suitable embodiment, CD registration is ±2 mm and MD registration is ±3 mm of the webs 490, 494 and can be measured by Photoeyes, vision system, visual indicators, rulers, and other conventional measuring techniques.

As mentioned above, the web 494 of cover material is fed from the second web transfer device (not shown) to the assembly station 404. At the assembly station 404, the web 494 is cut or perforated in the cross-machine direction into discrete web segments 414 having a predetermined length L (FIG. 54). In the illustrated embodiment, for example, each of the web segments 414 have a length of approximately 128 mm. It is understood that the web segments 414 can be cut into any suitable lengths.

During the cutting process, the absorbent web 408 of the web 494 is controlled to ensure that it is cut properly along with the base web 494. In one suitable embodiment, the absorbent web 408 is held against the base web 494 by a suitable hold down device to maintain the absorbent web 408 in proper registration with the base web 494 as the web segments 414 are cut from the web 494. The hold down device can be, for example, air-knife, vacuum covers, vacuum conveyor, ski, folding board, nip roll, fold finger, surface coatings, and/or side vacuum assist. The hold down device in the form of a vacuum conveyor 420 is illustrated in FIGS. 52 and 53. The illustrated vacuum conveyor 420 comprising a vacuum chamber 422 and a conveyor belt 424 having a plurality of apertures 426 for allowing the vacuum to act on the web 494 (i.e., both the base web 494 and the absorbent web 408). The apertures are of appropriate size and distribution to act effectively on each contact element if cut, or the pattern is registered in the MD and CD to control the contact elements.

In the illustrated embodiment, the discrete web segments 414 are placed on the perforated, continuous web 490 of fleece material at predetermined spaced intervals. In one suitable embodiment, which is illustrated in FIG. 54, the web segments 414 are placed on the web 490 such that web segments extends over the lines of weakness 405 formed in the web by a predetermined distance D1. It is understood, that the web segments 414 can be placed on the web 490 in any suitable manner.

More specifically, the cutting and placing of segment 414 is mechanically linked to the perforating of continuous web 490 to establish MD registration of the discrete web segment, the continuous web and the slits 159, wherever they are applied. In one suitable embodiment, the assembly station 404 may include a vision/closed loop automated or manual phasing system to ensure that the MD registration of discrete web segment 414, the continuous web 490 and the slits 159 is within a predetermined tolerance. In one suitable embodiment, the tolerance of dimension D1 is within the range of 25 mm and 31 mm and more suitably about 28 mm.

While still at the assembly station 404, each of the discrete web segments 414 is bonded (e.g., pressure bonded, thermal bonded, ultrasonically bonded, adhesively bonded) to the web 490. In the illustrated embodiment, for example, each of the web segments 414 is thermally bonded to the web 490. More specifically, the base web 494 of each of the web segments 414 is thermally bonded to the web 490 while the absorbent web 408 of each of the web segments is free from bonding.

Figure 55:
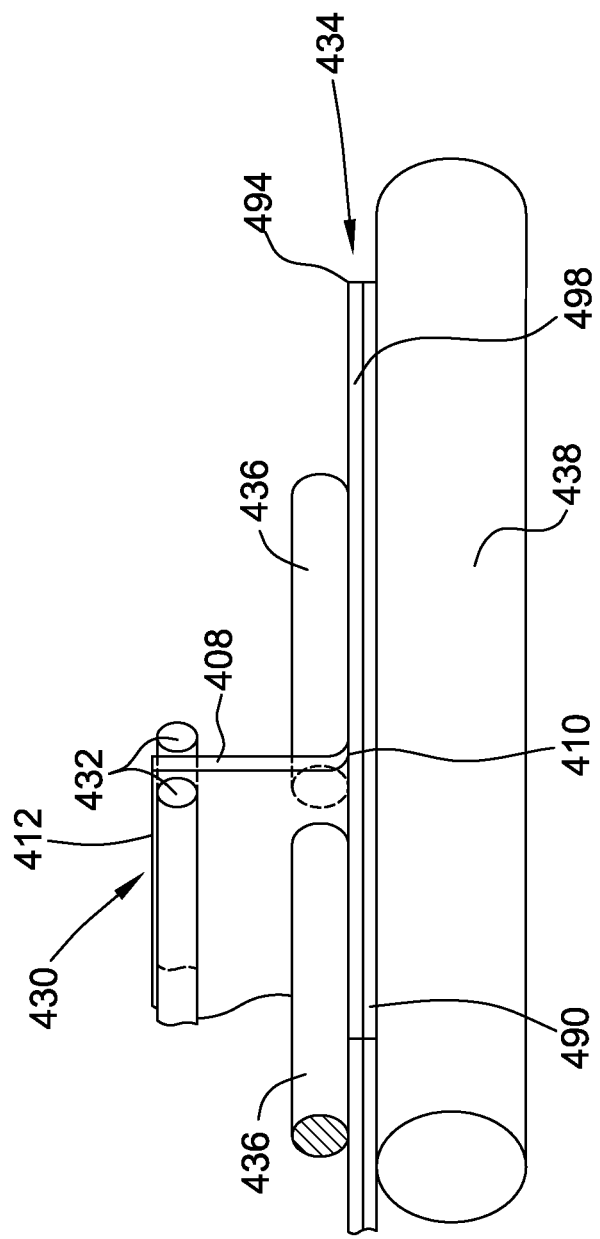
FIG. 55 is a perspective illustrating the web of cover material being bonded to the web of fleece at an assembly station of the apparatus of FIG. 51.

In one suitable embodiment, which is illustrated in FIG. 55, the base web 494 of each of the segments 414 is thermally bonded to the web 490 by feeding the base web 494 and the web 490, which is aligned with the base web, through a nip 434 defined by a pair of spaced-part upper rolls 436 and a lower roll 438. The upper rolls 436 are sufficiently spaced apart to allow the absorbent web 408 of each of the web segments 414 to pass between the upper rolls. While the lower roll 438 is illustrated as being a single roll, it is understood that the lower roll could be formed as two separate spaced apart rolls similar to the upper rolls 436.

As illustrated in FIG. 55, the assembly station 404 comprises an absorbent web controller, indicated generally at 430, for positioning the absorbent web 408 such that the base web 494 can be suitably bonded to the web 490. In the illustrated embodiment, for example, the absorbent web controller 430 comprises a pair of rods 432 for pivoting the absorbent web about its bonded end 410 to a generally perpendicular position such that the free end 412 is spaced from the base web 494. It is contemplated that the absorbent web controller 430 can be other suitable web controllers including, but not limited to, proper tension, horizontal-straight-through webpaths, conveyors, vacuum conveyors, vacuum rolls, roll to roll transfer, air-knifes, skis, rotating discs, nip rolls, fold fingers, surface coatings, and/or side vacuum assist. Also is a requirement to control the contact elements once cut to ensure they stay in their registered placement, are active and able to open to the outside of the tampon and are undamaged. Any combination of the web controlling items listed above would be employed after the contact elements are cut in the web to maintain control throughout the process.

After the web segments 414 are bonded to the continuous web 490, a secondary bond 473 can be added to bond the absorbent web 408 to the base web 498 (FIG. 54). In one suitable embodiment, the secondary bond 473 is limited to an area or a portion of the area that will be overlapped in the soft roll forming process, which is described in more detail below. In such an embodiment and as illustrated in FIG. 54, the secondary bond 473 would be disposed on the trailing side of the line of weakness 405. Thus, the secondary bond 473 should be sufficient to bond the absorbent web 408 to the base web 498. However, the secondary bond 473 should not bond the base web 798 to the underlying web 490. While the illustrated secondary bond 473 comprises point bonding, it is understood that any suitable bonding technique can be used to bond the absorbent web 408 to the base web 498.

In one suitable embodiment, the assembly station 404 further comprises an inspection system (e.g., one or more photo eyes), indicated generally at 409 in FIG. 51, adapted to inspect one or more of the following—the lines of weakness 405 formed in the web 490 of fleece material, the cuts in the web 494 to form the discrete web segments 414, the placement of the web segments 414 on the web 490 of fleece material (e.g., cross-machine direction alignment, machine direction alignment) and the bonding of the discrete web segments 414 to the web 490.

As mentioned above, the slits 96 in the absorbent web 408 of the discrete web segments 414 can be preformed (i.e., formed before web 494 is used as the supply roll 496) or formed during the manufacturing of the tampon 10. In an embodiment, the die cutting module is mechanically linked to the perforating cutters of the fleece and cover material and is phasable in order to maintain precise registration of the contact elements cuts and/or dead zones to the edges of the other materials. This could also be done via servo drives, phasing gearboxes, etc. In one suitable embodiment wherein the slits 96 are formed during the manufacturing of the tampon 10, the web 490 having the discrete web segments 414 bonded thereto is fed from the assembly station 404 to a die cutting station 440 adapted to cut slits 96 in absorbent web 408.

In one suitable embodiment, the die cutting station 440 includes an absorbent web controller, indicated generally at 442, for positioning the absorbent web 408 such that the absorbent web can be suitably cut at the cutting station to form the slits 96. The die cutting station 440 is operable to cut slits in the folded portion of the web 494 of cover material, such as to form the slits 156 and corresponding contact elements 162 of the embodiment of FIG. 28. In an embodiment, the die cutting station 440 may be operable to cut the slits in a pattern in which a set of equally spaced slits is cut into the folded portions of the web 494 of cover material along a segment corresponding to the length of cover material to be applied to a single pledget to form a single tampon, followed by a relatively larger gap before the next set of equally spaced slits along a segment corresponding to the next length of cover material to applied to another pledget to form another tampon.

In another embodiment, which is illustrated in FIG. 41, the die cutting station 440 may be operable to cut the slits 156 such that each slit is equally spaced in the folded portions of the web of cover material along a segment P1 corresponding to the length of cover material to be applied to a single pledget to form a single tampon, followed by the next set of equally spaced slits along a segment P2 corresponding to the next length of cover material to applied to another pledget to form another tampon. Thus, in this embodiment, each tampon 10 has the same number of contact elements 196 and each of the contact elements 196 has the same width W and the same length L1. In the illustrated embodiment, for example, each of the tampons 10 formed from the web 494 would have seven complete (i.e., whole) contact elements 196. It is understood, however, that number of contact elements 196 per tampon 10, the width W of each of the contact elements, and length L1 of each of the contact elements can differ.

Figure 56:
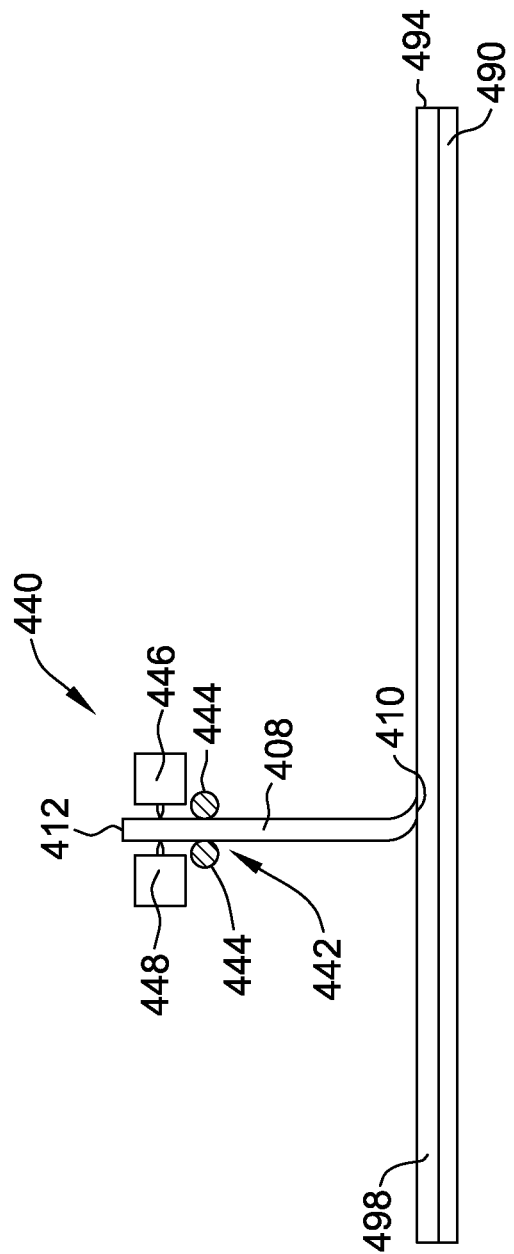
FIG. 56 is an end view illustrating the web of cover material being cut to form slits therein at a cutting station of the apparatus.

In the embodiment illustrated in FIG. 56, the absorbent web controller 442 comprises a pair of support rods 444 for holding the absorbent web 408 in a generally perpendicular position such that the free end 412 of the absorbent web is spaced from the base web 494 and can be acted on a suitable cutting device (e.g., a knife roll 446 and anvil roll 448 as illustrated in FIG. 56). It is contemplated that the absorbent web controller 442 can be other suitable web controllers including, but not limited to, proper tension, horizontal-straight-through webpaths, conveyors, vacuum conveyors, vacuum rolls, roll to roll transfer, air-knifes, skis, rotating discs, nip rolls, fold fingers, surface coatings, and/or side vacuum assist. Also is a requirement to control the contact elements once cut to ensure they stay in their registered placement, are active and able to open to the outside of the tampon and are undamaged. Any combination of the web controlling items listed above would be employed after the contact elements are cut in the web to maintain this control throughout the process (especially through the stringing module and into the soft winding station). The die cutting station can include a suitable inspection system (e.g., one or more photo eye) for ensuring that the slits 96 are properly cut in the absorbent web 408.

Figure 57:
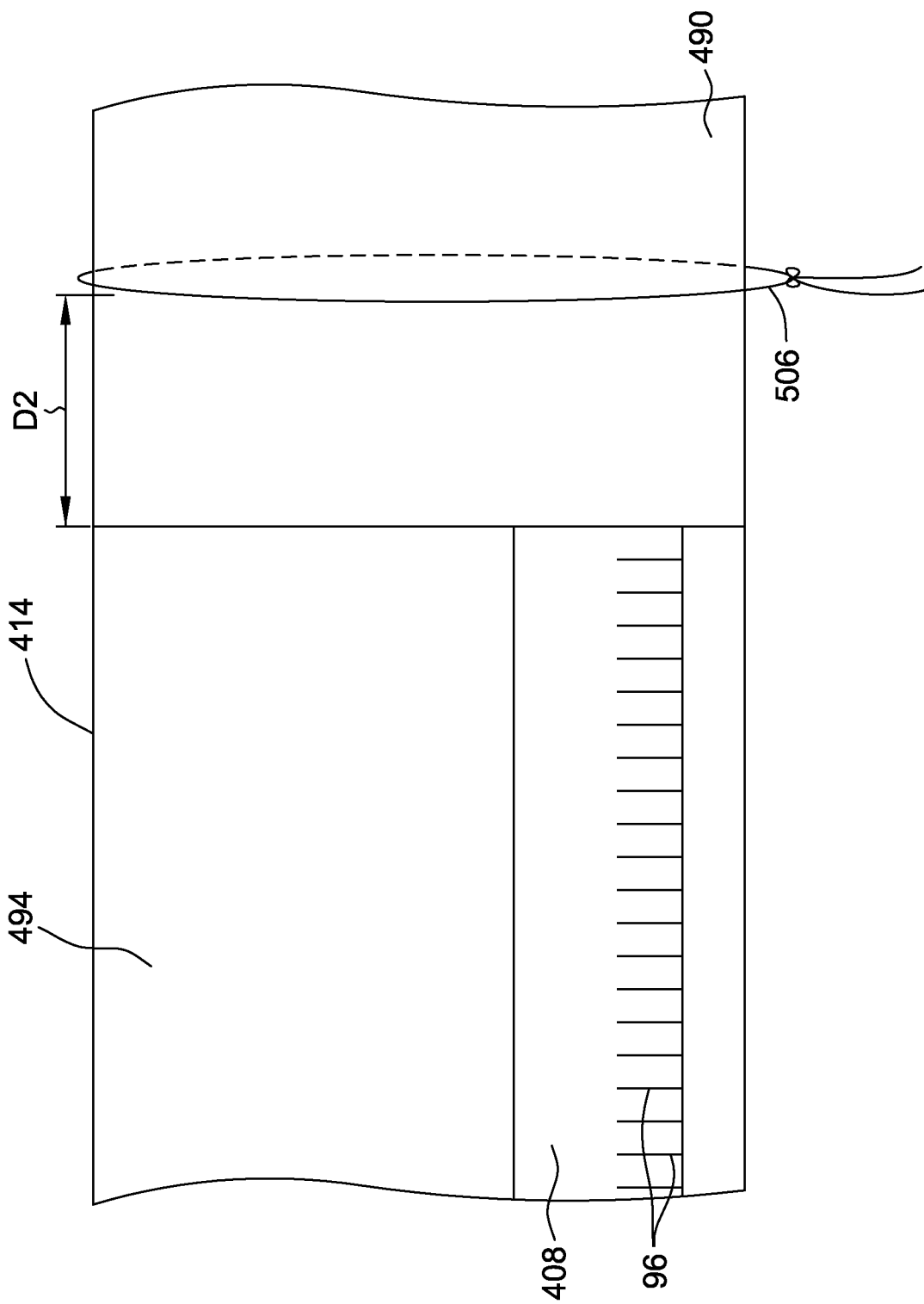
FIG. 57 is a top view of the webs of cover material and fleece passing through the apparatus and having a withdrawal aid attached thereto.

As seen in FIG. 51, the apparatus 400 comprises a withdrawal aid placement station 500 having a suitable supply source 502 of a continuous supply of string 504 (or other suitable withdrawal aid material) suitable for use as the withdrawal aid 14 of the tampon 10. As illustrated in FIG. 57, the string 502 can be cut and wrapped around the web 490 at a predetermined located spaced from the discrete web segments 414. More specifically, a cut portion 506 of the string 502 is wrapped around the web 490 at a predetermined distance D2 from a leading edge of the web segment 414. In one suitable embodiment, the distance D2 corresponding to the distance between the string 502 and leading edge of the web segment 414 is approximately equal to the distance D1 corresponding to the distance between the line of weakness 405 formed in the web 490 and a trailing edge of the web segment. It is understood that the distances D1, D2 can be different. For example, in the illustrated embodiment, the string 504 can be located approximately 170.7 mm forward from the trailing line of weakness 405. In other words, the string 504 can be located at a location approximately two-thirds the distance between adjacent leading and trailing lines of weakness 405. In other words, the string 504 is registered in both the CD and MD directions.

As seen in FIG. 57, the cut portion 506 of the string 502 wrapped around the web 490 extends beyond the web and is positioned such that both ends of the cut portion are generally adjacent each other. The part of the cut portion 506 extending beyond the web 490 is rolled and/or tied to form the knot 444 in the withdrawal aid 14 of the tampon 10. In one suitable embodiment, an inspection system (e.g., one or more photo eyes) is provided at the withdrawal aid placement station 500 to ensure, for example, that the cut portion 506 of the string 502 is located properly relative to the web segment 414 and/or that the knot 444 is properly formed.

After the part of the cut portion 506 extending beyond the web 490 is tied, the web is conveyed by a ribbon transport device 510 (e.g., upper and lower spaghetti conveyors) to a suitable winding and sealing device, indicated generally at 520. In the embodiment illustrated in FIG. 51, the ribbon transport device 510 is a pair of opposed conveyors. In one suitable embodiment, the opposed conveyors may employ metal fingers to move the main ribbon. Suitably, the metal fingers of the opposed conveyors are MD registered to inhibit damage to the contact elements. The winding and sealing device 520 is configured to separate the web 490 about the line of weakness 405 into individual units as the web is being fed to the winding and sealing device. Each of the individual units corresponds to a single tampon 10.

After being separated from the web 490, each of the units is manipulated (e.g., rolled or folded) to form a softwind wherein the fleece material defines the core and the cover overlies and covers the fleece material such as illustrated in FIG. 25. In this embodiment, however, the cover is carrying the absorbent web 408 having the plurality of slits 96, which are provided to form the contact elements 196 of the tampon 10.

As the soft wind process begins, a secondary absorbent tucker apparatus (not shown) can be used to ensure the absorbent web 408 is tucked into a soft wind cup and to maintain parallelism through the winding process without damaging the contact elements 196. The wind process needs to be MD registered and timed to complete its operation during the winder dwell time. As a result, predictable and repeatable angular rotation of the softwind cups from loading through each dwell point through ejection is required.

A cover to cover sealing device 522 is provided to seal the overlapping portions of the web segments 414 (FIG. 51). More specifically, the portion of the base web 494 defining the cover of the tampon 10 is overlapped upon itself and heat sealed along the overlap. In one suitable embodiment, the overlap generally corresponds to the distance D1 between the trailing edge of the web segment 414 and the line of weakness 405 formed in the web 490. It is understood, however, cover can be sealed using any suitable technique and that the cover can have other suitable overlaps. It is also understood that the cover can be free from overlap (e.g., when the cover is sealed end-to-end). Suitably, the seal is sufficient to withstand the further processing and use.

In one suitable embodiment, the cover to cover sealing device 522 can be MD registered and timed to act during the soft wind dwell time. The cover-to-cover bond of the web segment 414 can be a continuous bond pattern or several different bond points acting with different patterns, pressures, and temperatures. This bond could also be registered in to relation with the angular position of the winding forks in each winding cup. Additionally, back pressure from the winding forks may be needed to ensure reliable seal.

Concentric ejecting and receiving transfer points aid in minimizing damage and misalignment of the absorbent web 408 during transfer of the soft wind. It is contemplated that the contact surfaces of the transfer points may be tapered, coated, patterned to inhibit misalignment and damage of the absorbent web. These may be CD or MD registered relative to the contact element locations, cover to cover sealing and geometry features of the compressor.

As noted above, the individual units can also be stacked, folded or otherwise manipulated into the softwind. For example, suitable menstrual tampons may include "cup" shaped pledgets like those disclosed in U.S. Publication No. 2008/0287902 to Edgett and U.S. Pat. No. 2,330,257 to Bailey; "accordion" or "W-folded" pledgets like those disclosed in U.S. Pat. No. 6,837,882 to Agyapong; "radially wound" pledgets like those disclosed in U.S. Pat. No. 6,310, 269 to Friese; "sausage" type or "wad" pledgets like those disclosed in U.S. Pat. No. 2,464,310 to Harwood; "M-folded" tampon pledgets like those disclosed in U.S. Pat. No. 6,039, 716 to Jessup; "stacked" tampon pledgets like those disclosed in U.S. 2008/0132868 to Jorgensen; or "bag" type tampon pledgets like those disclosed in U.S. Pat. No. 3,815,601 to Schaefer.

A suitable method for making "radial wound" pledgets is disclosed in U.S. Pat. No. 4,816,100 to Friese. The radial winding method can also include a method for forming the blank into a pledget like that disclosed in U.S. Pat. No. 6,310, 269 to Friese. Suitable methods for making "W-folded" pledgets are disclosed in U.S. Pat. No. 6,740,070 to Agyapong; U.S. Pat. No. 7,677,189 to Kondo; and U.S. 2010/0114054 to Mueller. A suitable method for making "cup" pledgets and "stacked" pledgets is disclosed in U.S. 2008/0132868 to Jorgensen.

Figure 38:
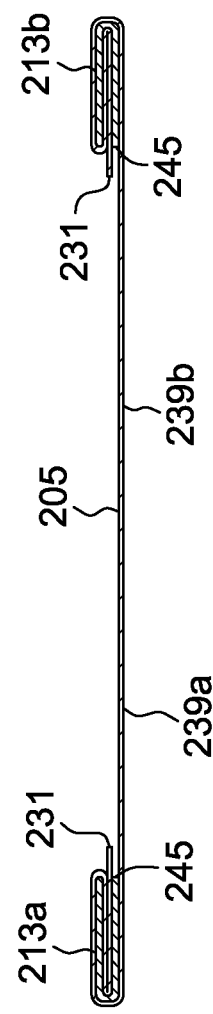
FIG. 38 is a cross-section similar to FIG. 37 but showing outer portions of the webs being folded inward.
Figure 39:
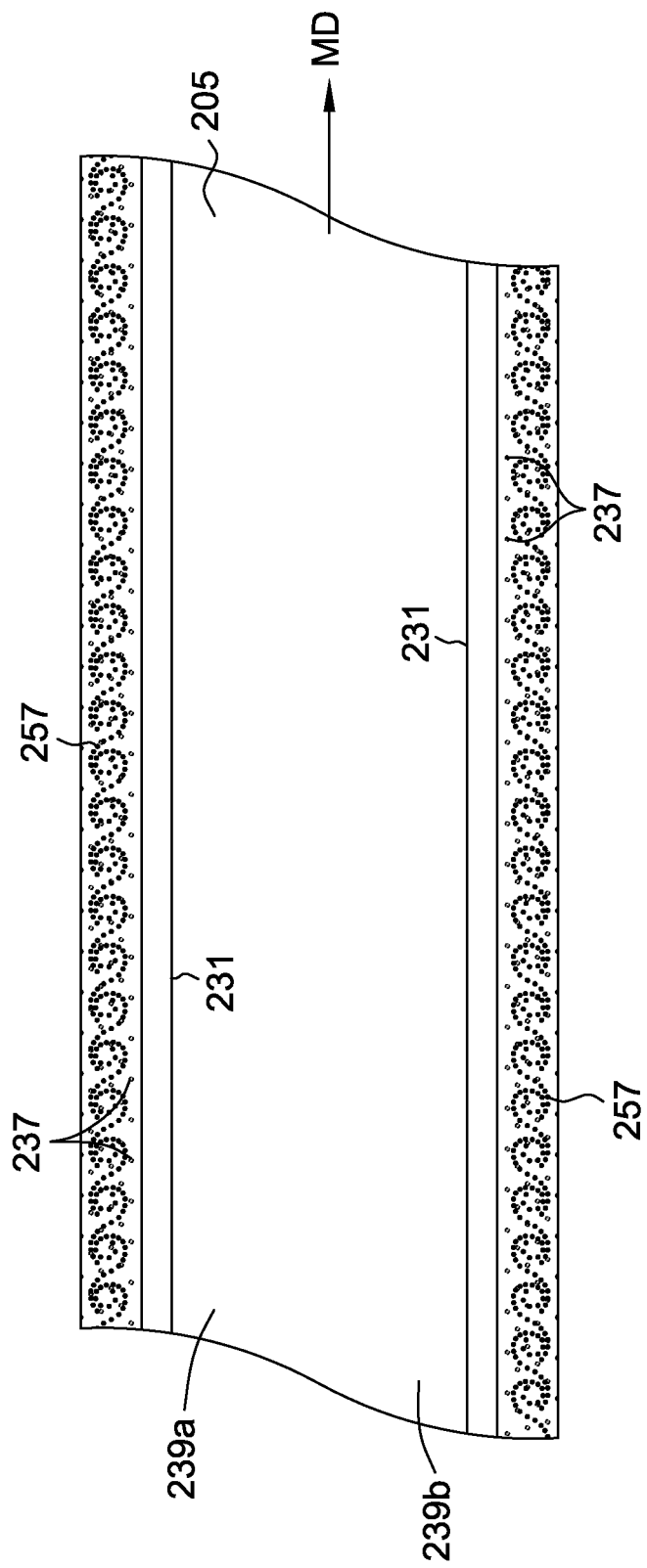
FIG. 39 is a fragmentary top view of the webs of FIG. 38 with the folded outer portions of the webs being bonded.

The softwind is then pushed from the winding and sealing device 520 by a suitable push rod (not shown) into a cup 528 of an articulating arm, indicated generally at 530 (FIG. 38). As illustrated in FIG. 51, the articulating arm 528 transport the softwind from the winding and sealing device 520 to a compression station, indicated generally at 540. More specifically, a push rod (not shown) pushes the softwind from the cup 528 of the articulating arm 530 into one of a plurality of mold cavities 542 formed in a compressor of the compression station 540.

CD registration in the articulating arm 530 is established by eject arm stroke length or stop points in the arm. The articulating arm 530 is used to bring the soft wind from the winding and sealing device 520 to the compression station 540 in a repeatable and predictable angular position. In order to achieve a desired angular position, the articulating arm 530 may be capable of rotating the soft wind while transferring it. This may be controlled by inspection stations before, during, and or after transportation of the soft wind. Concentric ejecting and receiving transfer points aid in minimizing the damage and misalignment of the absorbent web 408 during transfer of the soft wind. Additionally, the contact surfaces of the transfer points may be tapered, coated, patterned to prevent misalignment and damage and the absorbent web 408. The ejection process (i.e., the process of removing the soft wind from the cup 528) is controlled to register the soft wind in the CD in the articulating arm 530. Additionally, the articulating arm 530 can be capable of rotating the soft wind 180 degrees to reverse the nose and string end of the tampon.

During exit of the soft wind from the articulating arm 530 to one of mold cavities of the compressor of the compressor station 540, CD registration is controlled by the push length of the ejecting apparatus and/or stop points in the compressor. The angular position of the soft wind (i.e., the position about the circumference of the soft wind) established by the articulating arm 530 is maintained, such as, by guide rails as the soft wind enters the compressor. The compressor geometry can be such that in the open position there is oversized clearance or tapered, coated, patterned surfaces to protect the absorbent web 408 during CD transport into the compressor. It is contemplated that the ejecting apparatus can be adapted to rotate the soft wind in addition to or instead of the articulating arm 530.

The compressor (e.g., compressive jaws of the compressor) can have any suitable pattern to facilitate compression of the soft wind while maintaining the integrity of the absorbent web 408 including the contact elements. For example, the compressive jaws can have a continuous pattern that varies in the CD direction and/or its annularity. For example, the compressive can vary in actuation depth or can have relief (i.e., a cutout) to accommodate the absorbent web 408 and, more particularly, the contact elements during the compression of the soft wind. It is contemplated that the compressive jaws can be arranged to act on the contact elements and/or slits in the absorbent web 108, can be arranged not to act on the contact elements and/or slits, or a combination thereof.

In one suitable embodiment, when the softwind is positioned within one of the mold cavities of the compression station 540, a plurality of dies moves towards one another and compress the softwind. In some suitable embodiments, the compression station 540 is adapted to apply heat to the softwind. The softwind can be compressed any suitable amount. For example, the softwind may be compressed at least about 25%, 50%, or 75% of the initial dimensions. For example, the softwind can be reduced in diameter to approximately ¼ of the original diameter. The cross-sectional configuration of the resultant tampon 10 may be circular, ovular, rectangular, hexagonal, or any other suitable shape.

The compressed soft wind (i.e., the pledget) exits the compressor of the compression station 540 into one of a plurality of holding tubes. CD registration of the pledget is controlled and the angular position of the pledget (i.e., the position about the circumference of the pledget) established by the articulating arm 530 is maintained as the pledget enters the respective holding tube.

A suitable nose forming apparatus (not shown) of the compression station 540 forms the nose of the pledget. Thus, the location of the pledget within the holding tube must be concentric predictable, and repeatable. In one suitable embodiment, the location of the pledget within the holding tube can be accomplished via mechanical linkages.

Once formed, the tampons 10 are pushed from the mold cavities 542 of the compression station 540 by a push rod (not shown) in to a suitable wrapper at a wrapping and sealing station, indicated generally at 550, for sealing the tampons. The wrapping and sealing station 550 is configured to wrap each of the tampons 10 in the wrapper and to seal the wrapped. After the tampons 10 are wrapped and sealed in the wrapper at the wrapping and sealing station 550, the tampons can be packaged for sale (i.e., placed in boxes suitable for sale to consumers). It is contemplated that the tampons 10 can be placed into suitable applicators (not shown) prior to being wrapped and sealed at the wrapping and sealing station 550.

Figure 58:
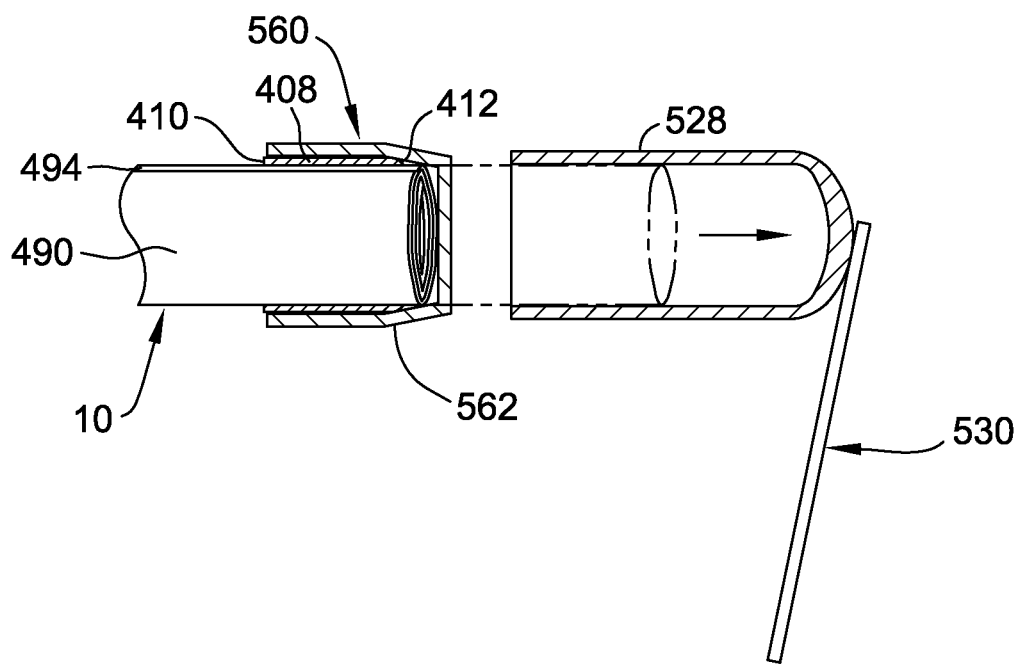
FIG. 58 is a side view of a transfer assist device for facilitating the transfer of a softwind.

During the transfer of the softwind from the winding and sealing device 520 to the cup 528 of an articulating arm 530 (which is illustrated in FIG. 58) and/or the transfer of the softwind from the cup of the articulating arm into one of the plurality of mold cavities 542 formed in the compression station 540, a transfer assist device, indicated generally at 560 in FIG. 58, facilitates the transferring for the softwind while maintaining the proper positioning of the portion of the absorbent web 408 forming the softwind relative to the portion of the base web 494 forming the softwind. In one suitable embodiment, the transfer assist device 560 is a tapered guide 562 adapted to direct the tampon 10 into the cup 528 or the respective mold cavity 542 (the cup 528 being seen in FIG. 58). More specifically, the tapered guide 562 is adapted to direct the free end 412 or bonded end 410 (depending on the direction the softwind is being pushed and the direction in which the free end and bonded end are oriented) into the cup 528 or respective mold cavity 542 while inhibiting the portion of the absorbent web 408 forming the softwind from becoming misaligned (e.g., wrinkled, creased, folded) with respect to the portion of the base web 494 forming the softwind. It is understood that the transfer assist device 560 can be other types of suitable devices including, for example, an air-knife, vacuum covers, vacuum conveyor, ski, folding board, nip roll, fold finger, surface coatings, and/or side vacuum assist.

It is contemplated that once the contact elements are formed in the web of cover material, air flow (e.g., shielding, hold down devices, deflectors, vacuum) can be used to avoid disruption of the contact elements as the web of cover material is moving through the process. It is also contemplated that static energy and humidity can be controlled through all or portions of the process. Static energy, for example, can be controlled using de-ionizing bars, static eliminators, grounding "tinsels," or other suitable grounding techniques.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of manufacturing a tampon comprising:
   transporting a web of material in a machine direction, the web of material comprising a base web for defining a cover material of the tampon and an absorbent web, the base web having opposing longitudinally extending side edges, the absorbent web having a free end and a bonded end wherein the bonded end is bonded to the base web, the free end and bonded end of the absorbent web being disposed inward from the side edges of the base web such that the entire absorbent web overlies and is carried by the base web, the free end including a plurality of slits extending in a cross-machine direction;
   controlling at least the free end of the absorbent web of the web to inhibit movement of the absorbent web relative to the base web;
   cutting the web of material in the cross machine direction to form discrete web segments while controlling at least the free end of the absorbent web; and
   bonding the discrete web segments to a substrate.

2. The method set forth in claim 1 wherein controlling at least the free end of the absorbent web of the web comprises controlling at least the free end of the absorbent web using a hold down device.

3. The method as set forth in claim 2 wherein controlling at least the free end of the absorbent web using the hold down device comprises controlling at least the free end of the absorbent web using at least one of an air-knife, vacuum covers, vacuum conveyor, ski, folding board, nip roll, fold finger, surface coatings, and side vacuum assist.

4. The method as set forth in claim 1 wherein bonding the discrete web segments to the substrate comprises bonding the discrete web segments to a continuous web of fleece material.

5. The method as set forth in claim 4 further comprising transporting the continuous web of fleece material in the machine direction and aligning the continuous web of fleece material with the base web.

6. The method as set forth in claim 5 further comprising bonding the base web of the discrete web segments to the continuous web of fleece material.

7. The method as set forth in claim 1 further comprising inspecting the substrate having the discrete web segments bonded thereto.

8. The method as set forth in claim 1 further comprising registering a string with the substrate, the string being spaced from the discrete web segments.

\* \* \* \* \*